(12) United States Patent
Hong et al.

(10) Patent No.: US 10,543,171 B2
(45) Date of Patent: Jan. 28, 2020

(54) DERMAL DRUG DELIVERY USING AMPHIPHILIC DENDRON-COIL MICELLES

(71) Applicant: THE BOARD OF TRUSTEES OF THE UNIVERSITY OF ILLINOIS, Urbana, IL (US)

(72) Inventors: Seungpyo Hong, Madison, WI (US); Yang Yang, Ellicott City, MD (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 15/807,185

(22) Filed: Nov. 8, 2017

(65) Prior Publication Data

US 2018/0221277 A1 Aug. 9, 2018

Related U.S. Application Data

(63) Continuation of application No. 14/769,704, filed as application No. PCT/US2014/017762 on Feb. 21, 2014, now abandoned.

(60) Provisional application No. 61/767,902, filed on Feb. 22, 2013.

(51) Int. Cl.
| | |
|---|---|
| *A61K 9/107* | (2006.01) |
| *A61K 9/00* | (2006.01) |
| *A61K 47/10* | (2017.01) |
| *A61K 47/34* | (2017.01) |
| *C08G 83/00* | (2006.01) |
| *C08G 63/664* | (2006.01) |
| *C08G 63/685* | (2006.01) |
| *A61K 31/138* | (2006.01) |

(52) U.S. Cl.
CPC .......... *A61K 9/1075* (2013.01); *A61K 9/0014* (2013.01); *A61K 31/138* (2013.01); *A61K 47/10* (2013.01); *A61K 47/34* (2013.01); *C08G 63/664* (2013.01); *C08G 63/6852* (2013.01); *C08G 83/004* (2013.01); *C08G 83/008* (2013.01)

(58) Field of Classification Search
CPC .................................................. A61K 9/1075
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,472,509 A | 9/1984 | Gansow et al. |
| 4,584,355 A | 4/1986 | Blizzard et al. |
| 4,585,836 A | 4/1986 | Homan et al. |
| 4,591,622 A | 5/1986 | Blizzard et al. |
| 4,655,767 A | 4/1987 | Woodard et al. |
| 4,978,532 A | 12/1990 | El-Rashidy |
| 5,021,236 A | 6/1991 | Gries et al. |
| 5,474,783 A | 12/1995 | Miranda et al. |
| 5,656,386 A | 8/1997 | Scherer et al. |
| 5,709,878 A | 1/1998 | Rosenbaum et al. |
| 6,221,383 B1 | 4/2001 | Miranda et al. |
| 7,141,237 B2 | 11/2006 | Abram et al. |
| 9,212,258 B2 | 12/2015 | Hong et al. |
| 9,770,413 B2 * | 9/2017 | Hong .................. C08G 63/912 |
| 2005/0244485 A1 | 11/2005 | Hsu et al. |
| 2014/0037747 A1 | 2/2014 | Hong et al. |
| 2016/0008282 A1 | 1/2016 | Hong et al. |

FOREIGN PATENT DOCUMENTS

| | | |
|---|---|---|
| WO | WO-2004/039957 A2 | 5/2004 |
| WO | WO-2006/133099 A2 | 12/2006 |
| WO | WO-2010/018286 A1 | 2/2010 |
| WO | WO-2010/124227 A2 | 10/2010 |
| WO | WO-2011/009991 A2 | 1/2011 |
| WO | WO-2012/116073 A2 | 8/2012 |

OTHER PUBLICATIONS

Al-Jamal et al., Liposomes: from a clinically established drug delivery system to a nanoparticle platform for theranostic nanomedicine, Acc. Chem. Res., 44(10):1094-104 (2011).
Al-Jamal et al., Supramolecular structures from dendrons and dendrimers, Adv. Drug Deliv. Rev., 57(15):2238-70 (2005).
Aranda et al., Development of a methodology to quantify tamoxifen and endoxifen in breast cancer patients by micellar liquid chromatography and validation according to the ICH guidelines, Talanta, 84(2):314-8 (2011).
Babu et al., Dendrimers: A new carrier system for drug delivery, Int. J. Pharm. Appl. Sci., pp. 1-10 (2010).
Bachhav et al., Novel micelle formulations to increase cutaneous bioavailability of azole antifungals, J. Control. Release, 153(2):126-32 (2011).
Bae et al., Dendron-mediated self-assembly of highly PEGylated block copolymers: a modular nanocarrier platform, Chem. Commun. (Camb.), 47(37):10302-4 (2011).
Barbosa-Barros et al., Lipid nanostructures: self-assembly and effect on skin properties, Mol. Pharm., 6(4):1237-45 (2009).
Becher et al., Nonionic Surfactants Physical Chemistor, New York: Marcel Dekker (1987).
Benavides et al., The hairless mouse in skin research, J. Dermatol. Sci., 53(1):10-8 (2009).
Bentley, Synthesis and characterization of amphiphilic dendron coils: a potential nanomicelle platform, Final RET 2011 Report, Naperville Central High School (Aug. 5, 2011).
Binder et al., 'Click' Chemistry in Polymer and Material Science: An Update, Macromol. Rapid Commun., 29(12-13):952-81 (2008).
Bodine et al., Synthesis of readily modifiable cyclodextrin analogues via cyclodimerization of an alkynyl-azido trisaccharide, J. Am. Chem. Soc., 126(6):1638-9 (2004).

(Continued)

*Primary Examiner* — Gina C Justice
(74) *Attorney, Agent, or Firm* — Scheinberg & Associates, PC

(57) ABSTRACT

The invention generally relates to the field of drug delivery. In particular, the invention relates to amphiphilic dendron-coils, micelles thereof and their use for the transdermal delivery of drugs.

35 Claims, 34 Drawing Sheets

(56) References Cited

OTHER PUBLICATIONS

Bouwstra et al., Structure of the skin barrier and its modulation by vesicular formulations, Prog. Lipid Res., 42(1):1-36 (2003).

Bruls et al., Transmission of human epidermis and stratum corneum as a function of thickness in the ultraviolet and visible wavelengths, Photochem. Photobiol., 40(4):485-94 (1984).

Cevc et al., Lipid vesicles and other colloids as drug carriers on the skin, Adv. Drug Deliv. Rev., 56(5):675-711 (2004).

Chen et al., A precise packing sequence for self-assembled convex structures, Proc. Natl. Acad. Sci. USA, 104(3):717-22 (2007).

Cho et al., Mesophase structure-mechanical and ionic transport correlations in extended amphiphilic dendrons, Science, 305(5690):1598-601 (2004).

Christensen et al., Additivity and the physical basis of multivalency effects: a thermodynamic investigation of the calcium EDTA interaction, J. Am. Chem. Soc., 125(24):7357-66 (2003).

Day et al., Health-related quality of life and tamoxifen in breast cancer prevention: a report from the National Surgical Adjuvant Breast and Bowel Project P-1 Study, J. Clin. Oncol., 17(9):2659-69 (1999).

Ewald, Die berechnung optischer and elektrostischer gitterpotentiale, Ann. Phys., 64:253-87 (1920). [German only].

Finnin et al., Transdermal penetration enhancers: applications, limitations, and potential, J. Pharm. Sci., 88(10):955-8 (1999).

Forrest et al., In vitro release of the mTOR inhibitor rapamycin from poly(ethylene glycol)-b-poly(epsilon-caprolactone) micelles, J. Control. Release, 110(2):370-7 (2006).

Gaucher et al., Block copolymer micelles: preparation, characterization and application in drug delivery, J. Control. Release, 109(1-3):169-88 (2005).

Ge et al., Responsive supramolecular gels constructed by crown ether based molecular recognition, Angew. Chem. Int. Ed. Engl., 48(10):1798-802 (2009).

Gestwicki et al., Selective immobilization of multivalent ligands for surface plasmon resonance and fluorescence microscopy, Anal. Biochem., 305(2):149-55 (2002).

Ghosh et al., Ranking of aqueous surfactant-humectant systems based on an analysis of in vitro and in vivo skin barrier perturbation measurements, J. Cosmet. Sci., 58(6):599-620 (2007).

Ghosh et al., Why is sodium cocoyl isethionate (SCI) mild to the skin barrier?—An in vitro investigation based on the relative sizes of the SCI micelles and the skin aqueous pores, J. Cosmet. Sci., 58(3):229-44 (2007).

Gillies et al., Designing Macromolecules for Therapeutic Applications: Polyester DendrimerPoly(ethylene oxide) "Bow-Tie" Hybrids with Tunable Molecular Weight and Architecture, J. Am. Chem. Soc., 124(47):14137-46 (2002).

Gillies et al., Stimuli-Responsive Supramolecular Assemblies of Linear-Dendritic Copolymers, J. Am. Chem. Soc., 126(38):11936-43 (2004).

Gjerde et al., Tissue distribution of 4-hydroxy-N-desmethyltamoxifen and tamoxifen-N-oxide, Breast Cancer Res. Treat., 134(2):693-700 (2012).

Goetz et al., The impact of cytochrome P450 2D6 metabolism in women receiving adjuvant tamoxifen, Breast Cancer Res. Treat., 101(1):113-21 (2007).

Guillard et al., Molecular interactions of penetration enhancers within ceramides organization: a FTIS approach, Eur. J. Pharm. Sci., 36(2-3):192-9 (2009).

Harada et al., Supramolecular assemblies of block copolymers in aqueous media as nanocontainers relevant to biological applications, Prog. Polymer Sci., 31(11):949-82 (2006).

Hendradi et al., Effect of mixed micelle formulations including terpenes on the transdermal delivery of diclofenac, Biol. Pharm. Bull., 26(12):1739-43 (2003).

Hong et al., Covalent immobilization of p-selectin enhances cell rolling, Langmuir, 23(14):12261-8 (2007).

Hong et al., Interaction of poly(amidoamine) dendrimers with supported lipid bilayers and cells: hole formation and the relation to transport, Bioconjug. Chem., 15(4):774-82 (2004).

Hong et al., Interaction of polycationic polymers with supported lipid bilayers and cells: nanoscale hole formation and enhanced membrane permeability, Bioconjug. Chem., 17(3):728-34 (2006).

Hong et al., The binding avidity of a nanoparticle-based multivalent targeted drug delivery platform, Chem. Biol., 14(1):107-15 (2007).

Hua et al., Versatile strategy for the synthesis of dendronlike polypeptide/linear poly(epsilon-caprolactone) block copolymers via click chemistry, Biomacromolecules, 10(5):1140-8 (2009).

Humphrey et al., VMD: Visual molecular dynamics, J. Mol. Graphics, 1491):33-8 (1996).

International Preliminary Report on Patentability, International Application No. PCT/US2014/017762, dated Aug. 25, 2015.

International Search Report and Written Opinion, International Application No. PCT/US14/17762, dated May 14, 2014.

Israelachvili et al., Theory of self-assembly of hydrocarbon amphiphiles into micelles and bilayers, J. Chem. Soc. Faraday Trans 2, 72:1525-68 (1976).

Israelachvili, Intermolecular and Surface Forces, San Diego: Academic Press Inc. (1995).

Jain et al., Self assembling polymers as polymersomes for drug delivery, Curr. Pharm. Des., pp. 1-15 (2011).

Joralemon et al., Shell Click-Crosslinked (SCC) Nanoparticles: A New Methodology for Synthesis and Orthogonal Functionalization, J. Am. Chem. Soc., 127(48):16892-9 (2005).

Kajimoto et al., Noninvasive and persistent transfollicular drug delivery system using a combination of liposomes and iontophoresis, Int. J. Pharm., 403(1-2):57-65 (2011).

Karande et al., Design principles of chemical penetration enhancers for transdermal drug delivery, Proc. Natl. Acad. Sci. USA, 102(13):4688-93 (2005).

Kellermann et al., The first account of a structurally persistent micelle, Angew. Chem. Int. Ed. Engl., 43(22):2959-62 (2004).

Kim et al., Methoxy poly(ethylene glycol) and epsilon-caprolactone amphiphilic block copolymeric micelle containing indomethacin. II. Micelle formation and drug release behaviours, J. Control. Release, 51(1):13-22 (1998).

Kitov et al., On the nature of the multivalency effect: a thermodynamic model, J. Am. Chem. Soc., 125(52):16271-84 (2003).

Kong et al., Quantifying the relation between adhesion ligand-receptor bond formation and cell phenotype, Proc. Natl. Acad. Sci. USA, 103(49):18534-9 (2006).

Kostiainen et al., High-affinity multivalent DNA binding by using low-molecular-weight dendrons, Angew. Chem. Int. Ed. Engl., 44(17):2556-9 (2005).

Kostiainen et al., Precisely defined protein-polymer conjugates: construction of synthetic DNA binding domains on proteins by using multivalent dendrons, ACS Nano, 1(2):103-13 (2007).

Kratzat et al., Influence of the Molecular Geometry of Nonionic Surfactants on Surface and Micellar Properties in Aqueous Solutions, Langmuir, 12(7):1765-70 (1996).

Lee et al., In vitro human skin permeation of endoxifen: potential for local transdermal therapy for primary prevention and carcinoma in situ of the breast, Breast Cancer: Targets and Therapy, 3:61-70 (2011).

Lee et al., Molecular Dynamics Studies of Polyethylene Oxide and Polyethylene Glycol: Hydrodynamic Radius and Shape Anisotropy, Biophysical J., 95(4):1590-9 (2008).

Lee et al., Temperature-triggered reversible micellar self-assembly of linear-dendritic block copolymers, Chem. Commun. (Camb.), 32:3726-8 (2008).

Leonenko et al., Investigation of temperature-induced phase transitions in DOPC and DPPC phospholipid bilayers using temperature-controlled scanning force microscopy, Biophys. J., 86(6):3783-93 (2004).

Leroueil et al., Nanoparticle interaction with biological membranes: does nanotechnology present a Janus face?, Acc. Chem. Res., 40(5):335-42 (2007).

(56) References Cited

OTHER PUBLICATIONS

Liu et al., In vivo fate of unimers and micelles of a poly(ethylene glycol)-block-poly(caprolactone) copolymer in mice following intravenous administration, Eur. J. Pharm. Biopharm., 65(3):309-19 (2007).

Low et al., Discovery and development of folic-acid-based receptor targeting for imaging and therapy of cancer and inflammatory diseases, Acc. Chem. Res., 41(1):120-9 (2008).

Lu et al., Aggregation behavior of Mpeg-Pcl diblock copolymers in aqueous solutions and morphologies of the aggregates, J. Polymer Sci. Polymer Phys., 44:3406-17 (2006).

MacKerell et al., All-Atom Empirical Potential for Molecular Modeling and Dynamics Studies of Proteins, J. Phys. Chem. B, 102(18):3586-616 (1998).

Mah et al., A miniaturized flow-through cell to evaluate skin permeation of endoxifen, Int. J. Pharm., 441(1-2):433-40 (2013).

McNerny et al., RGD dendron bodies; synthetic avidity agents with defined and potentially interchangeable effector sites that can substitute for antibodies, Bioconjug. Chem., 20(10):1853-9 (2009).

Mitragotri, Modeling skin permeability to hydrophilic and hydrophobic solutes based on four permeation pathways, J. Control. Release, 86(1):69-92 (2003).

Moghimi et al., Investigating the potential of non-thermal microwave as a novel skin penetration enhancement method, Int. J. Pharm., 401(1-2):47-50 (2010).

Myung et al., Dendrimer-mediated multivalent binding for the enhanced capture of tumor cells, Angew. Chem. Int. Ed. Engl., 50(49):11769-72 (2011).

Nagarajan, Molecular Packing Parameter and Surfactant Self-Assembly: The Neglected Role of the Surfactant Tail, Langmuir, 18(1):31-8 (2002).

Nagrath et al., Isolation of rare circulating tumour cells in cancer patients by microchip technology, Nature, 450(7173):1235-9 (2007).

Nandivada et al., Click Chemistry: Versatility and Control in the Hands of Materials Scientists, Adv. Mater., 19(17):2197-208 (2007).

Oerlemans et al., Polymeric micelles in anticancer therapy: targeting, imaging and triggered release, Pharm. Res., 27(12):2569-89 (2010).

Papp et al., Inhibition of influenza virus infection by multivalent sialic-acid-functionalized gold nanoparticles, Small, 6(24):2900-6 (2010).

Parker et al., Folate receptor expression in carcinomas and normal tissues determined by a quantitative radioligand binding assay, Anal. Biochem., 338(2):284-93 (2005).

Pearson et al., Dendritic nanoparticles: the next generation of nanocarriers?, Ther. Deliv., 3(8):941-59 (2012).

Pearson et al., Facilitated self-assembly of novel dendron-based copolymers, Conf. Proc. IEEE Eng. Med. Biol. Sci., 2011:8334-6 (2011).

Pearson et al., Positively Charged Dendron Micelles Display Negligible Cellular Interactions, ACS Macro Lett., 2(1):77-81 (2013).

Peer et al., Nanocarriers as an emerging platform for cancer therapy, Nat. Nanotechnol., 2(12):751-60 (2007).

Philips et al., Scalable molecular dynamics with NAMD, J. Computational Chem., 26:1781 (2005).

Poree et al., Synthesis of amphiphilic star block copolymers and their evaluation as transdermal carriers, Biomacromolecules, 12(4):898-906 (2011).

Port et al., Patient reluctance toward tamoxifen use for breast cancer primary prevention, Ann. Surg. Oncol., 8(7):580-5 (2001).

Posocco et al., Morphology prediction of block copolymers for drug delivery by mesoscale simulations, J. Mater. Chem., 20:7742-53 (2010).

Potts et al., Predicting skin permeability, Pharm. Res., 9(5):663-9 (1992).

Pozo-Guisado et al., The antiproliferative activity of resveratrol results in apoptosis in MCF-7 but not in MDA-MB-231 human breast cancer cells: cell-specific alteration of the cell cycle, Biochem. Pharmacol., 64(9):1375-86 (2002).

Prausnitz et al., Current status and future potential of transdermal drug delivery, Nat. Rev. Drug Discov., 3(2):115-24 (2004).

Qiu et al., Polymer architecture and drug delivery, Pharm. Res., 23(1):1-30 (2006).

Rae et al., CYP2D6 genotype should not be used to determine endocrine therapy in postmenopausal breast cancer patients, Clin. Pharmacol. Ther., 94(2):183-5 (2013).

Riley et al., Physicochemical Evaluation of Nanoparticles Assembled from Poly(lactic acid)-Poly(ethylene glycol) (PLA-PEG) Block Copolymers as Drug Delivery Vehicles, Langmuir, 17(11):3168-74 (2001).

Riva et al., Combination of Ring-Opening Polymerization and "Click Chemistry": Toward Functionalization and Grafting of Poly(?-caprolactone), Macromolecules, 40(4):796-803 (2007).

Rosen et al., Dendron-mediated self-assembly, disassembly, and self-organization of complex systems, Chem. Rev., 109(11):6275-540 (2009).

Rouanet et al., Neoadjuvant percutaneous 4-hydroxytamoxifen decreases breast tumoral cell proliferation: a prospective controlled randomized study comparing three doses of 4-hydroxytamoxifen gel to oral tamoxifen, J. Clin. Oncol., 23(13):2980-7 (2005).

Shah et al., Skin penetration enhancement—clinical pharmacological and regulatory considerations, IN: Walters et al. (eds.), Pharmaceutical Skin Penetration Enhancement, pp. 417-427, CRC Press (1993).

Sheu et al., Influence of micelle solubilization by tocopheryl polyethylene glycol succinate (TPGS) on solubility enhancement and percutaneous penetration of estradiol, J. Control. Release, 88(3):355-68 (2003).

Sigma-Aldrich, "Nanomaterials Dendrons" (Oct. 30, 2008).

Spernath et al., Phosphatidylcholine embedded micellar systems: enhanced permeability through rat skin, J. Colloid Interface Sci., 318(2):421-9 (2008).

Subedi et al., Recent advances in transdermal drug delivery, Arch. Pharm. Res., 33(3):339-51 (2010).

Suek et al., Computer simulation of architectural and molecular weight effects on the assembly of amphiphilic linear-dendritic block copolymers in solution, Langmuir, 24(7):3030-41 (2008).

Sun et al., Biodegradable micelles with sheddable poly(ethylene glycol) shells for triggered intracellular release of doxorubicin, Biomaterials, 30(31):6358-66 (2009).

Sutton et al., Functionalized micellar systems for cancer targeted drug delivery, Pharm. Res., 24(6):1029-46 (2007).

Tanford, The Hydrophobic Effect: Formation of Micelles and Biological Membranes, New York: Wiley Sons (1973).

Tian et al., Vesicular self-assembly of comb-dendritic block copolymers, Chem. Commun. (Camb.), 33:3489-91 (2006).

Tong et al., Nanopolymeric micelle effect on the transdermal permeability, the bioavailability and gene expression of plasmid, Mol. Pharm., 9(1):111-20 (2012).

Turco Liveri et al., Peculiar mechanism of solubilization of a sparingly water soluble drug into polymeric micelles. Kinetic and equilibrium studies, J. Phys. Chem. B, 116(16):5037-46 (2012).

Urbani et al., Self-Assembly of Amphiphilic Polymeric Dendrimers Synthesized with Selective Degradable Linkages, Macromolecules, 41(1):76-86 (2008).

Vanommeslaeghe et al., CHARMM general force field: A force field for drug-like molecules compatible with the CHARMM all-atom additive biological force fields, J. Comput. Chem., 31(4):671-90 (2010).

Venuganti et al., Effect of poly(amidoamine) (PAMAM) dendrimer on skin permeation of 5-fluorouracil, Int. J. Pharm., 361(1-2):230-8 (2008).

Verma et al., Particle size of liposomes influences dermal delivery of substances into skin, Int. J. Pharm., 258(1-2):141-51 (2003).

Ward, Mechanical Properties of Solid Polymers, New York: John Wiley and Sons (1971).

Whitesides et al., Molecular self-assembly and nanochemistry: a chemical strategy for the synthesis of nanostructures, Science, 254(5036):1312-9 (1991).

Wilheim et al., Poly(styrene-ethylene oxide) block copolymer micelle formation in water: a fluorescence probe study, Macromolecules, 24(5):1033-40 (1991).

(56) References Cited

OTHER PUBLICATIONS

Williams et al., Penetration enhancers, Adv. Drug Deliv. Rev., 56(5):603-18 (2004).
Wiradharma et al., Self-assembled polymer nanostructures for delivery of anticancer therapeutics, Nanotoday, 4(4):302-17 (2009).
Wu et al., The tamoxifen metabolite, endoxifen, is a potent antiestrogen that targets estrogen receptor alpha for degradation in breast cancer cells, Cancer Res., 69(5):1722-7 (2009).
Yang et al., Aggregation behavior of self-assembling polylactide/poly(ethylene glycol) micelles for sustained drug delivery, Int. J. Pharm., 394(1-2):43-9 (2010).
Yang et al., Effect of size, surface charge, and hydrophobicity of poly(amidoamine) dendrimers on their skin penetration, Biomacromolecules, 13(7):2154-62 (2012).
Yang et al., Nanoscale polymeric penetration enhancers in topical drug delivery, Polym. Chem., 4:2651-7 (2013).
Yang et al., Synthesis, self-assembly, and in vitro doxorubicin release behavior of dendron-like/linear/dendron-like poly(epsilon-caprolactone)-b-poly(ethylene glycol)-b-poly(epsilon-caprolactone) triblock copolymers, Biomacromolecules, 10(8):2310-8 (2009).
Yoo et al., Biodegradable polymeric micelles composed of doxorubicin conjugated PLGA-PEG block copolymer, J. Control. Release, 70(1-2):63-70 (2001).
Yoshimoto et al., Binding enhancement of antigen-functionalized PEGylated gold nanoparticles onto antibody-immobilized surface by increasing the functionalized antigen using alpha-sulfanyl-omega-amino-PEG, Chem. Commun. (Camb.), 42:5369-71 (2008).
Zhou et al., Micellization of amphiphilic star polymers with poly-(ethylene oxide) arms in aqueous solutions, Langmuir, 9(11):2907-13 (1993).

* cited by examiner

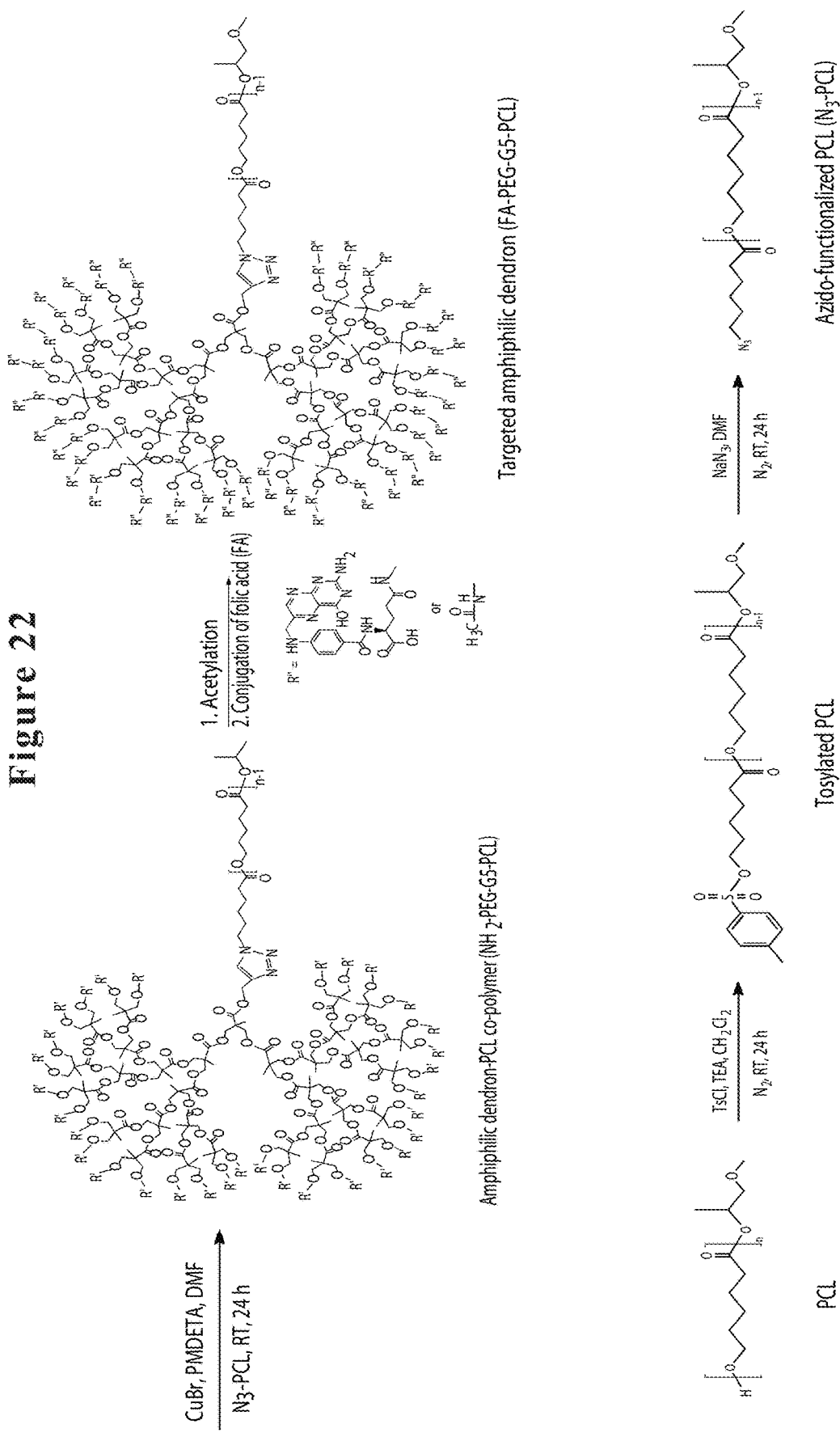
Figure 22 1 of 2

DERMAL DRUG DELIVERY USING AMPHIPHILIC DENDRON-COIL MICELLES

CROSS-REFERENCE TO RELATED APPLICATIONS

This application is a Continuation of U.S. application Ser. No. 14/769,704 filed Aug. 21, 2015, which is a U.S. National Phase of International Application No. PCT/US14/17762 filed Feb. 21, 2014, which claims the priority benefit under 35 U.S.C. § 119(e) of U.S. Provisional Application No. 61/767,902, filed Feb. 22, 2013, the disclosure of which is incorporated herein by reference in its entirety.

FIELD OF THE INVENTION

The invention generally relates to the field of drug delivery. In particular, the invention relates to amphiphilic dendron-coils, micelles thereof and their use for the transdermal delivery of drugs.

BACKGROUND

Endoxifen (4-hydroxy-N-desmethyl tamoxifen or EDX) is known to be responsible for the overall effectiveness of tamoxifen in treating ER-positive breast cancer as it is a primary active metabolite of the prodrug tamoxifen converted by the cytochrome P450 2D6 (CYP2D6) isoform[62,63]. For this reason, women diagnosed with genetically impaired CYP2D6 activity have been found to have a higher propensity for breast cancer recurrence upon tamoxifen treatment[64] Oral administration of EDX would be a way to treat those women lacking CYP2D6; however, the orally taken and thus systemically exposed EDX has been reported to induce numerous side effects such as hot flashes, vaginal atrophy, endometrial cancer and thromboembolic events {Gjerde, 2012 #313}[65-68]. In order to address these issues, the present invention contemplates the local, transdermal delivery of EDX to the breast by topical administration, which would minimize the systemic exposure of the drug[69], thereby potentially reducing the side effects from oral tamoxifen/EDX.

For EDX to be effectively delivered through the skin layers, the molecules must go through a multi-layered barrier. In particular, the stratum corneum (SC) is the most significant barrier that needs to be overcome to effectively deliver drugs by the topical route[70]. EDX is a highly hydrophobic small molecule with a partition coefficient (log P) of 6.01 at 25° C.[71]. As this log P value is far beyond the optimum range (between 1 and 3)[72-76] for efficient skin permeation, EDX itself cannot be efficiently translocated through the skin layer without the use of penetration enhancers[77].

Chemical penetration enhancers (CPEs), such as ethanol and sodium dodecyl sulfate (SDS), have been commonly used to enhance the skin permeability of therapeutic molecules that are otherwise skin impermeable[74]. However, significant irritation and adverse effects have been often observed because of skin dehydration and/or SC lipid disruption, which is typically proportional to penetration enhancement abilities[74,78]. To overcome the problem of skin irritation, polymeric micelles have been introduced as potential platforms for transdermal drug delivery due to their small size, skin permeability, biocompatibility, high drug and gene adaptability, and tunable surface functionality and release profiles[79-83]. Polymeric micelles are small, spherical particles (<200 nm in diameter) made up of polymer chains. The polymer chains of polymeric micelles are block copolymers (i.e., typically linear polymers that are composed of repeating blocks of two polymers that differ in hydrophilicity, charge or polarity). Some block copolymers that are amphiphilic block copolymers self-assemble into micelles when placed in an appropriate solvent. A few types of polymeric micelles prepared from monomethoxy poly (ethylene glycol)-poly(s-caprolactone) (MPEG-PCL) copolymers {Xue, 2012 #270}, poly(ethylene oxide)-poly(propylene oxide)-poly(ethylene oxide) block copolymers and methoxy-poly(ethylene glycol)-hexyl substituted polylactide block copolymers have been reported to be used for transdermal drug delivery of oridonin (anticancer), econazole nitrate (antifungal), and plasmids (with 3-galactosidase gene), respectively.

Self-assembled polymeric micelles have nanostructural features, such as their thermodynamic stability, size, and shape of self-assemblies, that can be widely manipulated depending on both amphiphilicity of materials and fabrication techniques. Self-assembly is a process in which a stable ordered ensemble of molecules is formed through the balancing of attractive and repulsive forces between amphiphiles at a concentration above the critical micelle concentration (CMC).[1] One of the most promising types of block copolymers capable of self-assembling is the dendron-coil (DC),[2] A DC is comprised of a flexible linear polymer dendronized at one end in which amphiphilicity can be engineered through the appropriate choice of hydrophilic and hydrophobic blocks. The highly branched, controlled molecular architecture of the dendron allows the unique properties of dendrimers such as monodispersity, precise control of peripheral functional groups, and multivalency to be integrated.[3]

Many groups have reported amphiphilic DCs and other dendron-based copolymers capable of self-assembling into a wide variety of morphologies.[2] Particularly, amphiphilic DCs containing a single hydrophobic peptide block and multiple hydrophilic blocks combined through mediation by a dendron have been shown to preferentially self-assemble into spherical micelles with sizes less than 100 nm.[4]

Over the past decade, significant advances have been made in the development of polymeric micelles to treat and detect cancer effectively[5] and various design strategies have been implemented to enhance cancer targeting.[6,7] The hydrophilic-lipophilic balance (HLB) between polymer chains is a crucial factor used to describe the self-assembly behavior of polymers and is strongly associated with the degree of micellar dissociation and blood circulation time augmenting the enhanced permeability and retention (EPR) effect. In addition, by controlling the HLB it has been shown that a variety of morphologies can be induced (e.g. vesicular, spherical, cylindrical micelles) via self assembly as a result of the interplay between thermodynamic forces.[8] A well-defined density of targeting ligands on the surface and their adopted geometry are also important to produce enhanced selective binding to cancer tissues as supported by recent studies on multivalent cancer targeting.[9,10] In this regard, a dendron, a segment of a dendrimer, is a unique material that not only retains the properties of its parent dendrimer (symmetry and monodispersity) but through distinctive chemical modifications of its focal point and periphery can be hybridized with other materials to create amphiphilic structures that self-assemble and exhibit unique biological responses[11].

In Oerlemans et al. 2010[5], the authors review research and clinical trials on polymeric micelles in anticancer therapy. In Table 1 on page 2571, the review article reports that five micelle products for anticancer therapy had been investigated in clinical trials, one of which (Genexol-PM) has been granted FDA approval to be used in patients with breast cancer. In Table VII on page 2583, the review article lists various multifunctional micellar formulations, including a EGF-receptor-targeted PEG-b-PCL micelles labeled with $^{111}$In and a micellar formulation consisting of folate-conjugated PEG-b-PCL loaded with doxorubicin and SPIONS, that combine two or more the functions of targeting ligands, imaging agents and triggered release. At the end of its "Conclusion and Future Perspectives" section on page 2583, the authors state that "the versatility of micelle-based drug delivery and the large number of promising preclinical studies describing numerous approaches to optimize these nanomedicines will bring the development of a magic bullet a major step forward. Now it is time to bring this potential into clinical practice."

Thus, there exists in the art a need for products and methods for the transdermal delivery of drugs to target cells.

SUMMARY

The present invention provides methods of transdermal delivery of a drug (or drugs) to a patient by topcially administering to the patient a composition comprising a micelle, where the drug has a molecular weight over 500 g/mol, a 1-octanol/PBS partition coefficient (log P) less than 1 or greater than 3, or both. In the methods, the micelle comprises amphiphilic dendron-coils and encapsulates the drug, and each amphiphilic dendron-coil comprises a hydrophobic core-forming block, a polyester dendron and a poly(ethylene) glycol (PEG) moiety.

In some embodiments, the micelle also comprises one or more ligands conjugated to one or more PEG moieties.

In some embodiments, the micelle further comprises a chemical penetration enhancer.

In some embodiments, the drug is a hydrophobic drug.

In some embodiments, the drug is a cancer drug. In some embodiments, the cancer drug is endoxifen (EDX).

Micelles according to the invention comprise amphiphilic dendron-coils. In turn, each amphiphilic dendron-coil comprises a hydrophobic core-forming block, a polyester dendron and a poly(ethylene) glycol (PEG) moiety. In some embodiments, the hydrophobic core-forming block is a non-peptidyl, hydrophobic core-forming block. The non-peptidyl, hydrophobic core-forming block is a linear hydrophobic polymer, for example, a polycaprolactone (PCL), poly(lactic acid) (PLA), poly(glycolic acid) (PGA) or poly(lactic-co-glycolic acid) (PLGA). The polyester dendron is, for example, a generation 3 (G3) to generation 5 (G5) polyester dendron with either an acetylene or carboxylate core. The PEG moiety is, for example, a methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide-activated PEG (PEG-NHS) moiety, NH$_2$-PEG-NH$_2$ moiety or NH$_2$-PEG-COOH moiety. The micelles comprising amphiphilic dendron-coils are also referred to as "multivalent dendron conjugates" and "dendron-based nanomicelles (DNMs)" at various places in the Examples herein. The invention also provides the amphiphilic dendron-coils.

In some embodiments, the micelles comprise amphiphilic dendron-coils comprising poly(E-caprolactone) (PCL), G3 polyester dendron and PEG-carboxyl moieties, and the micelles both encapsulateEDX and bear EDX on their surface. In some embodiments, the micelles comprise amphiphilic dendron-coils comprising poly(E-caprolactone) (PCL), G3 polyester dendron and PEG-amine moieties, and the micelles both encapsulateEDX and bear EDX on their surface. In some embodiments, the micelles comprise amphiphilic dendron-coils comprising poly(E-caprolactone) (PCL), G3 polyester dendron and PEG-acetamide moieties, and the micelles both encapsulateEDX and bear EDX on their surface. Drug loading percentages of the micelles can be about 0.1% to about 30%, about 0.1% to about 20%, about 0.1 to about 10%, about 0.1% to about 6%, or about 0.1% to about 3%.

The polyester dendron is covalently modified with the linear hydrophobic polymer to help to facilitate chain entanglement and intramolecular interactions which aid in the self-assembly of core-shell type micelles and enable hydrophobic drug molecules to be loaded within the micelles.

Biologically important properties such as biodegradability, targetability, and drug release can be controlled by varying the three components (also referred to as the three polymer blocks) of the amphiphilic dendron-coils. Moreover, the copolymer structure is flexible and can be easily manipulated by varying the molecular weights of each component to fine-tune the hydrophilic-lipophilic balances (HLBs). For example, various embodiments of the invention employ PCL, polyester dendron, and PEG with molecular weights ranging 0.5-20 kDa, G3-G5 (~0.9-3.5 kDa), and 0.2-5 kDa, respectively. The HLBs (20 $M_H/(M_H+M_L)$, where $M_H$ is the mass of the hydrophilic block and $M_L$ is the mass of the lipophilic block) therefore widely vary from 2.22 to 19.94.

The micelles also exploit the unique structural benefits of their dendron components. Unlike linear polymers, a dendron offers multiple surface groups enabling multivalent interactions with other molecules including, for example, one or more drugs.

When a dendron is co-polymerized with the hydrophobic linear polymer [such as polycaprolactone (PCL), poly(lactic acid) (PLA), poly(glycolic acid) (PGA), and poly(lactic-co-glycolic acid) (PLGA)] in generation of the amphiphilic dendron-coils of the invention, the cone-shaped, amphiphilic dendron-coils in turn possess advantageous structural attributes because they form self-assembled micelles, which are thermodynamically favorable and have highly packed PEG surface layers. The thermodynamic stability in forming micelles, along with the unique architecture that is easily tunable, make the amphiphilic dendron-coils and their self-assembled micellar structures ideal for use as a drug delivery platform.

BRIEF DESCRIPTION OF THE DRAWINGS

FIGS. 12A-12E show MD simulation results for single (Panel a) PCL3.5K-mPEG2K, (Panel b) PC3.5K-mPEG16K and (Panel c) PCL3.5K-G3-mPEG2K monomers in water. (Panel d) PCL3.5K-mPEG2K micelle (number of monomers=128) and (Panel e) PCL3.5K-G3-mPEG2K micelle (number of monomers=14). PEG is shown in grey; PCL in white/black. Water is not shown for clarity. Scale bar=5 nm.

DETAILED DESCRIPTION

Figure 1:
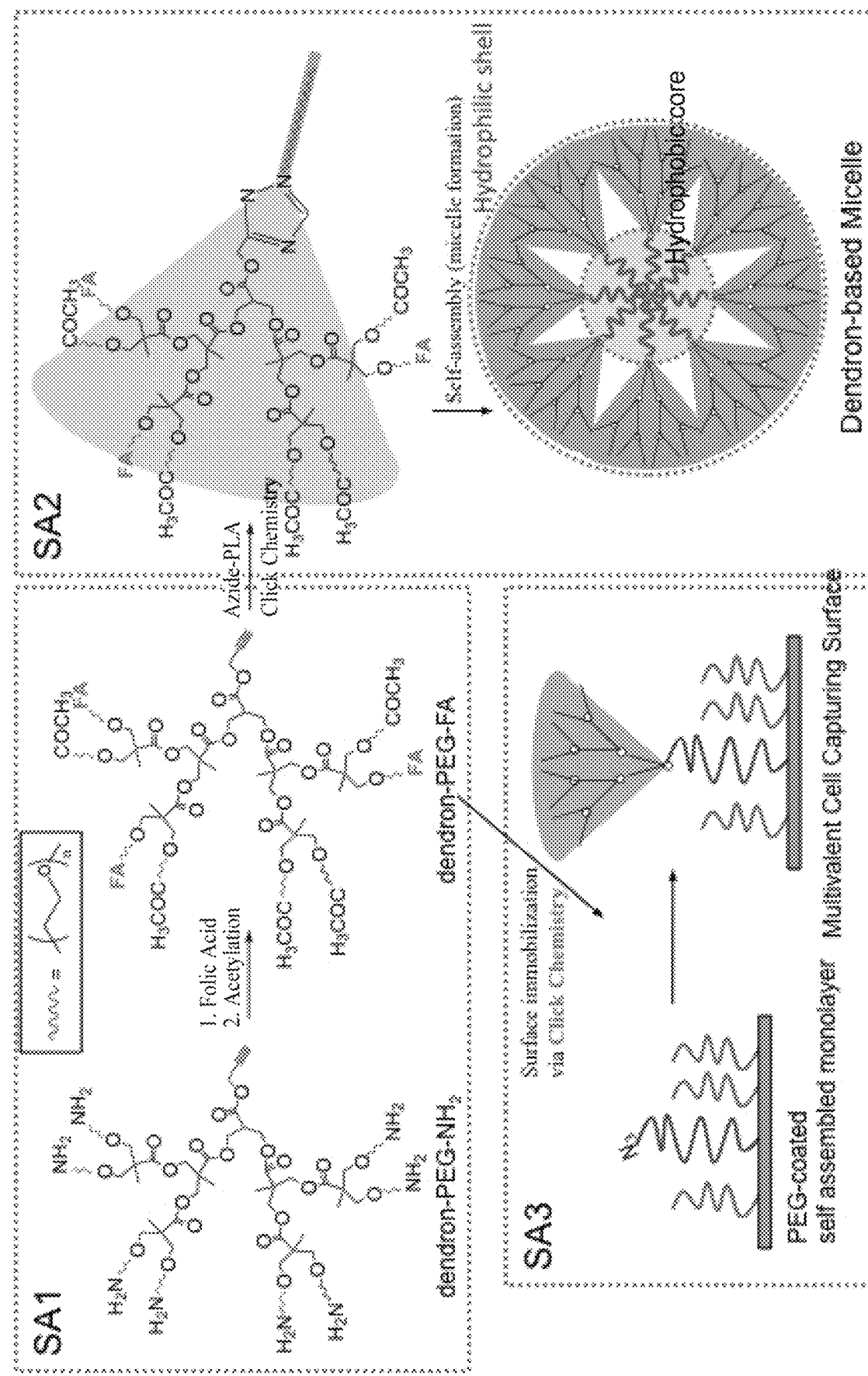
FIG. 1 shows a general overview of exemplary folic acid-conjugated amphiphilic dendron-coils and uses thereof.

In an aspect, the invention provides methods of transdermal delivery of a drug to a patient comprising administering to the patient a topical composition comprising a micelle and a pharmaceutically acceptable excipient, wherein the drug has a molecular weight over 500 g/mol, a 1-octanol/PBS partition coefficient (log P) less than 1 or greater than 3, or both, and wherein the micelle comprises amphiphilic dendron-coils and encapsulates the drug, and wherein each amphiphilic dendron-coil comprises a non-peptidyl, hydrophobic core-forming block, a polyester dendron and a poly(ethylene) glycol (PEG) moiety.

"Transdermal delivery" herein is intended to encompass both transdermal (or "percutaneous" or "dermal") and transmucosal administration, i.e., delivery by passage or penetration of a drug through the skin or mucosal tissue. In some embodiments, the drug does not enter the bloodstream. In some embodiments, the drug enters the bloodstream.

In some embodiments of the methods, the transdermal delivery of a drug is "prolonged" or "sustained," that is the all drug is not delivered upon contact with the skin or mucosal tissue, but the drug is released over a period of at least one, at least two, at least three, at least four, at least five, at least six, at least seven, at least eight, at least nine, at least ten, at least fifteen or more days. Biphasic drug delivery/release is also contemplated wherein there is an initial release of drug (for example, off the surface of the micelle) and then a continuing release of drug (for example, release of drug encapsulated in the micelle).

The term, "flux" (also called "permeation rate") is defined as the absorption of the drug through the skin or mucosa, and is described by Fick's first law of diffusion: $J=-D(dCm/dx)$, where J is the flux in g/cm$^2$/sec, D is the diffusion coefficient of the drug through the skin or mucosa in cm$^2$/sec and dCm/dx is the concentration gradient of the drug across the skin or mucosa. In some embodimenets, the flux achieved is at least about 5 g/cm$^2$/sec; at least about 7 g/cm$^2$/sec; at least about 10 g/cm$^2$/sec; at least about 20 g/cm$^2$/sec; at least about 30 g/cm$^2$/sec; at least about 40 g/cm$^2$/sec; at least about 45 g/cm$^2$/sec; at least about 50 g/cm$^2$/sec; at least about 60 g/cm$^2$/sec; at least about 65 g/cm$^2$/sec; at least about 70 g/cm$^2$/sec; at least about 100 g/cm$^2$/sec; at least about 150 g/cm$^2$/sec; or at least about 155 g/cm$^2$/sec; or more.

In some embodiments of the methods, the micelles themselves are "non-permeating," that is they are not absorbed through the skin or mucosa in quantities that contribute in a statistically significant amount to the transdermal delivery of the drug.

Micelles used in the methods comprise amphiphilic dendron-coils. The amphiphilic dendron-coils each comprise three components: a non-peptidyl, hydrophobic core-forming block, a polyester dendron and a poly(ethylene) glycol (PEG) moiety. The hydrophobic core-forming block of the micelles is non-peptidyl, that is, the hydrophobic core-forming block is not a peptide. In some embodiments of the invention, a micelle comprises a single type of amphilphilic dendron-coil (i.e., the amphiphilic dendron-coils in the micelle all have the same three components.) In some embodiments of the invention, a micelle comprises more than one type of amphiphilic dendron-coil (i.e., the amphiphilic dendon-coils in the micelle vary in their three components.)

In some embodiments, the non-peptidyl, hydrophobic core-forming block of the amphiphilic dendron-coil comprises polycaprolactone (PCL), poly(lactic acid) (PLA), poly(glycolic acid) (PGA) or poly(lactic-co-glycolic acid) (PLGA). In some embodiments, the non-peptidyl, hydrophobic core-forming block is PCL. In some embodiments, the PCL is poly(ε-caprolactone). In some embodiments, the non-peptidyl, hydrophobic core-forming block is PLA. In some embodiments, the non-peptidyl, hydrophobic core-forming block is PGA. In some embodiments, the non-peptidyl, hydrophobic core-forming block is PLGA. The non-peptidyl, hydrophobic core-forming block has a molecular weight including, but not limited to, a molecular weight from about 0.5 kDa to about 20 kDa. In some embodiments, the non-peptidyl, hydrophobic dore-forming block is poly(ε-caprolactone) with a molecular weight of about 3.5 kDa. In some embodiments, the non-peptidyl, hydrophobic dore-forming block is poly(ε-caprolactone) has a molecular weight of 14 kDa. In some embodiments, the amphiphilic dendron-coils those disclosed in Example 2.

In some embodiments, the polyester dendron of the amphiphilic dendron-coil includes, but is not limited to, a generation 3 to generation 5 [that is, a generation 3 (G3), a generation 4 (G4) or a generation 5 (G5)] polyester dendron with either an acetylene or carboxylate core. In some embodiments, the polyester dendron is a G3 dendron. In some embodiments, the polyester dendron is a G5 dendron. In some embodiments, the polyester dendron has an acetylene core. In some embodiments, the polyester dendron is generation 3 polyester-8-hydroxyl-1-acetylene bis-MPA dendron. In some embodiments, the polyester dendron has a carboxylate core. Methods of preparing and characterizing dendrons are well known in the art, and various polyester dendrons useful in the invention may be purchased from commercial entitites.

In some embodiments, the PEG moiety of the amphiphilic dendron-coil is a methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide activated PEG (PEG-NHS) moiety, NH$_2$-PEG-NH$_2$ moiety or NH$_2$-PEG-COOH moiety. In some embodiments, the PEG moiety has a molecular weight including, but not limited to, a molecular weight from about 0.2 kDa to about 5 kDa. In some embodiments, the PEG moiety is mPEG moiety. In some embodiments, the PEG moiety is an mPEG moiety with a molecular weight of about 2 kDa. In some embodiments, the PEG moiety is an mPEG moiety with a molecular weight of about 5 kDa.

The micelles encapsulate or, in other words, are loaded with one or more drugs. In some embodiments of the methods, a single drug is encapsulated by the micelle. In some embodiments, at least two drugs are encapsulated by the micelle. In some embodiments, one or more drugs are present on the surface of the micelle. Any drug that can be loaded in the micelle is contemplated for transdermal delivery by methods of the invention. In some embodiments, the drug is a hydrophobic drug. Exemplary drugs contemplated by the invention are discussed in more detail below.

In some embodiments, the drug is a cancer drug (i.e., a drug used to treat cancer), used interchangeably with anti-cancer drug. In some embodiments, the drug is an anti-inflammatory drug including, but not limited to, indomethacin. In some embodiments, the drug is α-mangostin. The drug α-mangostin has been reported to have antioxidant, anti-bacterial, anti-cancer/anti-tumor and anti-allergy properties. In some embodiments, the drug is endoxifen.

A "drug" is a compound that, upon administration to a patient (including, but not limited to, a human or other animal) in a therapeutically effective amount, provides a therapeutic benefit to the patient. Those skilled in the art will appreciate that the term "drug" is not limited to drugs that have received regulatory approval.

Drugs contemplated by the invention include, but are not limited to, small organic molecules, RNA, DNA, proteins, chemicals or peptides to block transcription, translation, intracellular signaling cascades, enzymes (kinases), proteosome activity, lipid metabolism, cell cycle, and membrane trafficking. Drugs include agents that target proinflammatory mediators such as cytokine and chemokine genes, enzymes involved in generation of inflammatory mediators, receptors for cytokines, chemokines, lipid mediators, apoptosis, cytoplasmic signaling molecules involved in inflammatory cascades, e.g., NF-κB, STAT, Talin, Rap-1; tissue injury such as apoptosis, e.g., caspase, bcl-2; molecules important for cell activation and proliferation, e.g., cyclins, kinesin Eg5; molecules important for cell movement/migration/invasion, e.g., small G-proteins, cytoskeletal proteins; and oncogenes. Specific targeting of CD4 with a drug may also be used for blocking HIV infection. Moreover, specific targeting of Ku70 may be used for killing or suppressing cancer cells and specific targeting of Cyclin-Dl may be used for blocking proliferation. Other exemplary drugs contemplated for blocking proliferation include chemotherapy agents set out below.

In addition, drugs for treating diseases such as viral diseases are also contemplated by the present invention. One example of such a drug is an siRNA which serves as a virocide. This is useful for treatment and/or prevention of HSV, HPB and HIV. Such therapeutic agents are described in PCT/US2006/021758 and PCT/US2003/034424, each of which are incorporated by reference in their entirety. Antiviral therapeutics also include viral entry inhibitors, viral assembly inhibitors, viral DNA and RNA polymerase inhibitors, viral reverse transcriptase inhibitors, viral protease inhibitors, viral integrase inhibitors, and inhibitors of viral shedding.

In some embodiments, the drug is a chemotherapy agent. Such agents include, e.g., cancer drugs such as paclitaxel, methotrexate, doxorubicin, cisplatin, carboplatin; estrogen receptor (ER) antagonists such as, tamoxifen and its metabolites (e.g., 4-hydroxytamoxifen and endoxifen), and fulvestrant; and anti-angiogenesis agents such as canstatin, proliferin-related proteins, restin, maspin, osteopontin, Secreted Protein Acidic and Rich in Cysteine (SPARC) protein, Vascular Endothelial cell Growth Inhibitor (VEGI), prolactin, prothrombin, Interferon (IFN)-alpha, IFN-beta, IFN-gamma, C-X-C motif chemokine 10 (CXCL10), Interleukin (IL)-4, IL-12, metalloprotease and Thrombospondin domains protein (METH)-1 and METH-2, Tissue Inhibitors of metalloproteinase (TIMP), cell division autoantigen 1 (CDA1), platelet factor-4, vasostatin, calreticulin, endostatin, angiostatin, thrombospondin (TSP)-1 and TSP-2, Angiopoietin 2, Vascular Endothelial Growth Factor Receptor (VEGFR)-1, and Novel SH2-containing Protein 1 (NSP-1). Other chemotherapeutic agents include, but are not limited to, a Transforming Growth Factor Beta (TGFβ) inhibitor, a gamma-type Peroxisome Proliferator-Activated Receptor (PPARγ) ligand, an angiotensin activity inhibitor, a Platelet-Derived Growth Factor (PDGF) inhibitor, a sodium channel inhibitor, and an apoptosis inducer. In some embodiments, the drug is endoxifen.

The amount of drug present in the micelle can vary over a wide range. The drug can be about 25% to about 75% (weight/weight) of the total mass of the micelle (wherein the mass of the drug is included in the total mass of the micelle). In some embodiments, the drug can be about 30% to about 60% w/w of the total mass of the micelle (same basis). In some embodiments, the drug can be about 40% to about 70% w/w of the total mass of the micelle (same basis).

In some embodiments, the micelles of the invention comprise one or more ligands conjugated to one or more PEG moieties. Ligands contemplated by the invention are discussed in more detail below. In some embodiments, the ligand is folic acid.

The term "ligand" refers to a compound that exhibits selectivity for a particular target organ, tissue or cell. A ligand is capable of binding to the particular target organ, tissue, or cell. As with the drug that may be loaded in a micelle, various ligands may be used in the micelles, compositions and methods herein. In some embodiments, the ligand binds a cancer cell. One example of a ligand is the vitamin folic acid (FA), which binds folate receptors that are overexpressed in ~90% of human ovarian carcinomas.

Luteinizing hormone-releasing hormone (LHRH) is another suitable ligand. LHRH is relatively small molecule (MW 1,182 Da), with the receptors overexpressed by breast, ovarian, and prostate cancer cells. As another example, the ligand is a retinoid such as retinol, retinal, retinoic acid, rexinoid, or derivatives or analogs thereof. Further examples of ligands include, but are not limited to, transferrin, RGD peptide, Herceptin, prostate-specific membrane antigen (PSMA)-targeting aptamers, follicle stimulating hormone (FSH), epidermal growth factor (EGF) and the like. Other ligands include various antibodies such as anti-CD19, anti-CD20, anti-CD24, anti-CD33, anti-CD44, Lewis-Y antibody, sialyl Lewis X antibody, LFA-1 antibody, rituximab, bevacizumab, anti-VEGF mAb, and their fragments, dimers, and other modified forms. In other embodiments, the ligand targets an immune cell. For targeting immune cells, the ligand can be a ligand of e.g., a T cell surface receptor. Lectins can be used as ligands to target mucin and the mucosal cell layer. Lectins of use in the invention include those isolated from *Abrus precatroius, Agaricus bisporus, Glycine max, Lysopersicon esculentum, Mycoplasma gallisepticum*, and *Naja mocambique*, as well as lectins such as Concanavalin A and Succinyl-Concanavalin A.

In some embodiments, the ligand increases the selective delivery of the micelle to a particular target organ, tissue or cell. In some embodiments, the increase in selective delivery may be at least about two-fold as compared to that of an otherwise comparable composition lacking the targeting agent. In some embodiments, the delivery of the micelle containing a ligand to the target organ, tissue or cell is increased by at least 10% compared to that of an otherwise comparable composition lacking the ligand. In some embodiments, the delivery of the micelle to the target organ, tissue or cell is increased by at least 25% or more as compared to that of an otherwise comparable composition lacking the ligand.

The amount of ligand present in a micelle can vary over a wide range. In some embodiments, the ligand can be about 1% to about 50% (weight/weight) of the total mass of the micelle (wherein the mass of the ligand is included in the total mass of the nanocore). In other embodiments, the ligand may be about 10% to about 30% w/w of the total mass of the micelle (same basis). In still other embodiments, the ligand may be about 20% to about 40% w/w of the total mass of the micelle (same basis).

In some embodiments, the ligands may be conjugated to the micelle through a covalent bond to PEG. A variety of mechanisms known to those skilled in the art can be used to form the covalent bond between the ligands and PEG, e.g., a condensation reaction. Additional methods for directly bonding one or more ligands to PEG are known to those skilled in the art, and may be identified by routine experimentation informed by the guidance provided herein. As is known to the skilled artisan, chemistries include, but are not limited to, thioether, thioester, malimide and thiol, amine-carboxyl, amine-amine, and others listed in organic chemistry manuals, such as, Elements of Organic Chemistry, Isaak and Henry Zimmerman Macmillan Publishing Co., Inc., New York, N.Y. Ligands can also be attached to PEG using a crosslinking reagent [e.g., glutaraldehyde (GAD), bifunctional oxirane (OXR), ethylene glycol diglycidyl ether (EGDE), N-hydroxysuccinimide (NHS), and a water soluble carbodiimide, such as 1-ethyl-3-(3-dimethylaminopropyl) carbodiimide (EDC)]. The compositions herein can further have at least one hydrolysable linker between the therapeutic agent and scaffold and/or targeting agent and scaffold.

Targeting efficacy of the micelles is enhanced by harnessing both mechanisms of passive and active targeting that complement each other.

In some embodiments, the outer surface of the micelle is modified. One example of such a modification is modification of the outer surface of the micelle a cryoprotectant, e.g., a sugar, such as trehalose, sucrose, mannose, glucose or HA. The term "cryoprotectant" refers to an agent that protects a lipid particle subjected to dehydration-rehydration, freeze-thawing, or lyophilization-rehydration from vesicle fusion and/or leakage of vesicle contents.

Compositions of micelles for use in in methods of the invention comprise a pharmaceutically acceptable excipients. Such excipients include, but are not limited to, water, saline, buffered saline, dextrose, glycerol, ethanol, and combinations thereof. The formulation should suit the topical mode of administration. In some embodiments, the pharmaceutical compositions are adapted for topical administration to human beings.

In some embodiments, a composition herein is formulated in accordance with routine procedures as a pharmaceutical composition adapted for topical administration to human beings.

An "effective amount" of a composition as the term is used herein is an amount of composition comprising a drug or combination of drugs sufficient to achieve a recognized medical endpoint, e.g., a decrease in tumor size or proliferation or a decrease in the symptoms of a viral infection. amount sufficient to decrease one or more signs or symptoms of the disease or condition. Such symptoms can include, but are not limited, to a decrease in cancer cell proliferation, a decrease in tumor size, a decrease in the number of infective viral units in the subject, or a decrease in vascular leakage as determined by routine methods. Administering the composition described herein reduces signs or symptoms of the disease or condition in a subject, compared to the signs or symptoms in subject prior to administering the composition, or compared to a subject not receiving such treatment. The effective amount can be determined empirically by a skilled artisan according to established methods of measurement of relevant parameters.

As used herein, a dosing schedule refers to a protocol for administering any of the compositions as described herein, in an effective dose, administered simultaneously or within a particular interval of each other, for example, within one day of each other, or as a combined preparation, or separately, and includes the amount of the composition delivered per unit time such as per day, and the duration or period of time over which each composition is administered. A daily dose can administered as a single dose, or is divided into a plurality of smaller fractional doses, to be administered several times during the day.

The amount of the micelle of the invention which will be effective in the treatment of a particular disease or condition will depend on the nature of the disease or condition, and can be determined by standard clinical techniques. The precise dose to be employed in the formulation will also depend on the route of administration, and the seriousness of the disease or condition, and should be decided according to the judgment of the practitioner and each patient's circumstances. Effective doses may be extrapolated from dose-response curves derived from in vitro or animals or animal model test systems, by one of ordinary skill in the art of pharmacology. Dosages of the compositions to be administered to a subject are adjusted for known variations from species to species using standard data encompassing criteria for absorption, distribution, half-life kinetics in circulation, metabolism, excretion, and toxicology of the compositions of the embodiments herein. Suitable dosage ranges for administration are generally about 0.01 micrograms to about 10,000 micrograms of each active compound per kilogram body weight per day, for example, about 0.01 micrograms to about 1 microgram/kg, about 0.1 micrograms/kg to about 10 micrograms/kg, about 1 microgram/kg to about 500 micrograms/kg, or about 10 micrograms/kg to about 10 mg/kg of body weight per day. Suitable dosage ranges for administration are thus generally about 0.01 micrograms/kg body weight/day to about 10 mg/kg body weight/day.

The micelle compositions can be in a topical dosage form including, but not limited to, a liquid solution, suspension, emulsion, lotion, ointment gel, foam, paste, or powder.

Transdermal compositions are often formulated as a topical ointment or cream containing the active ingredient(s), generally in an amount ranging from about 0.01 to about 20% by weight, in some embodiments from about 0.1 to about 20% by weight, in some embodiments from about 0.1 to about 10% by weight, and in some embodiments from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

An example transdermal formulation is: stearyl alcohol (250 g) and a white petrolatum (250 g) are melted at about 75° C. and then a mixture of a dendron micelle of the of the invention, methylparaben (0.25 g), propylparaben (0.15 g), sodium lauryl sulfate (10 g), and propylene glycol (120 g) dissolved in water (about 370 g) is added and the resulting mixture is stirred until it congeals.

In one embodiment, the formulations herein can be in the form of aqueous gel, anhydrous gel, a water-in-oil emulsion, oil-in-water emulsion or a suspension. Examples of gel forming procedure for DHEA can be found in U.S. Pat. Nos. 5,709,878, and 4,978,532 the entire content of which are incorporated by reference herein. Gels are semisolid systems of either containing suspended small inorganic particles (two phase gels) or organic macromolecules interpenetrated by a liquid (single phase gels). Emollients such as petrolatum, paraffin wax, beeswax, cetyl palmitate, and lanolin can be included in the formulations herein. When formulated for presentation as a gel, the composition of the invention can include a gelling agent such as a finely divided solid and/or a thickener in concentrations that produce a loose molecular network inhibiting the free movement of liquid ingredients. Thus a typical gel composition of the invention includes a concentration of dendron micelle in the range of about 0.1 to about 20 grams per 100 grams of composition, in some embodiments about 0.25 to about 5 grams per 100 grams; a concentration of phospholipid in the range of about 2 to about 50 grams per 100 grams of composition, in some embodiments about 3 to about 25 grams per 100 milliliters; a concentration of finely divided solid in the range of about 0 to about 15 grams per 100 grams of composition, and a concentration of thickener in the range of about 0 to about 15 grams per 100 grams of composition.

Gellants may also be included in the formulations. These agents are typically non-ionic or cationic polymers such as hydroxyethyl cellulose, methylcellulose, guar gum, xanthan gum, hydroxypropylcellulose and cationic cellulosics. A particular example is Sepigel. In one embodiment, a gel comprising a dendron micelle, can be made by mixing a lower alkyl alcohol, a polysorbate, water and a dendron micelle and, optionally, adding and mixing a thickening agent followed by incubating the ingredients until gel formation. Various temperatures may be used for incubation to effect gel formation. In some embodiments, the temperature range is about 3° C. to about 90° C.; in some embodiments the range is about 10° C. to about 50° C.; and in some embodiments the range is about 10° C. to about 40° C. Incubation times vary depending on the temperature, and the ratio of ingredients. The ratios of ingredients may also vary depending on the particular therapeutic agent associated to the dendrimer within the dendron micelle and the particular lower alcohol use. The composition may comprise alcohol in the range of from about 20 to about 95% (v/v); in some embodiments from about 30 to about 90%; in some embodiments from about 50 to about 90%. The water content may from about 0 to about 60%; in some embodiments about 2 to about 40%; in some embodiments about 5 to about 30%; in some embodiments about 15 to about 30%. The surfactant may be present in the range of about 0 to 10%; in some embodiments about 0.01% to about 5%; in some embodiments about 0.01% to about 3.5%.

Examples of thickening agents that can be added to the gel or solution formulations described herein include: cellulosic thickening agents, for example, cellulose, hydroxyethylcellulose, carboxymethylcellulose, and hydroxypropylmethyl-cellulose; and acrylic thickening agents. Examples of acrylic thickeners are carbomers, for example, non-linear polymers of acrylic acid cross-linked with a polyalkenyl polyether. Examples of carbomers which may be used in the present invention include carboxypolymethylene, carboxyvinyl polymer, and alkyl acrylates, for example, acrylic acid/alkyl methacrylate copolymer. All of the above are available from Noveon, with carboxypolymethylene sold as Carbopol 980 carboxyvinyl polymer sold as Carbopol 940, and acrylic acid/alkyl methacrylate copolymer sold as Pemulen TR-1.

In some embodiments, the formulations of the invention can be applied by misting or spraying the formulation on the skin either via a metered dose device or from a unit dose container. In this method, the formulation can be distributed evenly over a larger area thereby providing a quick means for absorption. Alternatively the formulation can be applied via an applicator, such as a roll-on applicator, a metered pump dispenser or sponge.

A topical oil-in-water emulsion composition can be prepared by making a solution of fluasterone (or related compound) as described above and adding an immiscible phase (e.g., a biocompatible oil phase) and an optional emulsifying agent. An irritation mitigating agent can also be included, such as $C_{12-15}$ alkyl benzoate, octyl methoxycinnamate, octyl dimethyl PABA, octocrylene, menthyl anthranilate, and homomenthyl salicylate.

In certain embodiments a foam comprising compounds of instant application can be prepared. An example of a foam forming procedure can be found in U.S. Pat. No. 7,141,237. For instance, an active agent in a solution as described herein and a quick-breaking foaming agent comprising a mixture of cetyl alcohol and stearyl alcohol, which are dissolved in the ethanol solution can be used. This composition can be packaged in a polyamide-imide-lined aluminum can and pressurized with a propane/butane mixture as the propellant. Under the packaged pressure, the hydrocarbon propellant liquefies and becomes miscible with the water/ethanol solution.

The formulation herein may contain an emulsifier and/or surfactant. A wide variety of such agents can be employed. In one embodiment, the compositions of the present invention comprise from about 0.05% to about 95%, in some embodiments from about 10% to about 80%, and in some embodiments from about 3.5% to about 60% of at least one surfactant. The surfactant, at a minimum, must be hydrophilic enough to disperse in ethanol or other solvent system. The surfactants useful herein can include any of a wide variety of cationic, anionic, zwitterionic, and amphoteric surfactants disclosed in prior patents and other references. The exact surfactant chosen will depend upon the pH of the composition and the other components present.

In one embodiment, the composition comprises a hydrophilic emulsifier or surfactant. In some embodiments, the compositions of the present invention comprise from about 0.05% to about 5%, in some embodiments from about 0.05% to about 3.5% of at least one hydrophilic surfactant. Without intending to be limited by theory, it is believed that the hydrophilic surfactant assists in dispersing hydrophobic materials.

Hydrophilic surfactants are selected from nonionic surfactants. Among the nonionic surfactants that are useful herein are those that can be broadly defined as condensation products of long chain alcohols, e.g. C8-30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Examples of these surfactants include those wherein S is a glucose moiety, R is a C8-20 alkyl group, and n is an integer of from about 1 to about 9. Commercially available examples of these surfactants include decyl polyglucoside and lauryl polyglucoside.

Other useful nonionic surfactants include the condensation products of alkylene oxides with fatty acids (i.e. alkylene oxide esters of fatty acids); the condensation products of alkylene oxides with 2 moles of fatty acids (i.e. alkylene oxide diesters of fatty acids); the condensation products of alkylene oxides with fatty alcohols (i.e. alkylene oxide ethers of fatty alcohols); and the condensation products of alkylene oxides with both fatty acids and fatty alcohols. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof. Commercially available surfactants include polysorbate 80 (Tween 80), polysorbate 20 (Tween 20), polysorbate 40 (Tween 40) and polysorbate (60). In some embodiments, the surfactants include polysorbates and in some embodiments the surfactant is Tween 80.

The dendron micelles and compositions of this invention can also be administered by a transdermal device. Accordingly, transdermal administration can be accomplished using a patch either of the reservoir or porous membrane type, or of a solid matrix variety.

A device, or individual dosage unit, of the present invention can be produced in any manner known to those of skill in the art. After the dermal composition is formed, it may be brought into contact with the backing layer in any manner known to those of skill in the art. Such techniques include calender coating, hot melt coating, solution coating, etc. Of course, backing materials are well known in the art and can comprise plastic films of polyethylene, vinyl acetate resins, ethylene/vinyl acetate copolymers, polyvinyl chloride, polyurethane, and the like, metal foils, non-woven fabric, cloth and commercially available laminates. The backing material generally has a thickness in the range of 2 to 1000 micrometers and the dermal composition is generally disposed on backing material in a thickness ranging from about 12 to 250 micrometers thick.

Suitable release liners are also well known in the art and include the commercially available products of Dow Corning Corporation designated Bio-Release. liner and Syl-off7 7610 liner. For embodiments in which a polysiloxane is part of the multiple polymeric adhesive carrier, the release liner must be compatible with the silicone adhesive. An example of a suitable commercially available liner is 3M's 1022 Scotch Pak. The configuration of the transdermal delivery system of the present invention can be in any shape or size as is necessary or desirable. Illustratively, a single dosage unit may have a surface area in the range of 1 to 200 $cm^2$. In some embodiments, sizes are from 5 to 60 $cm^2$.

In some embodiments, where the carrier is a flexible, finite polymer, one or more polymers are blended, optionally with PVP to result in a pressure-sensitive adhesive composition, or transdermal drug delivery system adhesive system (with incorporated parent drug:prodrug), which controls delivery of an incorporated parent drug:prodrug and through the epidermis. In some embodiments of the invention, a transdermal drug delivery system is prepared by mixing a soluble PVP, polyacrylate, polysiloxane, parent drug/prodrug, optional enhancer(s), co-solvent(s), and tackifying agents, if needed, in an appropriate volatile solvent(s), then casting the mixture and removing the solvent(s) by evaporation to form a film. Suitable volatile solvents include, but are not limited to, alcohols such as isopropanol and ethanol; aromatics such as xylenes and toluene; aliphatics such as hexane, cyclohexane, and heptane; and alkanoic acid esters such as ethyl acetate and butyl acetate.

Included are delivery systems for transdermal administration by: passive patches, heated passive patches, passive patches applied onto RF treated skin, and spray-on-skin systems where the total amount applied is fixed and delivery is improved by co-formulated permeation enhancers.

In some embodiments, the composition is administered to the recipient by means of a transdermal delivery system or patch. Transdermal delivery is accomplished by exposing a source of the substance to be administered to the recipient's skin for an extended period of time. Typically, the formulation is incorporated in or absorbed on a matrix or container from which it is released onto the recipient's skin. The rate of release can be controlled by a membrane placed between the container and the skin, by diffusion directly from the container, or by the skin itself serving as a rate-controlling barrier. Many suitable transdermal delivery systems and containers therefore are known, ranging in complexity from a simple gauze pad impregnated with the substance to be administered and secured to the skin with an adhesive bandage to multilayer and multi-component structures. Some of the systems are characterized by the use with the substance to be administered of a shaped article sufficiently flexible to snugly fit to the skin of the recipient and thus serve both as container from which the substance is delivered to the recipient's skin and as barrier to prevent loss or leakage of the substance away from the area of the skin to which the substance is to be delivered. A transdermal delivery system or patch may also contain an added substance that assists the penetration of the active ingredient through the skin, usually termed a skin enhancer or penetration enhancer. Transdermal delivery systems may contain an ethoxylated oil such as ethoxylated castor oil, ethoxylated jojoba oil, ethoxylated corn oil, and ethoxylated emu oil. An alcohol mixed with the ethoxylated oil may form a penetration enhancer.

One advantage of transdermal systems is an ability to provide a sustained release of medication over time, which may serve to provide a longer duration of action. However, a significant limitation and disadvantage of passive transdermal administration is a slow onset of sufficient action to provide relief. It is not uncommon for a passive transdermal patch to take several hours (3 or more) before a therapeutic dosage is achieved. With passive transdermal delivery, the skin can act as a depot, and release to the bloodstream will not occur until that skin depot area is saturated. This slow onset of action acts as a clinical limitation in two respects: 1) it cannot replace an existing oral or injectable form because it is a necessity to apply a patch several hours prior to a chemotherapy or operative procedure, and 2) a slow acting transdermal patch cannot reasonably serve as a rescue medication form, where a patient will prefer, for obvious reasons, a faster acting treatment. This second limitation is significant, in that it has been shown that, in many cases of highly emetogenic therapies, such as high dose chemotherapy, a significant percentage of patients will not be adequately served by a first, primary dosage form alone.

A more rapid onset of action can be achieved transdermally by using a system that includes iontophoresis. Granisetron in its hydrochloride salt form, is positively charged and can be delivered rapidly from a positively charged anode pad. Recent reports, for example, Scientific Abstract 1: Evaluation of iontophoretic permeation kinetics of granisetron through skin by subcutaneous microdialysis, presented at the 2003 AAPS meeting October, 2003; Scientific Abstract 2: IVIVC of Iontophoretic Delivery of granisetron by subcutaneous microdialysis, presented at the 2004 AAPS meeting October, 2004, have demonstrated that with iontophoresis, a therapeutic dosage can be achieved (in a hairless rat animal model) within approximately two-hours.

Other mechanical methods of enhancement and delivery of pharmaceutical drugs transdermally include: physical therapy (e.g., massage), electroporation, transdermal patches, implantable release devices/microchips, microneedle injection arrays, needleless injection devices, chemical or physical skin peels (microdermabrasion), magnetophoresis, and laser-radiation photomechanical wave devices.

The invention also provides for transdermal delivery systems wherein the dendron micelle is administered in combination with liposomes, niosomes or elastic vesicles such as transferosomes or ethosomes. Ethosomes are phospholipid-based elastic nanovesicles containing a high content of ethanol. Ethanol is known as an efficient penetration enhancer and has been added in the vesicular system to prepare elastic nanovesicles. It can interact with the polar head group region of the lipid molecules, resulting in the reduction of the melting of the stratum corneum lipid, thereby increasing lipid fluidity and cell membrane permeability. Transfersomes possess an infrastructure consisting of hydrophobic and hydrophilic moieties together and as a result can accommodate drug molecules with wide range of solubility. Transfersomes can deform and pass through narrow constriction (from 5 to 10 times less than their own diameter) without measurable loss. Transferosomes were designed in an attempt to concentrate the drug in tissues of interest, while reducing amount of drug in the remaining tissues.

In some embodiments, transdermal delivery methods of the invention utilize a carrier. The term "carrier" or "vehicle" as used herein refers to carrier materials suitable for transdermal administration, and include any such materials known in the art, e.g., any liquid, gel, solvent, liquid diluent, solubilizer, hydrogel, paraffin, wax, oil, silicone, ester, oily cream, aqueous cream, water soluble base, glycerol, glycol, lotion, powder or microemulsion, polymer or the like, which is nontoxic and which does not significantly interact with other components of the composition or the skin in a deleterious manner. The carrier is present in an amount sufficient to achieve its function of carrying the dendron micelle. In some embodiments, the carrier is present in an amount ranging from 2 to 99 wt %, in some embodiments 30 to 90 wt %, or in some embodiments 40 to 80 wt %.

In some embodiments, carriers are flexible, finite compositions. The phrase "flexible, finite system" is intended to mean a solid form capable of conforming to the surface with which it comes into contact, and which is capable of maintaining the contact in such solid form so as to facilitate topical application without adverse physiological response, and without being appreciably decomposed by aqueous contact during administration to a patient. In some embodiments, flexible, finite systems are polymer carriers such as pressure-sensitive adhesive matrix type in which the dendron micelle is dispersed directly in the pressure-sensitive adhesive or reservoir type carriers.

Illustrative examples of suitable adhesives as matrix type flexible, finite delivery systems include those described in U.S. Pat. No. 5,474,783. Other flexible, finite systems known in the art include films, plasters, dressings, and bandages, as well as multilayer delivery systems in which the parent drug/prodrug is solubilized or contained in one or more separate layers and reservoir-type delivery systems in which the dendron micelle is solubilized or contained in a reservoir or depot separate from the adhesive which attaches directly to the skin or mucosa.

As noted above, in some embodiments carriers are pressure-sensitive adhesive flexible, finite carriers. These can include any viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. The term pressure-sensitive adhesive also includes mixtures of different polymers and mixtures of polymers, such as polyisobutylenes (PIB), of different molecular weights, wherein each resultant mixture is pressure-sensitive. Other useful rubber based pressure-sensitive adhesives include hydrocarbon polymers such as natural and synthetic polyisoprene, polybutylene and polyisobutylene, styrene/butadiene polymers styrene-isoprene-styrene block copolymers, hydrocarbon polymers such as butyl rubber, halogen-containing polymers such as polyacrylic-nitrile, polytetrafluoroethylene, polyvinylchloride, polyvinylidene chloride, and polychlorodiene, and other copolymers thereof.

Other useful pressure-sensitive adhesives ("PSA") can include acrylic-based pressure-sensitive adhesives and silicone-based pressure-sensitive adhesives as described in U.S. Pat. Nos. 5,474,783, and 5,656,386. Suitable commercially available acrylic-based polymers can include adhesives are commercially available and include the polyacrylate adhesives sold under the trademarks Duro-Tak by National Starch and Chemical Corporation, Bridgewater, N.J., such as Duro-Tak 87-2194, Duro-Tak 87-2196, Duro-Tak 87-1197, 87-4194, 87-2510, 87-2097 and 87-2852. Other suitable acrylic-based adhesives are those sold under the trademarks Gelva-Multipolymer Solution (GMS) (Monsanto; St. Louis, Mo.), such as GMS 737, 788, 1151, 3087 and 7882.

Suitable silicone-based pressure-sensitive adhesives can include those described in Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, N.Y. (1989), incorporated by reference in its entirety. Other useful silicone-based pressure sensitive adhesives are described in the following U.S. patents: U.S. Pat. Nos. 4,591,622; 4,584,355; 4,585,836; and 4,655,767. Suitable silicone-based pressure-sensitive adhesives are commercially available and include the silicone adhesives sold under the trademarks BIO-PSA 7-4503, BIO-PSA 7-4603, BIO-PSA 7-4301, 7-4202, 7-4102, 7-4106, and BIO-PSA 7-4303 by Dow Corning Corporation, Medical Products, Midland, Mich.

The amount of the polymer carrier can range from 2 to 99 wt %, 30 to 90 wt %, or even 40 to 80 wt %.

The pressure-sensitive adhesives can be blended to modulate the solubility of the drug in the carrier system such as described in the '783 patent. In some embodiments, the multiple polymer adhesive system comprises a pressure-sensitive adhesive blend of an acrylic-based polymer, a silicone-based polymer, and a soluble PVP (described below). In some embodiments, the acrylic-based polymer and silicone-based polymer are in a ratio by weight, respectively, from about 2:98 to about 96:4, from about 2:98 to about 90:10, or from about 2:98 to about 86:14. The amount of acrylic-based (also referred to broadly as a polyacrylate) polymer and silicone-based polymer (also referred to broadly as a polysiloxane) is adjusted so as to modify the saturation concentration of the parent drug/prodrug in the ternary multiple polymer adhesive system in order to affect the rate of delivery of the parent drug/prodrug from the system and through the skin. Other useful ranges include about 5-85% by weight of the acrylate-based polymer, 10-90% by weight of polyisobutylene and 5-95% by weight of silicone-based polymer.

In some embodiments, the invention can also include a plasticizer or tackifying agent is incorporated into the formulation to improve the adhesive characteristics of the pressure-sensitive adhesive composition. Such plasticizers or tackifying agents include: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins.

The tackifying agent employed is compatible with the blend of polymers. In some embodiments, the tackifying agent is silicone fluid (e.g., 360 Medical Fluid, available from Dow Corning Corporation, Midland, Mich.) or mineral oil. Silicone fluid is useful for blends comprising polysiloxane as a major component. In other embodiments, where a synthetic rubber, for example, is a major component, mineral oil is a tackifying agent.

For parent dendron micelles which are not readily soluble in the polymer system, a co-solvent for the dendron micelle and polymer can be added. Co-solvents, such as lecithin, retinal derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the solubility of the parent drug/prodrug in the multiple polymer adhesive system.

In addition, crystallization inhibiting agents can be included in the compositions of the invention. One known agent is polyvinylpyrrolidone (PVP), in some embodiments soluble PVP as described in detail in U.S. Pat. No. 6,221,383. The term "polyvinylpyrrolidone," or "PVP" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum solubile, and Poly(1-vinyl-2-pyrrolidone). The copolymer vinyl acetate vinylpyrrolidone is known to the pharmaceutical industry as Copolyvidon, Copolyvidone, and Copolyvidonum. The term "soluble" when used with reference to PVP means that the polymer is soluble in water and generally is not substantially cross-linked, and has a molecular weight of less than about 2,000,000. The PVP usable with the present invention, in some embodiments has a molecular weight of about 2,000 to 1,100,000, in some embodiments 5,000 to 100,000, or in some embodiments 7,000 to 54,000.

The amount and type of PVP required in the foregoing embodiments will depend on the quantity and type of dendron micelle and/or therapeutic agent in the adhesive, as well as the type of adhesive, but can be readily determined through routine experimentation. Typically, the PVP is present in an amount from about 1% to about 20% by weight, or from about 3% to about 15% by weight. However, the amount of PVP can be higher than 20% for example, up to 40%, depending on the particular parent drug/prodrug used and on the desired properties of the blend. One commercially useful PVP is sold under "Kollidon," such as "Kollidon 10," "Kollidon 17 PF," "Kollidon 25," "Kollidon 90," "Kollidon 30," and "VA 64" a trademark of BASF AG, Ludwigshafen, Germany. Another useful PVP is sold under Kollidon CL-M also a trademark of BASF AG.

The compositions of this invention may further be provided with various thickeners, fillers and other additives known for use with transdermal drug delivery systems. Where the composition tends to absorb water, for example, when lecithin is used as a co-solvent, hydrophilic substances are especially useful. One type of hydrophilic substance which has been successfully employed is clay. The addition of clay has been found to improve adhesiveness in transdermal formulations without reducing the rate of parent drug/prodrug delivery. Suitable clays include aluminum silicate clay, kaolinite, montmorillonite, atapulgite, illite, bentonite, halloysite and the like.

Despite seemingly obvious advantages, local transdermal therapy (LTT) systems in cancer prevention and therapy are utilized infrequently, because of limited drug penetration through skin layers. The topmost layer of the skin, stratum corneum (SC) is a strong hydrophobic barrier to LTT and does not typically allow permeation of hydrophilic, active therapeutic molecules which have a molecular weight >500 Da. Chemical penetration enhancers (CPEs) facilitate drug delivery. Among others, oleic acid (OA) is known to be one of the most effective CPEs that can interact with intercellular lipids, thereby enhancing skin permeability 9Guillard *Eur. J. Pharm. Sci.* 36: 192-199, 2009). It has a direct fluidizing action on the alkyl chains and an indirect action on the polar head groups of the lipid bilayers, resulting in a more spacing lipid packing. However, many of CPEs are small molecules that cause significant skin toxicity and irritation. In contrast, polymeric penetration enhancers (PPEs) do not cause skin irritation but their large molecular size prevents them from penetrating deep into the skin. Thus, overcoming the skin barrier safely and effectively remains a challenge The dendron micelles or compositions of the invention can also contain agents known to accelerate the delivery of the drug through the skin. These agents have been referred to as chemical penetration enhancer, skin-penetration enhancers, accelerants, adjuvants, and sorption promoters, and are collectively referred to herein as "chemical penetration enhancers (CPE)" and are described in U.S. Pat. No. 6,221,383. CPE used in the invention include fatty acids such as oleic and linoleic acids, fatty alcohols, fatty alcohol ethers, biologics, enzymes, amines, amides, complexing agents, ionic compounds, dimetyl sulfoxide, N-methyl pyrrolidone, solvents, azones and surfactants.

For example, CPEs include polyhydric alcohols such as dipropylene glycol, propylene glycol, and polyethylene glycol which enhance parent drug/prodrug solubility; oils such as olive oil, squalene, and lanolin; fatty ethers such as cetyl ether and oleyl ether; fatty acid esters such as isopropyl myristate which enhance parent drug/prodrug diffusibility; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include ascorbic acid, panthenol, butylated hydroxytoluene, tocopherol, tocopheryl acetate, tocopheryl linoleate, propyl oleate, and isopropyl palmitate. In some embodiments, there are combinations of polyhydric alcohols such as glycerine, dipropylene glycol, butylene glycol, propylene glycol and one or more of oleyl alcohol and oleic acid.

The invention provides a pharmaceutical pack or kit comprising one or more containers filled with one or more of the ingredients of the compositions of the invention formulated for topical administration. In such a pack, or kit, can be found a container holding a micelle composition of the invention. Associated with such container (s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The transdermal delivery system of the invention will reduce the systemic exposure of drugs such as EDX and thereby reduce the adverse effects of the drug on the patient. The ease of administering the transdermal compositions comprising the dendron micelle will increase patient compliance and will have better results in preventing tumor formation and reducing the risk for developing a primary or secondary tumor.

EXAMPLES

Various aspects and advantages of the invention are illustrated in the non-limiting examples below, wherein Example 1 describes exemplary uses of materials and methods of the invention, Example 2 describes the preparation of exemplary amphiphilic dendron-coils (DCs) and encapsulation of the drug indomethacin in exemplary micelles of the invention, Example 3 describes the encapsulation of the drug α-mangostin in exemplary micelles of the invention, Example 4 describes exemplary folic acid-conjugated micelles of the invention and Example 5 describes supramolecular structures of exemplary micelles of the invention. Example 6 describes the use of exemplary micelles of the invention for the transdermal delivery of the cancer drug EDX.

Example 1

In response to the need for development of effective cancer treatments, the present invention provides two approaches: 1) cancer cell specific targeting using nanocarriers for enhanced therapeutic indices with reduced toxicity concerns and 2) selective detection and isolation of circulating tumor cells (CTCs) for diagnosis and prognosis of cancer metastasis. Both necessitate a strong, selective binding to biological targets (cell surface markers for targeting or whole cells for capturing), which may be achieved by utilizing multivalent binding. Multivalent binding properties can be engineered and fabricated using nanotechnology that allows a single versatile material to be used for multiple biomedical purposes. The present invention contemplates a nano-scale material that is useful for targeting (when formulated as a drug delivery nanocarrier) as well as capturing (when surface immobilized) cancer cells.

Multivalent binding is the simultaneous binding event of multiple ligands to multiple receptors in biological systems, which is central to a number of pathological processes, including the attachment of viral, parasitic, mycoplasmal, and bacterial pathogens. These activities can promote targeting of specific cell types. Studies with biological multivalent inhibitors have yielded quantitative measurements of binding avidities, with increases on the order of 1 to 9 orders of magnitude[15-17]. Polyamidoamine (PAMAM) dendrimers have been reported to be an excellent mediator for facilitated multivalent effect because pre-organization/orientation of ligand, polymer backbone topology, and easy deformability of the material all contribute for strong multivalent binding to cell surfaces[14]. However, PAMAM dendrimers have several drawbacks such as: 1) limited drug payloads—therapeutics can be stably carried only if chemically conjugated, and thus the number of drugs per molecule is limited by the number of the available surface functional groups and steric hindrance and 2) toxicity concerns due to non-biodegradability and intramolecular charges by tertiary amines.

The present invention instead utilizes a dendron as a platform material. A dendron is monodisperse wedge-shaped dendrimer section with multiple terminal groups and a single reactive function at the focal point. In some embodiments, the invention contemplates the use of polyester-16-hydroxyl-1-alkyne dendron as it has outstanding potential to facilitate the multivalent binding as well as to be utilized for multiple biological applications[18]. This dendron shares the advantages of a dendrimer such as: 1) chemically well-defined structure; 2) precise control over size and number of terminal functional groups; and 3) easy contol over possible chemistries such as introduction of pH-, thermo-, or enzyme-sensitive linkages to control the drug release kinetics. In addition to those advantages, this dendron uniquely provides an option of orthogonal reactions utilizing the distinct focal point and surface groups. The peripheral groups of the dendron (see FIG. 1 for chemical structure) provide multiple, well-defined reactive sites for conjugation with targeting molecules. Flexibility (conformability) of the dendron branches that are pre-organized in a relatively small area facilitates localized multivalent effect, which is expected to substantially enhance targeting/capturing efficiency of the functionalized dendron. Furthermore, amphiphilicity of dendron will be engineered by introducing a hydrophobic or hydrophilic building block to the focal point (alkyne) of dendron (see FIG. 2) through click chemistry. The enhanced targeting efficacy through engineered multivalent effect, along with the easy control over supramolecular structure, makes the dendron-based nanomaterial a novel, versatile platform.

Thus, the invention involves multiple aspects, including but not limited to, the following.

1) Preparation of Multivalent Dendron Conjugates and Optimization of Multivalent Effect.

A synthetic route for multivalent dendron conjugates is outlined in FIG. 1 (Panel SA1). Briefly, dendron (generation 4, Polyester-16-hydroxyl-1-acetylene bis-MPA dendron, Sigma-Aldrich) is modified through reaction with PEG diamine ($NH_2$-PEG-$NH_2$) to decorate the peripheral surface with primary amine groups, resulting in amine-terminated dendron (dendron-PEG-$NH_2$). A series of targeted dendron conjugates is prepared by conjugation with various amounts of a targeting molecule. In some embodiments, the targeting molecule is folic acid (FA). After conjugation of FA using 1-ethyl-3-(3-dimethylaminopropyl)carbodiimide (EDC) chemistry, the remaining amine groups are acetylated to prevent any electrostatic, non-specific interactions[14, 19-21]. FA has great potential for cancer targeting because folate receptors (FR) are overexpressed in many human carcinomas[22]. Furthermore, as a low molecular weight (MW 441) ligand, FA presumably lacks immunogenicity; still has high affinity for FR ($K_D$~$10^{-10}$ M), and defined conjugation chemistry[23]. To determine an optimal range of number of targeting molecules conjugated to the targeted dendron conjugates (dendron-PEG-FA), a series of experiments are conducted. First, extensive material characterization using NMR, FT-IR, UV/Vis, dynamic light scattering (DLS), HPL, GPC, and capillary electrophoresis (CE) are performed. Second, the surface plasmon resonance (SPR) technique using Biacore X quantifies material design-dependent binding events of dendron-PEG-FA at a molecular level, using a similar method to that previously described[14]. Optimized targeted dendron conjugates self-assemble into dendron-based nanomicelles (DNM) after further modification with a hydrophobic block (FIG. 1, Panel SA2) or immobilization on surfaces to capture target cells (FIG. 1, Panel SA3).

2) Preparation of Amphiphilic Dendrons for Micelle Formulation and In Vitro Validation of Targeting Efficacy.

Figure 2:
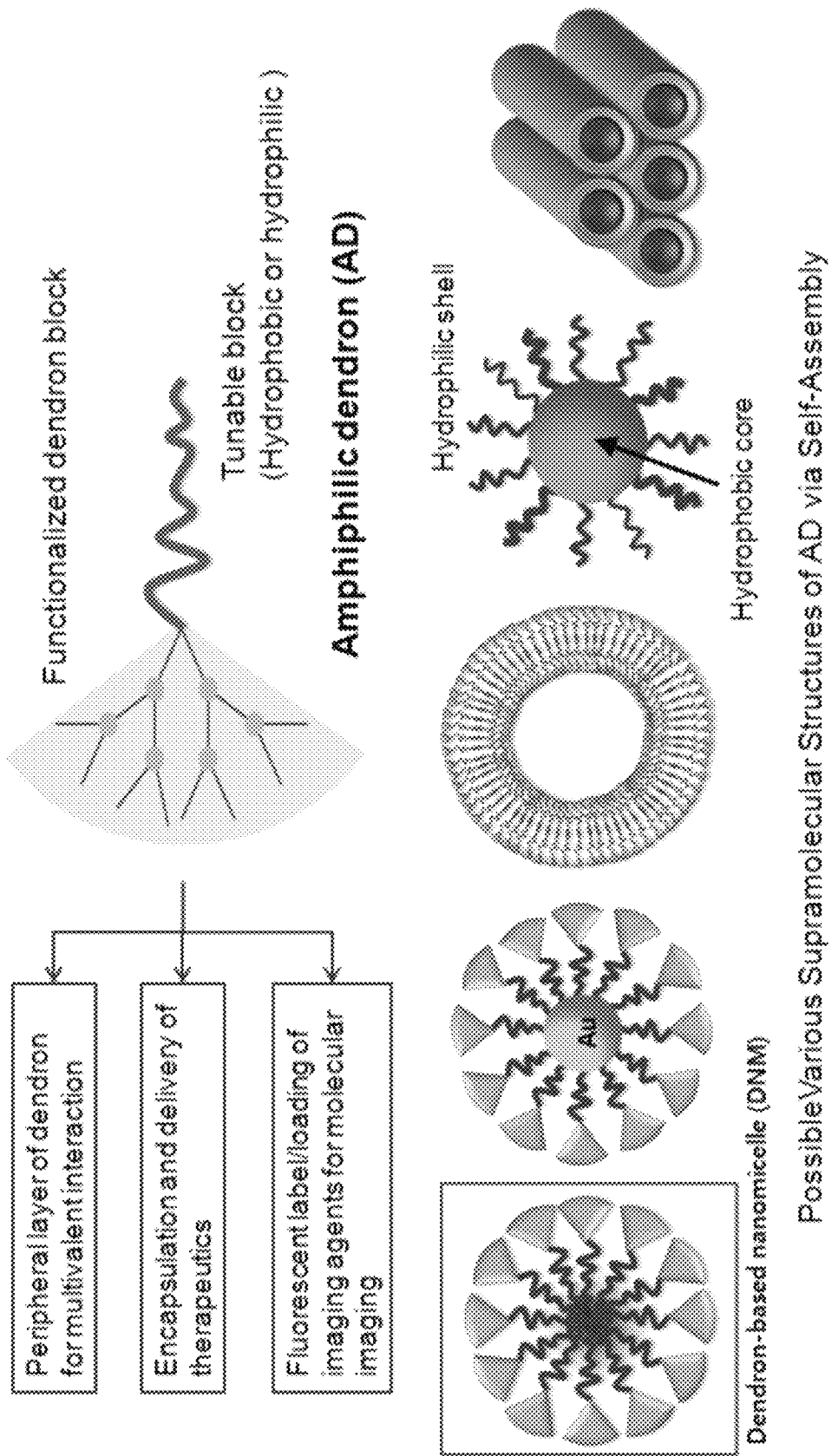
FIG. 2 shows various possible supramolecular structures of amphiphilic dendron-coils.

As illustrated in FIG. 2, the hydrophilic/hydrophobic balance between the core and dendron blocks determines supramolecular structure (e.g., sphere, vesicle, disk, or cylinder) that is formed via self-assembly of the amphiphilic molecules in a given solvent system[24]. The nano-scale structure derived from self-assembly is primarily affected by several parameters: 1) generation of the dendron; 2) size of the core; 3) relative hydrophilicity of the attached block; and 4) type of solvent used. By controlling these parameters, the morphology and size of dendron-hased nanocarriers can be manipulated. In some embodiments, DNM with a hydrophobic core [by conjugation of a lipophilic polymer block such as poly(lactic acid)] and a hydrophilic PEG outer-layer with size of 20-30 nm in diameter is anticipated to utilize both passive and active targeting for drug delivery. Fluorescence activated cell sorter (FACS), cofocal laser scanning microscopy (CLSM), and fluorescence resonance energy transfer (FRET) analyses are used to confirm the consistency of the quantitative SPR data with the in vitro results using K13 cells which FR expression can be easily regulated[14,25]. Additional FR expressing cells such as A2780, and SKOV3 cells can also be employed to test specificity of DNM.

Thus, the invention provides multivalent dendron conjugates with versatility for targeted drug delivery after formulation into DNM.

The targeted drug delivery platform exhibits enhanced targeting efficacy utilizing passive and active targeting, and enhanced drug loading capacity. The multivalent dendron-mediated binding plays a key role in enhancing the targeting efficacy of DNM. Additionally, the PEG outer-layer prolongs the blood circulation time of the DNM and minimizes systemic clearance (24), resulting in selective accumulation of DNM with precisely controlled size in tumor sites through the enhanced permeation and retention (EPR) effect.

Example 2

Figure 3:
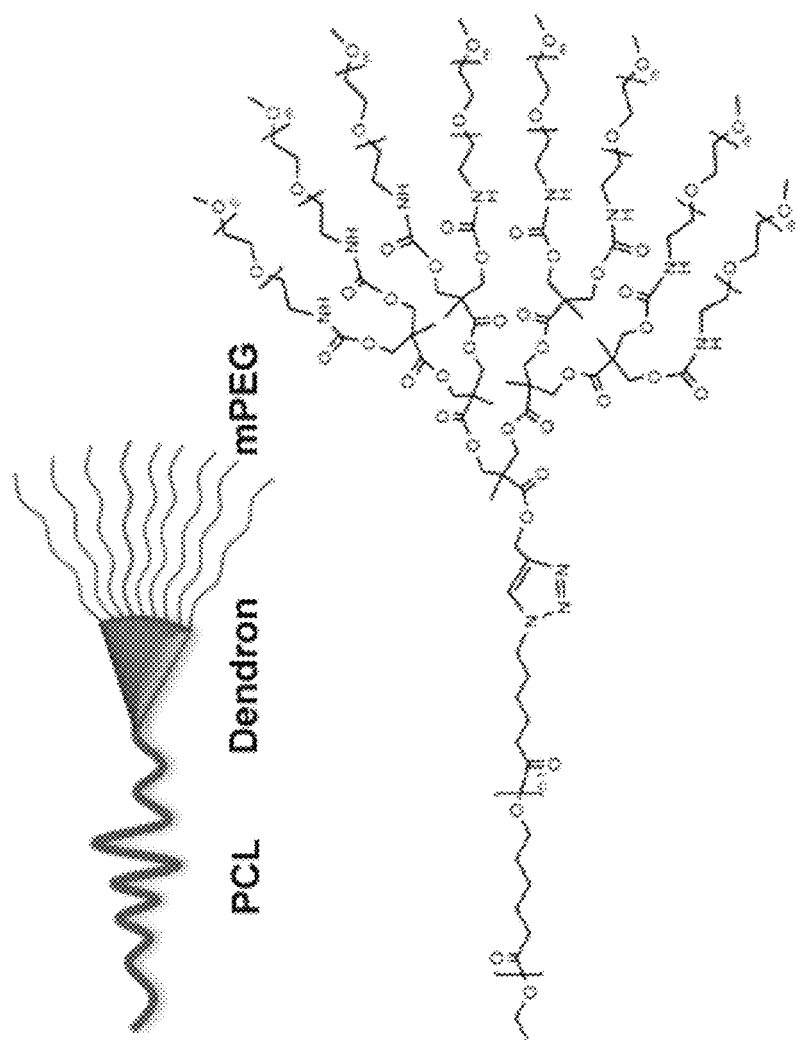
FIG. 3 shows the chemical structure of amphiphilic dendron-coils prepared through click chemistry between poly(caprolactone) (PCL), dendron and methoxy poly(ethylene glycol) (mPEG) and its self-assembled structure.
Figure 3:
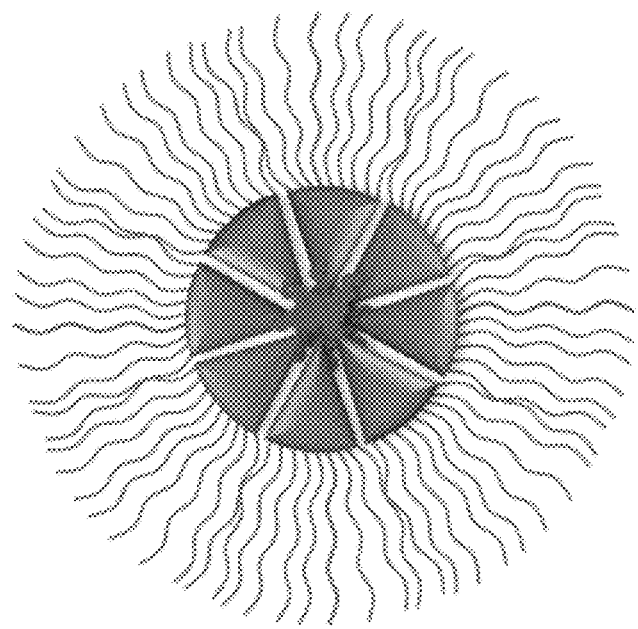

Four novel amphiphilic DCs with the general structure shown in FIG. 3, along with analogous linear-block copolymers were prepared. The amphiphilic DCs were designed with three major functional components: (1) poly(caprolactone) (PCL) as the hydrophobic core-forming block; (2) polyester G3-dendron with acetylene core to enable facile attachment of PCL by click chemistry, introduce additional molecular flexibility, to achieve a localized high density of peripheral functional groups and to mediate the combination of core- and shell-forming blocks; and (3) methoxy poly (ethylene glycol) (mPEG) to form the hydrophilic corona. In addition, two different molecular weights of PCL (PCL3.5K and PCLI4K) and mPEG (mPEG2K and mPEG5K) were used to vary HLB values of the resulting amphiphilic DCs.

Figure 4:
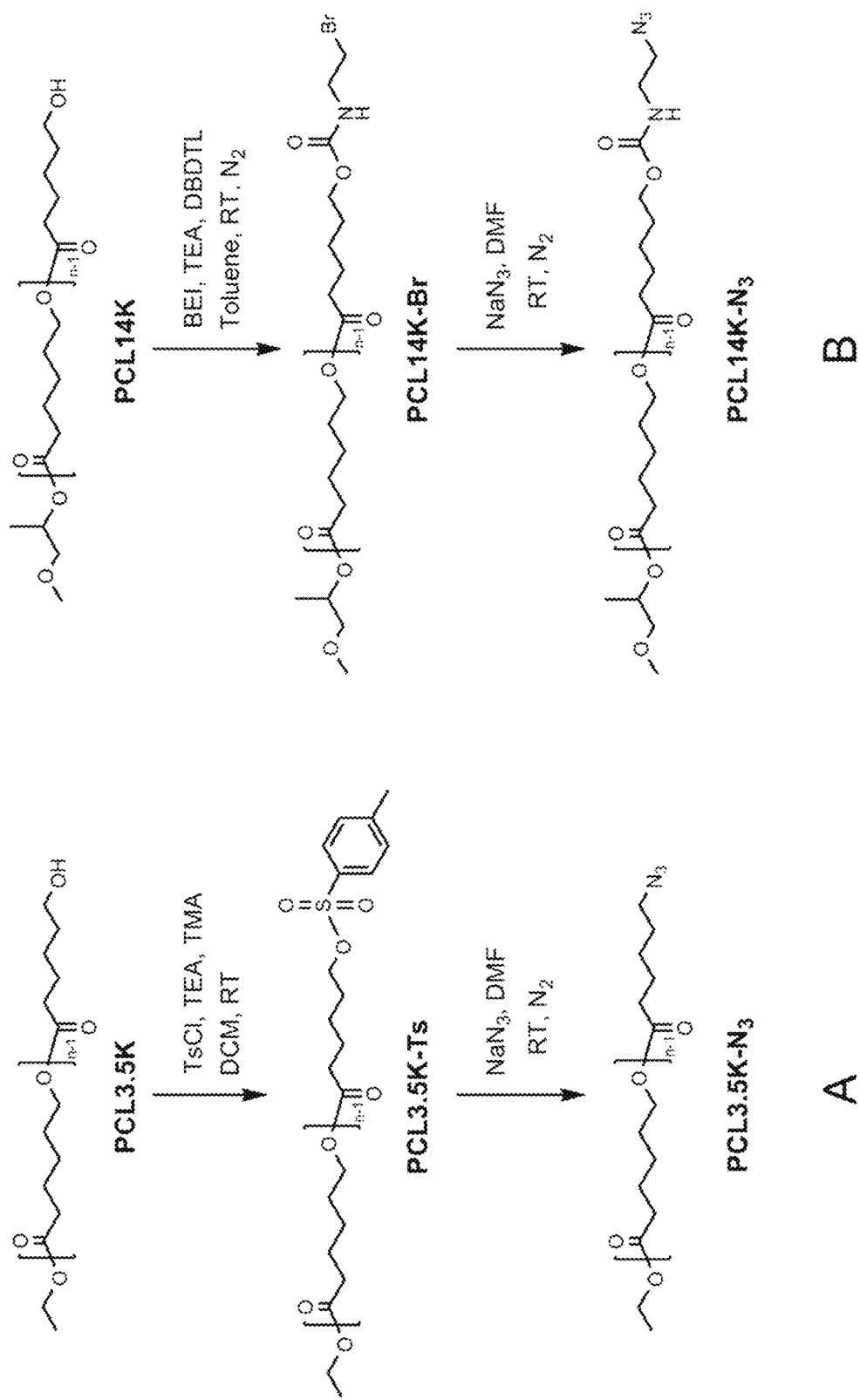
FIG. 4 shows the azido-functionalization of PCL3.5K (Panel A) and PCL14K (Panel B).
Figure 5:
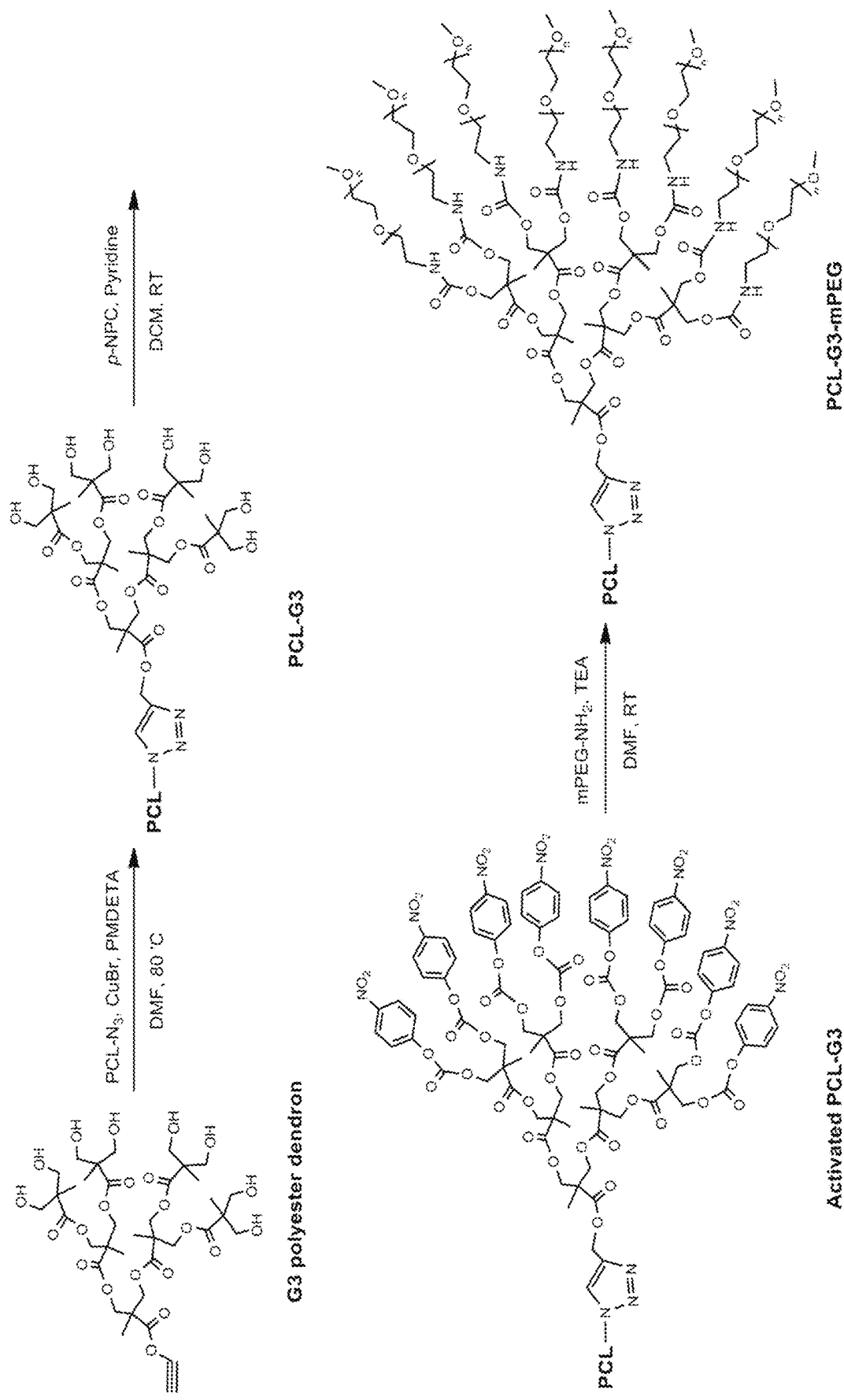
FIG. 5 shows the synthesis of PCL-G3 via click chemistry and mPEG conjugation to PCL-G3.
Figure 6A:
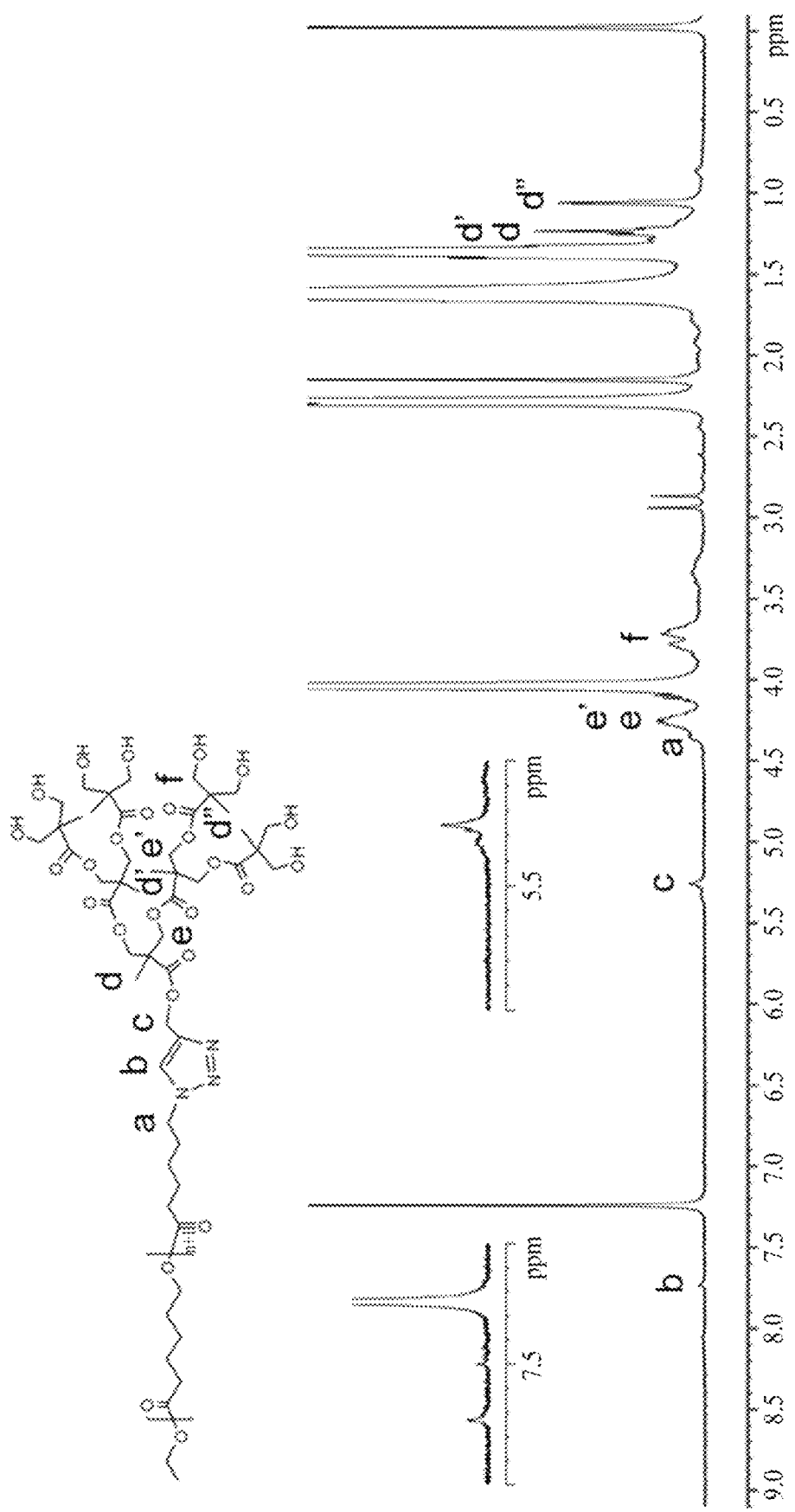
FIGS. 6A and 6B show $^1$H-NMR spectra of PCL3.5K-G3 (Panel A) and PCL14K-G3 (Panel B) prepared by click reaction. In the $^1$H-NMR spectrum of PCL3.5K-G3, the characteristic peaks of the polyester dendron were observed at 4.40-4.18, 3.82-3.60, and 1.06. The three peaks corresponding to the triazole formation appeared at 7.73, 5.26 and the third overlapped with the G3 dendron.[3b, 13] In the case of PCL14K-G3, the peaks corresponding to the triazole ring appeared at 7.80, 5.27, and 4.49.
Figure 6B:
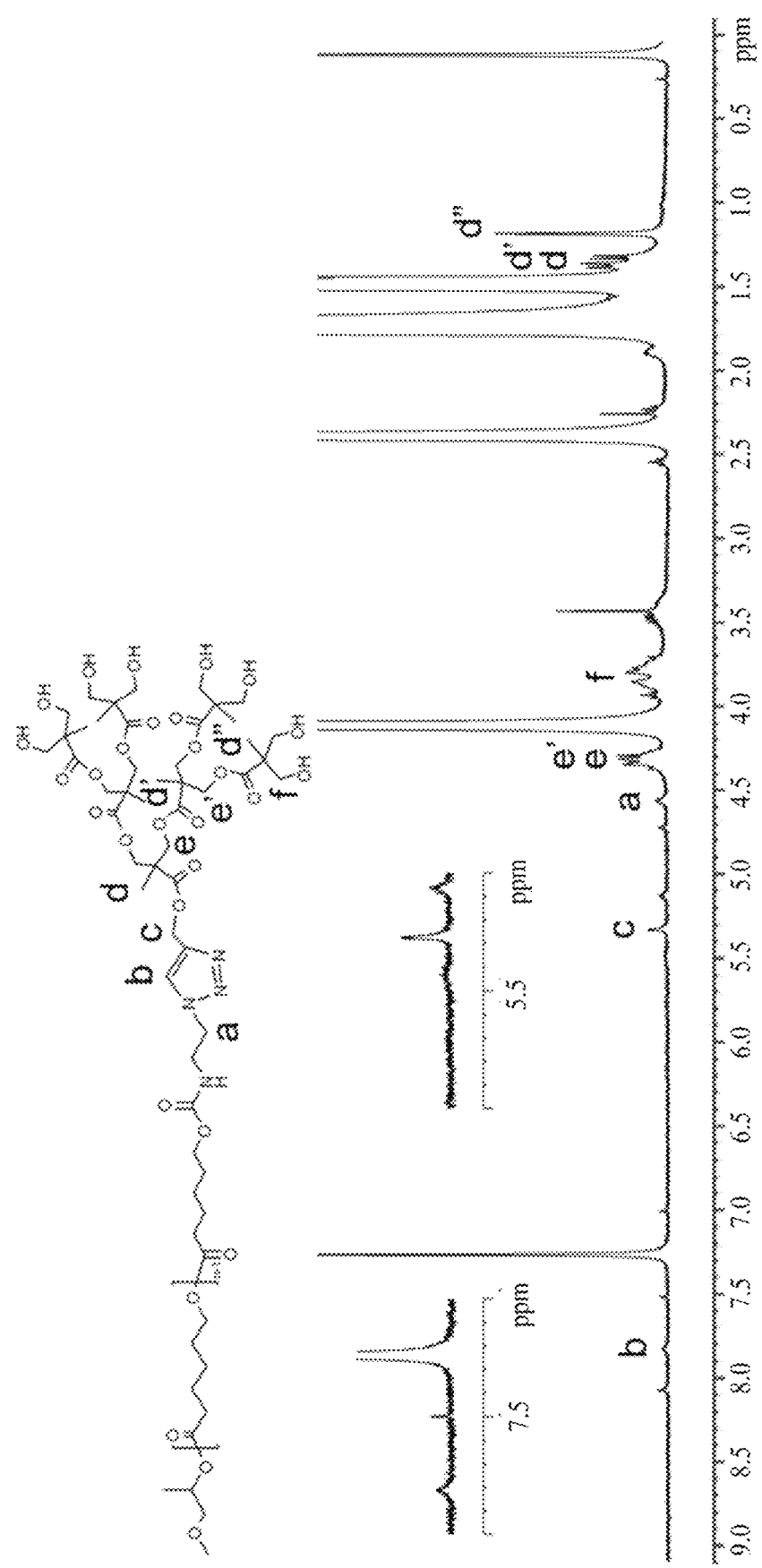
Figure 7A:
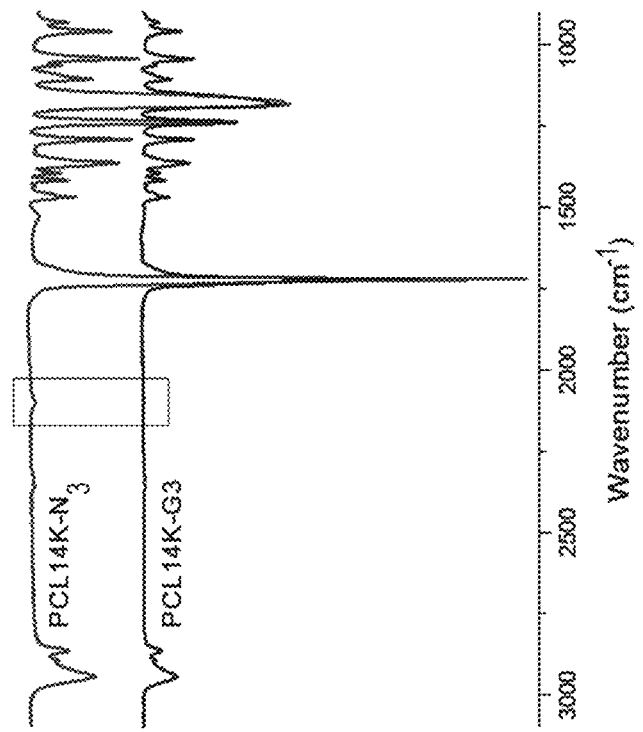
FIGS. 7A-7B show FT-IR spectra of PCL3.5K-$N_3$ and PCL3.5K-G3 (Panel A), PCL14K-$N_3$ and PCL14K-G3 (Panel B). The disappearance of the azide peak at 2095 $cm^{-1}$ in the FT-IR spectra supports that the click reaction was successful.
Figure 7B:
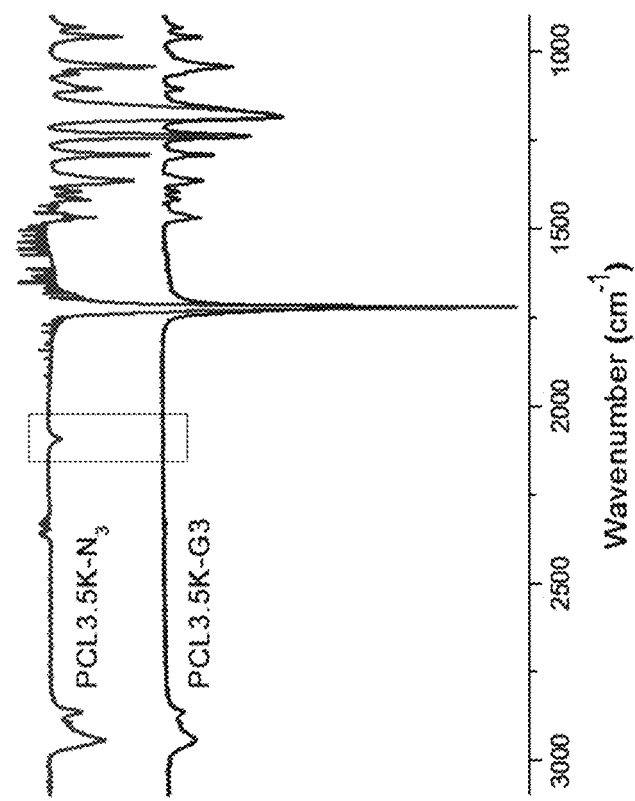
Figure 8A:
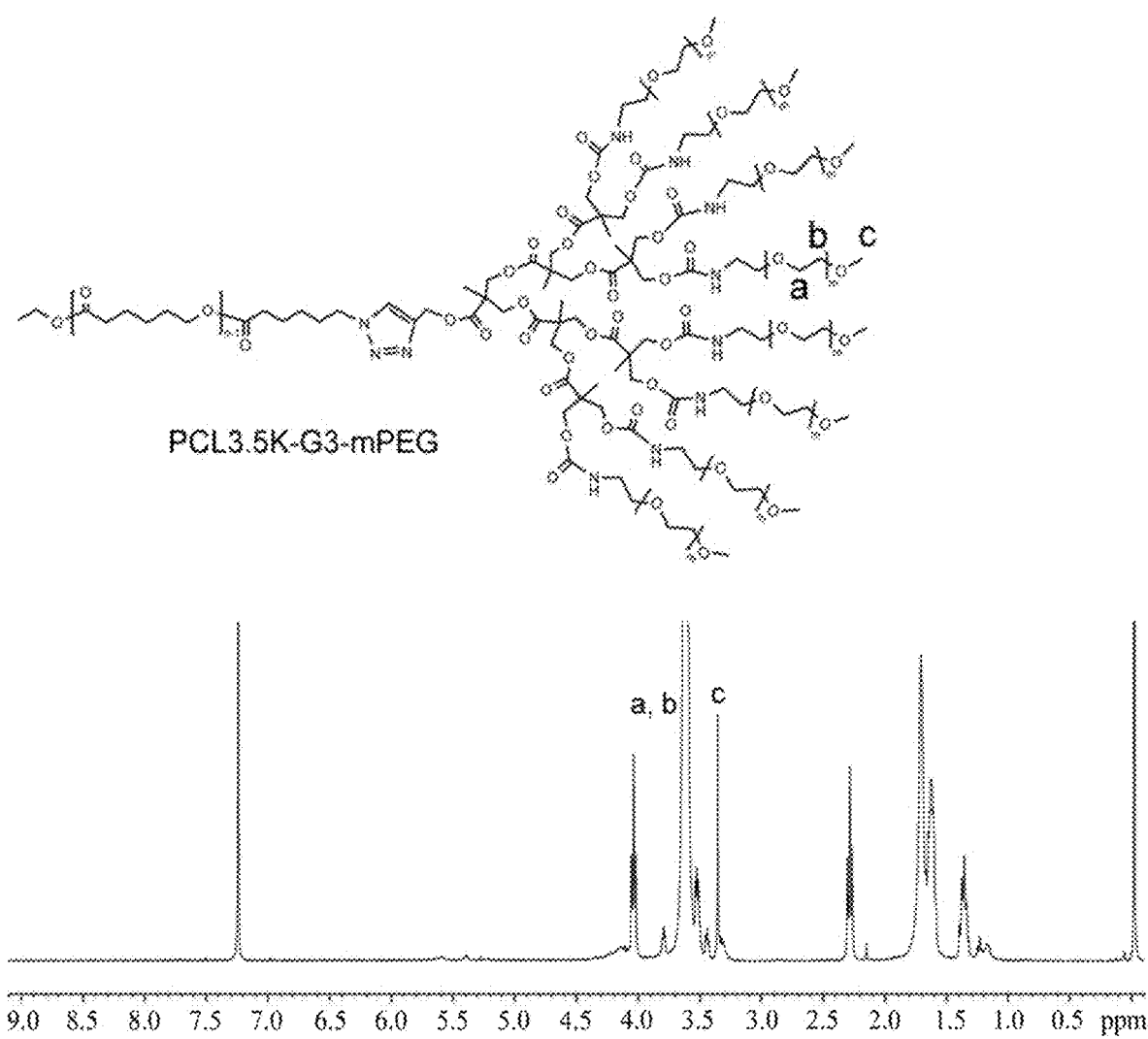
FIGS. 8A-8B show $^1$H-NMR spectra of PCL3.5K-G3-mPEG2K (A) and PCL3.5K-G3-mPEG5K (B). The major peak representing the ethylene glycol repeating unit for mPEG appeared at 3.62 along with the singlet corresponding to methoxy groups at 3.36. Setting the peak integration values of PCL as a control, the conjugated mPEG integration value was close to the theoretical number of protons needed to indicate multiple mPEG molecules were successfully introduced to the periphery of the PCL3.5K-G3. In addition, the conjugation of mPEG5K-$NH_2$ was attributed to higher intensity corresponding to the number of attached mPEG molecules, compared to linear PCL-mPEG.
Figure 8B:
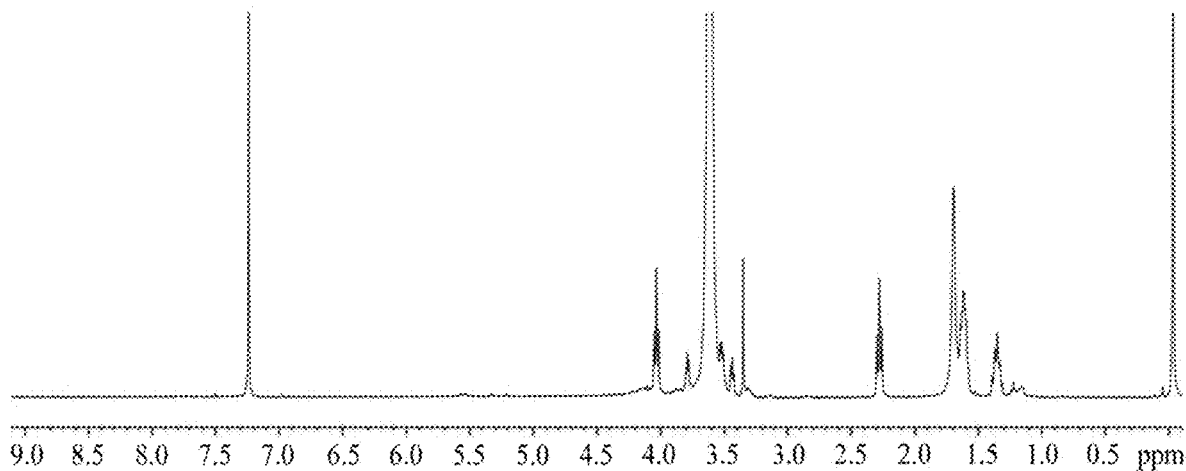
Figure 9:
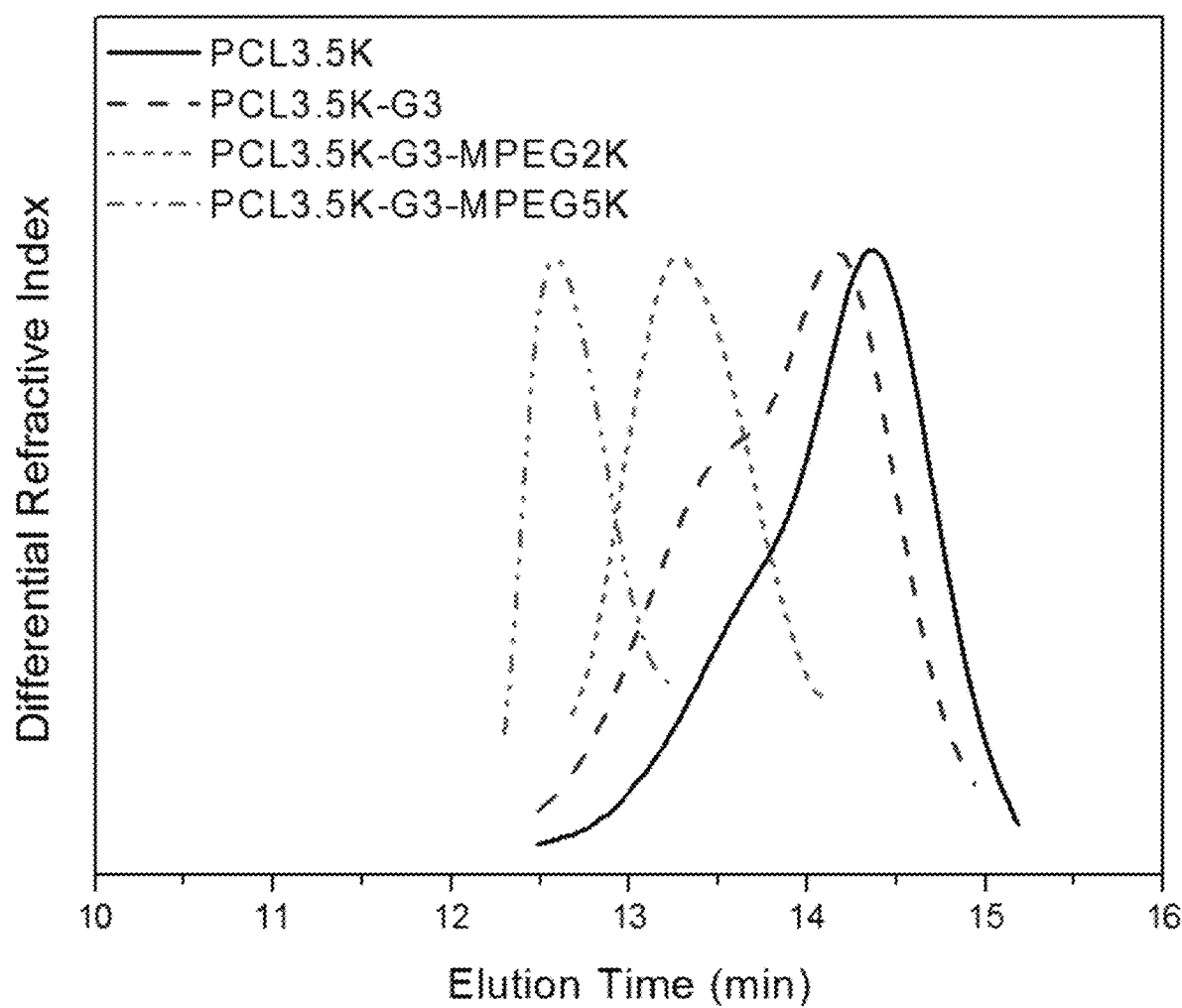
FIG. 9 shows GPC traces of PCL3.5K, PCL3.5K-G3, PCL3.5K-G3-mPEG2K, and PCL3.5K-G3-mPEG5K. The GPC traces represent the great shift to shorter elution time as the molecular weights of the samples increase.

The PEGylated DCs were synthesized via a multiple-step process. The terminal hydroxyl group of PCL3.5K and PCLI4K were first converted to an azide group (PCL-$N_3$) for subsequent conjugation with a dendron via click chemistry (FIG. 4, Panels A and B). [28] Complete conversion of the hydroxyl groups of PCL to azide was confirmed by IH-NMR (FIG. S3). G3-dendron bearing an acetylene group at the focal point was then reacted with PCL-N 3 via click chemistry to yield 2 types of PCL-G3 (FIGS. 5; 6, Panels A and B; and 7, Panels A and B).[29] To achieve high reaction yields, various click reaction conditions were tested and an optimized condition was found (See details in the Supporting information section below).[30] Both types of mPEG were then conjugated to PCL-G3 following activation of surface hydroxyl groups with p-nitrophenyl chloroformate.[31] Changes in the structures and the molecular weights of the resulting copolymers were monitored by I H-NMR and GPC at each reaction step (FIG. 8, Panels A and B; FIG. 9, Panels A and B; and Table 1).

TABLE 1

Molecular weight and polydispersity index (PDI) of polymers used in this study. The molecular weights of PCL-G3-mPEG increased significantly due to multiple conjugations of mPEG molecules to the periphery of the G3 dendron and all copolymers showed relatively narrow polydispersity around 1.07-1.38.

| Samples | Theoretical Mw | $M_n^{[a]}$ | $M_n^{[b]}$ | $PDI^{[c]}$ |
|---|---|---|---|---|
| PCL3.5K | 3,500 | — | 3,500 | 1.03 |
| PCL3.5K-G3 | 4,370 | 4,020 | 3,630 | 1.27 |
| PCL3.5K-G3-mPEG2K | 21,990 | 26,280 | 24,290 | 1.07 |
| PCL3.5K-G3-mPEG5K | 44,720 | 48,090 | 38,900 | 1.06 |
| PCL14K | 14,000 | — | 13,370 | 1.20 |
| PCL14K-G3 | 14,870 | 14,780 | 16,370 | 1.27 |
| PCL14K-G3-mPEG2K | 32,490 | 32,000 | 27,710 | 1.16 |
| PCL14K-G3-mPEG5K | 55,220 | 58,780 | 54,140 | 1.38 |

[a]Number-averaged molecular weight, $M_n$, estimated by $^1$H-NMR.
[b],[c]Measured by GPC using triple angle laser light scattering.

Interestingly, those micelles were primarily composed of hydrophilic blocks described by hydrophilic-lipophilic balances[32] (HLB) greater than 10. Yet when the thermodynamic stability was assessed by evaluation of the CMC, the values were in the $10^{-8}$ M range which is orders of magnitude lower than linear-block copolymers with the same HLBs.[33] Here, we explore this contradiction by systematic comparison of the self-assembly properties of amphiphilic DCs and linear-block copolymers.

We directly measured the thermodynamic stability of each amphiphilic copolymer by measuring the CMC.[34] Table 2 summarizes the CMC results along with HLB and LH-ratio of amphiphilic DCs and linear-block copolymers.

TABLE 2

Critical micelle concentrations (CMCs) of the amphiphilic copolymers with various hydrophilic-lipophilic balances (HLBs).

| Sample | $HLB^a$ | HL-ratio$^b$ | CMC (mg/L) | CMC ($10^{-7}$ M) |
|---|---|---|---|---|
| PCL3.5K-mPEG2K | 7.27 | 36:64 | 1.32 | 2.40 |
| PCL3.5K-mPEG5K | 11.76 | 59:41 | 3.29 | 3.75 |
| PCL14K-mPEG2K$^c$ | 2.50 | 13:87 | — | — |
| PCL14K-mPEG5K | 5.26 | 26:74 | 1.62 | 0.82 |
| PCL3.5K-G3-mPEG2K | 16.56 | 77:23 | 4.87 | 3.02 |
| PCL3.5K-G3-mPEG5K | 18.42 | 91:9 | 12.59 | 3.52 |
| PCL14K-G3-mPEG2K | 10.93 | 52:48 | 1.62 | 0.65 |
| PCL14K-G3-mPEG5K | 14.90 | 74:26 | 4.74 | 1.17 |

$^a$HLB = 20 $M_H$/($M_H$ + $M_L$), where $M_H$ is the mass of the hydrophilic block and $M_L$ is the mass of the lipophilic block. The polyester dendron is considered to be part of the hydrophilic block.
$^b$Hydrophilic-lipophilic ratio.
$^c$PCL14K-mPEG2K could not be tested due to its poor water solubility.

Figure 10:
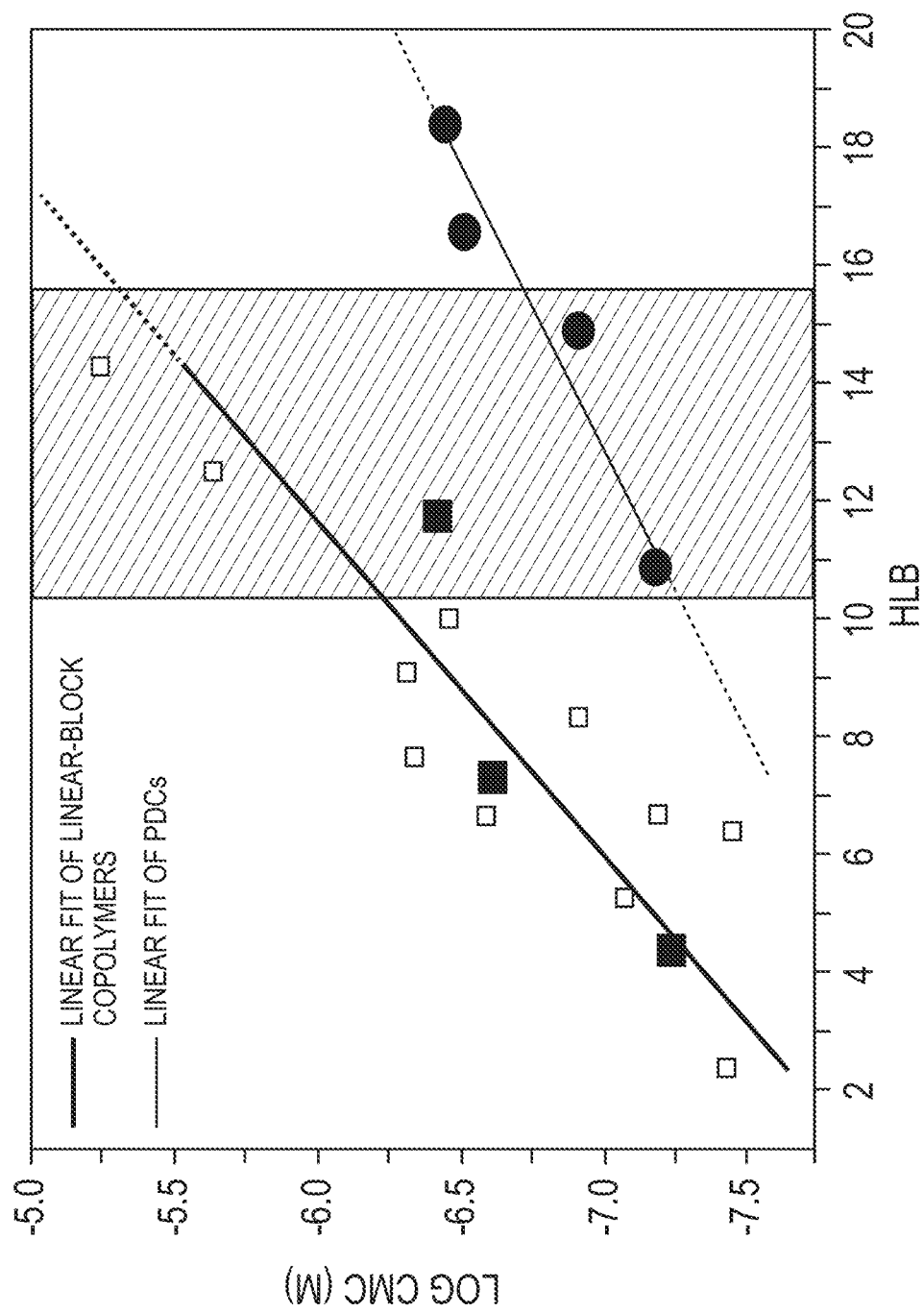
FIG. 10 shows a graph of the relationship between ln CMC and HLB for DC (circles) and linear-block copolymers (squares).

The CMC values of linear diblock copolymers were in good agreement with previous reports.[33a, 35] The CMC values of the amphiphilic DCs were comparable to linear PCL-mPEG diblock copolymers even though in some cases, the HLB for amphiphilic DCs was twice as large (~90% hydrophilic). Amphiphilic DCs bearing PCL3.5K lipophilic blocks had similar CMC values to those of linear PCL-mPEG copolymers despite an average increase in HLB of 8 corresponding to a 40% increase in hydrophilicity. PCL14K-mPEG5K with the lowest HLB of all polymers tested at 5.26 was determined to have a CMC of $0.82 \times 10^{-7}$ M. Remarkably its counterpart. PCLI4K-G3-mPEG5K with HLB of 14.90 had a CMC of $1.17 \times 10^{17}$ M. PCL14K-G3-mPEG2K was found to have the lowest CMC at $0.65 \times 10^{-7}$ M amongst all copolymers tested even with an HLB of 10.93. The presence of the dendron accounted for the dramatic increase in HLB observed in the amphiphilic DC structures, however this does not explain the preservation of low CMC values observed. Plotting ln CMC against HLB illustrates the relationship between HLB and CMC for the linear and amphiphile DCs (FIG. 10).[36] The notable shift to the right for the amphiphilie DCs towards higher HLBs without subsequent increase in ln CMC demonstrates that the thermodynamic stability of the amphiphilic DCs is superior to that of linear-block copolymers.

Figure 11:
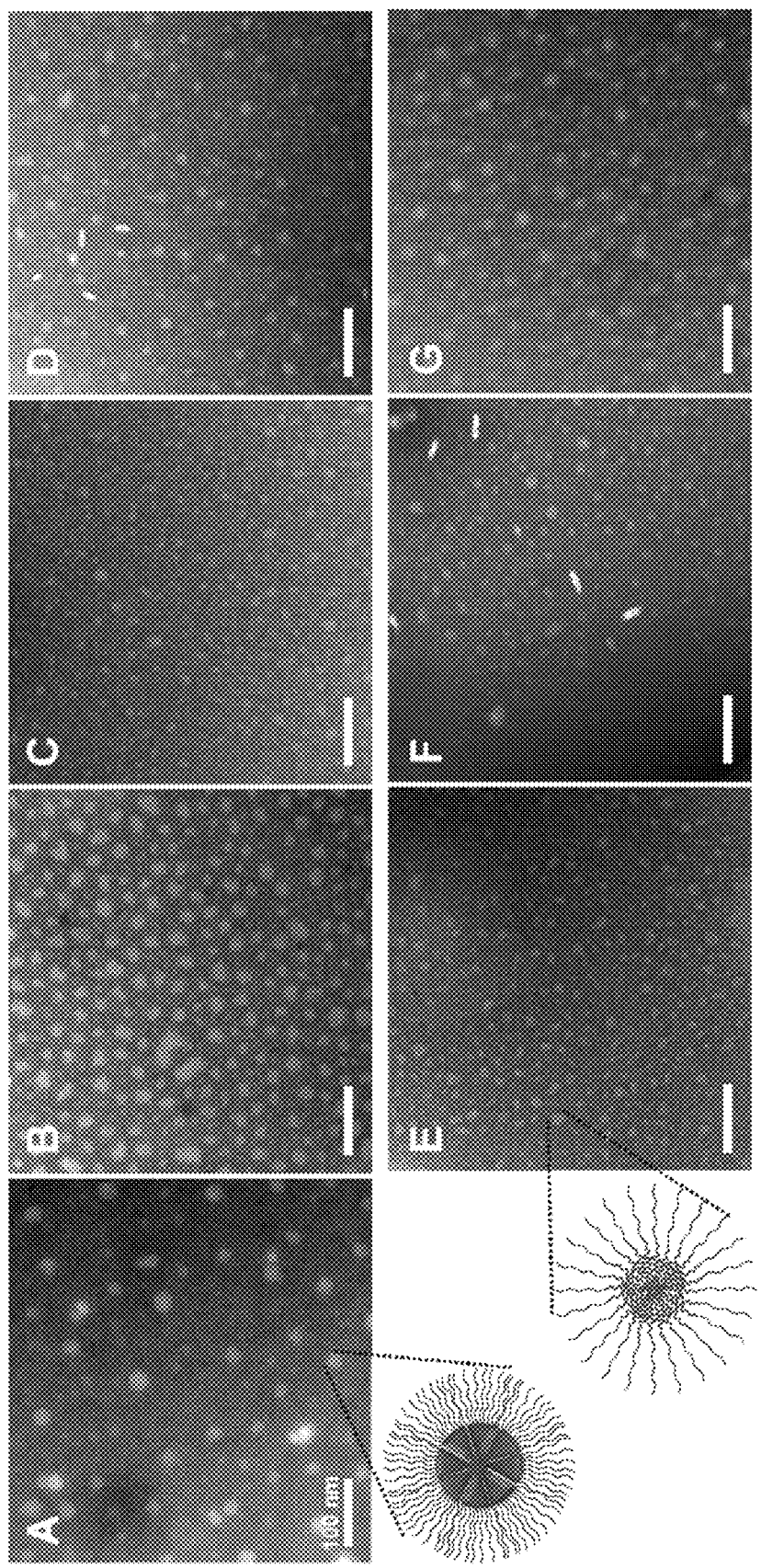
FIG. 11 shows transmission elecron micrograph images of self-assembled structures. (Panel A) PCL3.5K-G3-mPEG2K, (Panel B) PCL3.5K-G3-mPEG5K, (Panel C) PCL14K-G3-mPEG2K, (Panel D) PCL14K-G3-mPEG5K, (Panel E) PCL3.5K-mPEG2K, (Panel F) PCL3.5K-mPEG5K, and (Panel G) PCL14K-mPEG5K. All samples were prepared at 0.2 mg/mL and stained with 2% Phosphotungstic Acid (pH 7). Scale bar=100 nm.

The size and morphology of self-assembled structures of the linear-block copolymers and amphiphilic DCs were examined using TEM and DLS. All samples were prepared at a concentration above their CMC by the dialysis method.[35a] As shown in FIG. 11, TEM images show that all DC micelles were spherical in shape and homogeneous in size, as similarly observed in the cases of the PCL-mPEG micelles. DC micelles (FIGS. 11C and D) with a longer PCL block were smaller in diameter than the micelles with PCL3.5K (FIGS. 11A and B). Average sizes of PCL3.5K-G3-mPEG2K and PCL3.5K-G3-mPEG5K micelles measured by DLS were approximately 18 nm. In contrast, PCL14K-G3-mPEG2K and PCL14K-G3-mPEG5K micelles were larger in size (30 and 50 nm, respectively).

Figure 12E:
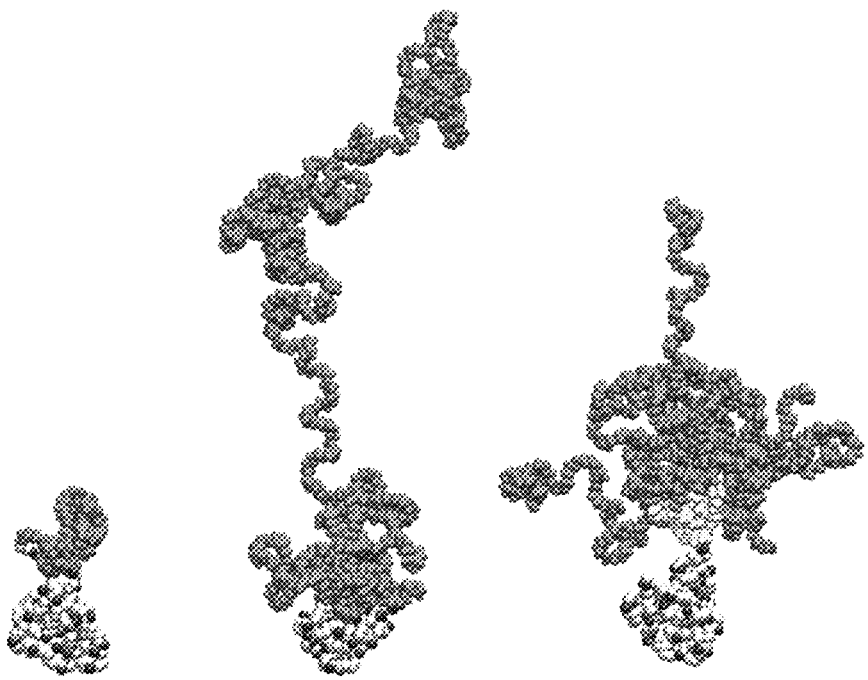
Figure 12E:
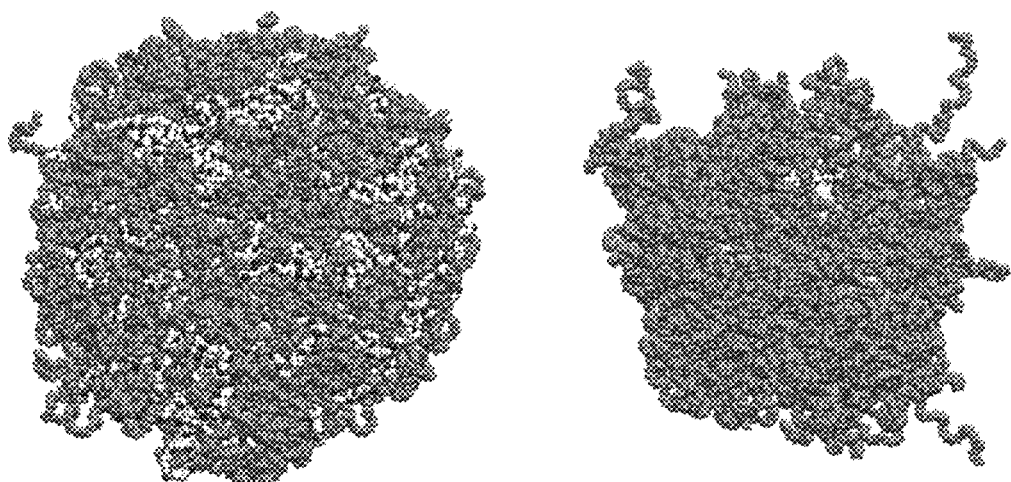

In order to understand in molecular detail the experimental observations, we modeled by atomistic molecular dynamics (MD) simulations single linear PCL3.5K-mPEG2K, PCL3.5K-mPEG16K and PCL3.5K-G3-mPEG2K in monomer and micelle forms (See details in Supporting Information). FIG. 12 shows the equilibrated structures after 5 nanoseconds (ns) of (Panel a) PCL3.5K-mPEG2K, (Panel b) PCL3.5K-mPEG16K, and (Panel c) PCL3.5K-G3-mPEG2K monomers in water and each was characterized in terms of their size and shape. In all the monomers, a compact PCL tail and an extended conformation of the PEG blocks due to their solvation in water was observed. The sizes of the compact PCL blocks are similar in all three cases, whereas there is a distinct difference in the sizes of the PEG layer for each. Monomers (Panel b) and (Panel c), which have the same molecular weight of PEG blocks and identical HLBs, do not have the same conformation of PEG blocks due to differences in molecular geometry. The simulation revealed that the eight grafted PEG chains on the amphiphilic DC adopt a fan-like shape (in comparison to a single PEG chain solvated in water) due to the pre-organized architecture of the dendron allowing a conical shape to be adopted. The conical morphology is a result of the hydrophobic effect[37] where the compaction of the PCL tail occurs to minimize the entropic loss of water reducing the energy at the PCL-water interface. Additionally, the observed increase in peripheral surface area for the amphiphilic DC can be attributed to steric repulsive forces between mPEG chains and high mPEG density.

We also simulated micellar assemblies of PCL3.5K-rnPEG2K and PCL3.5K-G3-mPEG2K to understand the experimentally observed morphologies. FIG. 12 shows micelles formed from (Panel d) 128 monomers of PCL3.5K- mPEG2K and (Panel e) 14 monomers of PCL3.5K-G3-mPEG2K equilibrated in water for 5 ns. Micelle aggregation number ($N_{agg}$) for each was chosen to best represent the observed sizes of linear and DC micelles by TEM. Indeed, the aggregation number for PCL3.5K-mPEG2K micelles were quite close to the experimentally measured aggregation numbers of micelles with a similar structure.[38] In all equilibrated micelles, either two or three unique regions were recognizable: PCL core and PEG corona, or PCL core, dendron and PEG corona. The micelle cores were found to reorganize only slightly during several ns to form a spherical shape. In a separate simulation, a PCL3.5K-G3-mPEG2K micelle with 18 monomers was prepared and showed a distorted elongated shape. Therefore, we can conclude that spherical micelles can be observed for amphiphilic DC $N_{agg}$<18.

The stability and self-assembly behaviors of amphiphilic DCs is contradictory to current thought that copolymers with large HLBs have high CMCs. We used a simple analytic model to examine the entropic cost associated with the confinement of hydrophilic PEG blocks when in the micellar phase. To estimate the approximate entropic cost, it is assumed that PEG can be described within the framework of ideal chain theory.[39] An ideal chain of length L is comprised of n segments, each of statistical segment length l, so that L=ln. When placed in a good solvent (such as water), the PEG chain swells to maximize the number of polymer-fluid contacts. Configurations of the ideal chain can be characterized by a probability distribution function which depends on the chain end-to-end (e-t-e) distance. An ideal chain has a well defined average e-t-e distance $<r>=ln^{1/2}$ which is associated with minimum (configuration) free energy of the polymer. When the PEG becomes confined during self-assembly process, its average e-t-e distance will increase and the free energy cost associated with this extension is purely entropic. Entropy of a freely jointed chain with a given e-t-e distance is proportional to the logarithm of the number of chain configurations for that e-t-e distance. This is in turn proportional to the probability of the PEG having this e-t-e distance. The entropy difference between PEG chains in a given conformation with different e-t-c extensions is given by: [39]$\Delta S=S-S_1=k_B b^2(r_1^2-r^2)$ where S and $S_1$ are configurational entropies associated with e-t-e extensions r and $r_1$, $k_B$ is the Boltzmann constant and $b^2=3/(2nl^2)$.

For PCL3.5K-mPEG16K polymer, the PEG block has n=363 segments, each of the length l=3.68 Å. In water, the average e-t-e distance of this polymer is $<r>=ln^{1/2}≈70$ Å. Assume that due to steric confinement the e-t-e distance of the chains in the micelle is extended by 50% from the above value of <r>, the entropic cost for this extension is 1.11 kcal/mol≈1.9 $k_BT$. Since every chain forming a micelle needs to pay this configurational entropic cost, the micelle formation is not favorable for polymers with long hydrophilic blocks. Previously, we had hypothesized that the dendron geometry facilitates self-assembly of copolymers with high HLB due to low entropic costs. For amphiphilic DC monomers solvated in water, eight grafted PEG chains are forced to assume extended conformations due to their density and steric repulsion. When these copolymers form micelles, further extensions of the PEG blocks are likely small, in good agreement with the results of our MD simulations. Since the average e-t-e extensions of PEG of DC in solvated and micellar phases are similar, the associated conformational entropy cost is also small compared to the enthalpic binding, resulting in micellar phase being favored. For linear polymers, extensions of PEG will be considerable, resulting in larger differences in conformational entropies in monomer and aggregated states accounting for their increased CMC values compared to DCs with the same HLBs.

There are several pieces of evidence suggesting that certain geometric constraints placed on amphiphilic molecules enables the minimization of the free energy associated with the self-assembly process.[40b, 41] Using geometrical relationships developed by Nagarajan[42], it is clearly observed that DCs will have a smaller aggregation number, g, than linear copolymers with the same tail length. Based on Tanford's free energy expression as described by Nagarajan[42], minimization of free energy results in low CMCs. The high flexibility and number of PEG on the exterior of each DC can promote the dense packing of monomers which results in a decrease in CMC as observed in the measured dimensions for each micelle (Table 3).[43]

TABLE 3

Dependence of the total micelle diameter ($d_{total}$), core diameter ($d_{core}$) and PEG corona diameter ($d_{PEG}$) based on aggregation number ($N_{agg}$) and monomer type. These values are obtained by angular averaging (2-5 ns) of the radial extensions of the PEG chains with respect to the micelle center of mass.

| Samples | $N_{agg}$ | $d_{total}$ (nm) | $d_{core}$ (nm) | $d_{PEG}$ (nm) |
|---|---|---|---|---|
| PCL3.5K-mPEG2K | 86 | 12.94 | 11.44 | 0.75 |
| PCL3.5K-mPEG2K | 128 | 15.22 | 13.54 | 0.84 |
| PCL3.5K-G3-mPEG2K | 14 | 13.42 | 7.68 | 2.87 |
| PCL14K-G3-mPEG2K | 10 | 12.98 | 9.18 | 1.91 |

The results presented here support our hypothesis that the self-assembly process of amphiphilic DCs is more thermodynamically favored than linear PCL-mPEG copolymers and that entropic effects attribute greatly to the increased stability of amphiphilic DCs with large HLBs. In comparison to linear-block copolymers, our results indicate that the molecular structure of the DC: (1) enables the self-assembly process to be thermodynamically favored resulting in ultralow CMC values and homogeneous size distributions of self-assembled structures; and (2) the entropy cost associated with the self-assembly of DCs is much lower than linear-block copolymer counterparts even with high HLBs due to the preorganized dendron architecture.

In order to test the capability of DC micelles as drug delivery vehicles, indomethacin (IMC) was encapsulated into micelles. IMC loading and encapsulation percentages were calculated, and a drug release test and cytotoxicity test were carried out.

The IMC loading and encapsulation percentages were calculated as Loading (%)=(Measured IMC amount/Mass of IMC loaded micelle)×100(%) and Encapsulation (%)=(Measured IMC amount/Theoretical IMC loading amount)×100 (%). As shown in Table 4, the encapsulation efficiencies (%) were significantly different between PCL3.5K-G3-mPEG2K and PCL3.5K-G3-mPEG5K IMC loaded micelles based on a 1-way ANOVA followed by Tukey's post-hoc test at p<0.05.

TABLE 4

IMC loading and encapsulation of various micelles (n = 3).

| Samples | Loading (%) | Encapsulation (%) | IMC/PCL ratio |
|---|---|---|---|
| PCL3.5K- mPEG2K | 6.7 ± 0.3 | 73.9 ± 3.3 | 1.62 |
| PCL3.5K- mPEG5K | 7.8 ± 0.7 | 85.7 ± 7.6 | 4.50 |
| PCL14K- mPEG5K | 8.4 ± 0.2 | 92.7 ± 2.4 | 6.05 |
| PCL3.5K-G3-mPEG2K | 8.3 ± 0.5 | 90.8 ± 5.6 | 32.05 |
| PCL3.5K-G3-mPEG5K | 5.0 ± 0.4 | 54.9 ± 3.9 | 79.83 |

TABLE 4-continued

IMC loading and encapsulation of various micelles (n = 3).

| Samples | Loading (%) | Encapsulation (%) | IMC/PCL ratio |
|---|---|---|---|
| PCL14K-G3-mPEG2K | 9.3 ± 2.4 | 102.7 ± 25.8 | 19.60 |
| PCL14K-G3-mPEG5K | 6.2 ± 2.8 | 68.4 ± 31.2 | 37.75 |

The differences among all other samples were not statistically significant. IMC/PCL ratio represents the moles of IMC encapsulated per mole of PCL present in the copolymer, demonstrating that the amount of IMC encapsulated per amount of PCL was one order of magnitude greater than that of the linear-block copolymer micelles. The IMC/PCL ratios were calculated based on following. For the example of PCL3.5K-G3-mPEG2K, assuming 1 mg of drug encapsulated micelle, (1 mg/21990 mg/mmol)×(3500 mg PCL/21990 mg micelle)=7.238×10$^{-6}$ mmol PCL. Calculating the mass of IMC contained within 1 mg of micelle (loading) and converting to moles IMC: (0.083 mg IMC)×(1 mmol/357.79 mg IMC)=2.320×10$^{-4}$ mmol IMC. Therefore, IMC/PCL ratio=2.320×10$^{-4}$ mmol IMC/7.238×10$^{-6}$ mmol PCL=32.05.

Figure 13:
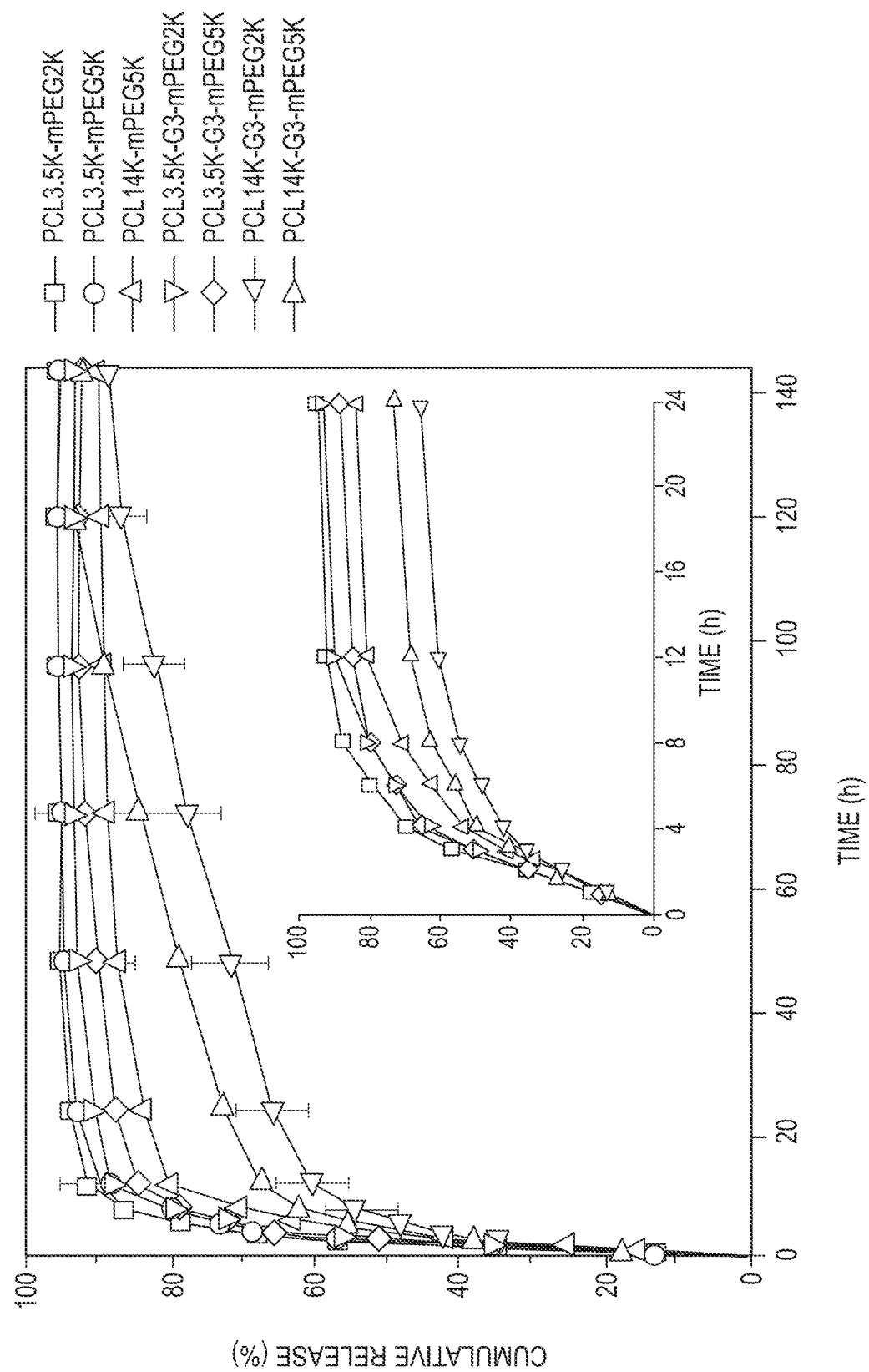
FIG. 13 shows release profiles of IMC from various micelles for 6 days. Inset: release profiles of various micelles over the first 24 h.
Figure 14:
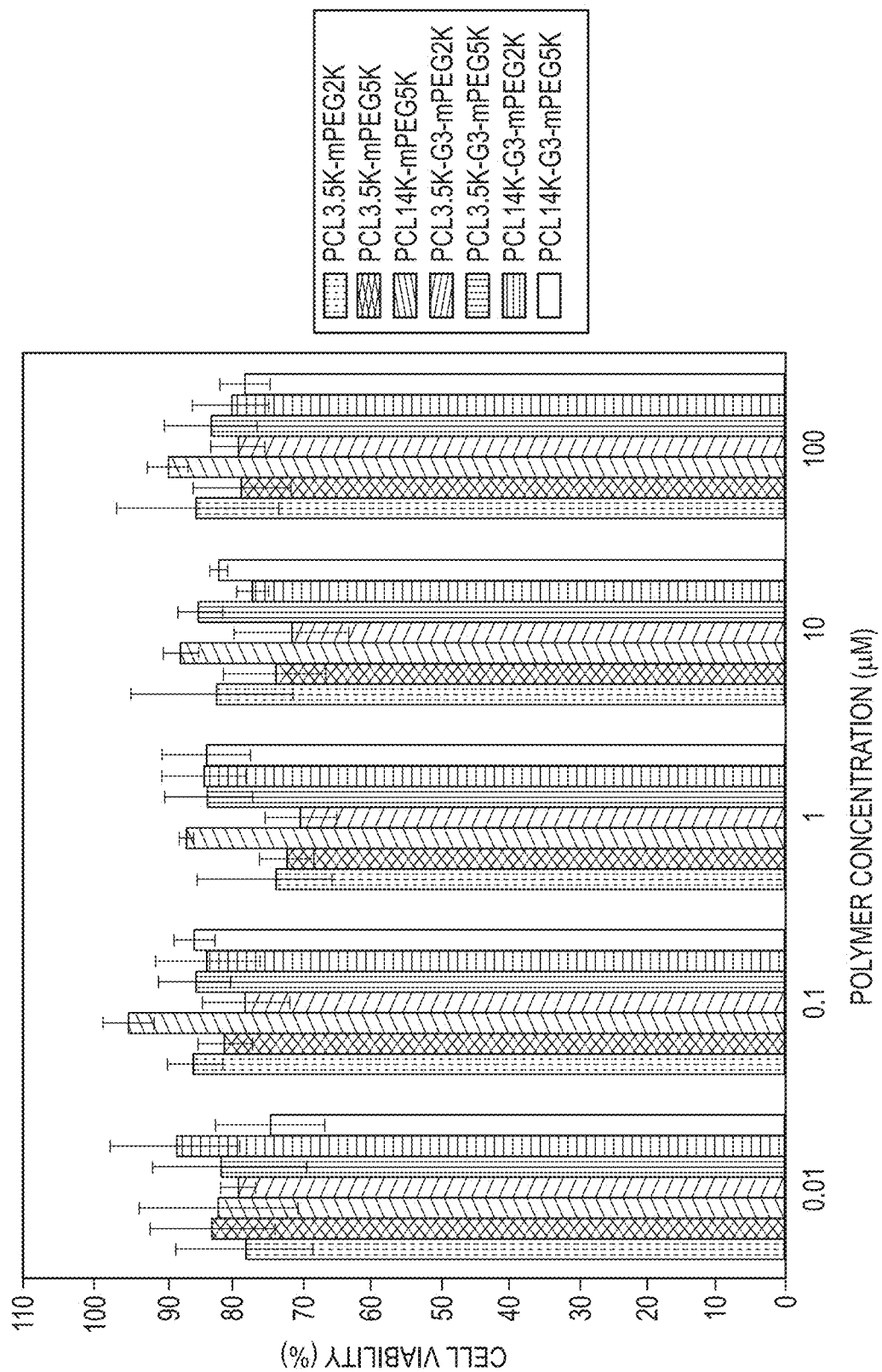
FIG. 14 shows MTS assay results for cell viability of KB cells after 24 h incubation with various block copolymers. All data were expressed as the mean of triplicate cultures. All the polymers do not exhibit significant toxicity in the range of concentrations as high as 100 μM.

FIG. 13 shows controlled release of IMC from the micelles over time, There were no difference in the IMC release profiles between PCL-G3-mPEG and PCL-mPEG micelles. A noticeable difference was observed with the micelles with PCL14K during the first 24 h. This is probably due to increased hydrophobic interactions between PCL and IMC as well as more packed micellar structures leading to a slower rate of diffusion. The cytotoxicity of the various copolymers was evaluated on KB cells after 24 h incubation by MTS assay (FIG. 14). All copolymers did not exhibit significant cytotoxicity at concentrations up to 100 μM.

Thus, we report the synthesis of four newly designed amphiphilic DCs with different HLBs that are composed of PCL, G3 polyester dendron and mPEG. The results from a systematic study of the self-assembly properties of amphiphilic DCs compared to the linear-block copolymers explain that a preorganized and conical architecture of dendron can contribute to facilitate a self-assembly of amphiphilic DCs. In particular, the self-assembling process mediated by the dendron is thermodynamically favored resulting in ultra low CMCs even at extremely high HLBs, which is also supported by MD simulations. The DC micelles showed controlled drug release behaviors as well good biocompatibility. The facilitated supramolecular structure formation at ultra low CMCs and high HLBs, along with the biocompatibility, all prove that the DC micelles have great potential for use as a versatile drug delivery platform.

Supporting Information for Example 2
Materials

Hydroxyl-terminated poly(ε-caprolactone) (PCL) polymers with two different molecular weights ($M_n$ 3500 and PDI 1.18, $M_n$ 14000 and PDI 1.20) were purchased from Polymer Source Inc. (Montreal, Canada). Generation 3 polyester-8-hydroxyl-1-acetylene bis-MPA dendron (G3 dendron; G3), p-toluenesulfonyl chloride (TsCl), 2-bromoethyl isocyanate (BEI), triethylamine (TEA), trimethylamine hydrochloride (TMA), sodium azide (NaN$_3$), anhydrous sodium sulfate, N,N,N',N",N"-pentamethyldiethylenetriamine (PMDETA), copper bromide (CuBr), dibutyltin dilaurate (DBTDL), and p-nitrophenyl chloroformate (p-NPC) and indomethacin (IMC) were all provided by Sigma Aldrich Co. (St. Louis, USA). Methoxy polyethylene glycol amine (mPEG-NH$_2$, $M_n$ 2000 and PDI 1.02, $M_n$ 5000 and PDI 1.04) was purchased from JenKem Technology USA Inc. (TX, USA). Regenerated cellulose dialysis membranes (3.5K and 12-14K MWCO) were purchased from Spectrum Labs (CA, USA). All solvents and reagents were used without further purification unless otherwise specified.

Synthesis of PCL3.5K-G3 Dendron Via Click Reaction

Tosylation of PCL3.5K. A terminal hydroxyl group of PCL was firstly tosylated prior to introduction of an azide group as previously reported (FIG. 4).[44] PCL3.5K (1 g, 0.286 mmol) along with TEA (200 μl, 1.43 mmol) and trimethylamine hydrochloride (14 mg, 0.143 mmol) were dissolved in 8 mL of dichloromethane. To this solution, TsCl (272 mg, 1.430 mmol, 5 eq.) dissolved in 2 mL of dichloromethane was added dropwise. The reaction was carried out at room temperature for 24 h. Following the reaction, the solvent was evaporated until a viscous liquid remained. The viscous liquid was then precipitated into cold diethyl ether, filtered, and dried in vacuo (Yield: 90%).

Azido-functionalization of PCL3.5K-Ts. The tosyl group of PCL3.5K-Ts was converted into azide for subsequent click chemistry. PCL3.5K-Ts (840 mg, 0.24 mmol) was dissolved in 8 mL of dimethylformamide. To this solution, sodium azide (312 mg, 4.8 mmol, 20 eq.) was added and reacted at room temperature for 24 h under N$_2$. The reaction mixture was diluted with 200 mL of dichloromethane and washed three times with 150 mL of deionized water and once with 200 mL of brine. The organic layer was dried over anhydrous sodium sulfate, filtered, concentrated, and precipitated into cold diethyl ether (Yield: 70%).

Synthesis of PCL3.5K-G3 dendron. PCL3.5K-G3 dendron was synthesized via click chemistry between PCL3.5K-N$_3$ and G3 dendron bearing an acetylene group in the presence of copper (I) and a base by modification of a previously reported method.[2] PCL3.5K-N$_3$ (73 mg, 0.021 mmol) and G3 dendron (20 mg, 0.023 mmol, 1.1 eq.) were dissolved in 2 mL of dimethylformamide containing PMDETA (7.3 mg, 0.042 mmol, 2 eq.). After dissolving, copper bromide (6 mg, 0.042 mmol, 2 eq.) was added and the reaction was carried out at 80° C. for 24 h. Products were recovered by precipitation into cold diethyl ether and filtration (Yield: 96%).

Synthesis of PCL14K-G3 Dendron Via Click Reaction

Bromination of PCL14K. The terminal hydroxyl group of high molecular weight PCL was easily converted into bromide by reaction with 2-bromoethyl isocyanate (FIG. S1B). PCL14K (1 g, 0.071 mmol) was dissolved in 15 mL of toluene containing TEA (11 μl, 0.071 mmol) with a catalytic amount of DBTDL. To this solution, 1 mL of toluene containing 2-bromoethyl isocyanate (108 mg, 0.714 mmol, 10 eq.) was added dropwise and reacted at room temperature for 24 h under N$_2$. Following the reaction, the solvent was evaporated until a viscous liquid remained. The viscous liquid was then precipitated into cold diethyl ether, filtered and dried in vacuo (Yield: 92%).

Azido-functionalization of PCL14K-Br. The bromine group of PCL14K-Br was converted into azide for click chemistry. PCL14K-Br (910 mg, 0.065 mmol) was dissolved in 12 mL of dimethylformamide. To this solution, sodium azide (84 mg, 1.3 mmol, 20 eq.) was added and reacted at room temperature for 24 h under N$_2$. The reaction mixture was diluted with 200 mL of dichloromethane and washed three times with 150 mL of deionized water and once with 200 mL of brine. The organic layer was dried over anhydrous sodium sulfate, filtered, concentrated and precipitated into cold diethyl ether (Yield: 81%).

Synthesis of PCL14K-G3 dendron. PCL14K-G3 dendron was synthesized via click chemistry between PCL14K-N$_3$ and G3 dendron bearing an acetylene group in the presence of copper (I) and a base by modification of a previously reported method.[45] PCL14K-N$_3$ (200 mg, 0.0143 mmol) and G3 dendron (16 mg, 0.0157 mmol, 1.1 eq.) were dissolved in 3 mL of dimethylformamide containing PMDETA (4.94 mg, 0.0286 mmol, 2 eq.). After dissolving, copper bromide (4 mg, 0.0286 mmol, 2 eq.) was added and the reaction was carried out at 80° C. for 24 h. Products were recovered by precipitation into cold diethyl ether and filtration (Yield: 95%).

mPEG Conjugation to PCL-G3 Dendron mPEG conjugation was accomplished following activation of the peripheral hydroxyl groups on PCL-G3 dendron (FIG. 5).[46] PCL-G3 dendron was dissolved in 8 mL of dichloromethane containing pyridine (5 eq.). After adding p-NPC (5 eq.) dropwise, the reaction was carried out at room temperature for 24 h. The solvent was evaporated until a viscous liquid remained. The viscous liquid was then precipitated into cold diethyl ether, filtered and dried in vacuo. For mPEG conjugation, a solution of the activated PCL-G3 dissolved in 1 mL of dimethylformamide was added dropwise to 3 mL of dimethylformamide containing mPEG-NH$_2$ (1.2 eq.) and TEA (4 eq.). The reaction was carried out at room temperature for 24 h. The solution was then transferred into a dialysis bag (MWCO 3.5K for mPEG2K-NH$_2$ and MWCO 12-14K for mPEG5K-NH$_2$), dialyzed for 2 days, and then freeze dried for 2 days (Yields: >70%).

Synthesis of Linear PCL-mPEG Copolymers 300 mg of PCL was dissolved in 8 mL of dichloromethane containing pyridine (5 eq.). After adding p-NPC (5 eq.) dropwise, the reaction was carried out at room temperature for 24 h. The solvent was evaporated until a viscous liquid remained. The viscous liquid was then precipitated into cold diethyl ether, filtered and dried in vacuo (Yields: >90%). A solution of the activated PCL dissolved in 1 mL of dimethylformamide was added dropwise to 3 mL of dimethylformamide containing mPEG-NH$_2$ (1.2 eq.) and TEA (4 eq.) and reacted at room temperature for 24 h. The crude product was transferred into a dialysis bag, dialyzed for 1 day and then freeze dried for 2 days (Yields: >80%). For PCL14K-mPEG copolymers, the extraction method was used due to their low HLB values (Yields: >60%).

Polymer Characterization $^1$H-NMR spectra were recorded at 400 MHz (DPX-400 NMR spectrometer, Bruker Biospin Co., MA, USA). NMR chemical shifts are reported in ppm with calibration against a solvent signal. FT-IR spectra were recorded using FT-IR spectrophotometer (NEXUS 870, Thermo Nicolet Co., WI, USA). GPC measurements were carried out using a 600 HPLC pump, 717plus Autosampler, 2414 Refractive Index detector (Waters, Milford, Mass., USA) and a MiniDAWN™ TREOS triple-angle light scattering detector (Wyatt, Santa Barbara, Calif., USA) using THF as the mobile phase at 1 mL/min with Waters Styragel® HR2 and HR4E columns at 30° C.

Additional Synthetic Description

Figure 15A:
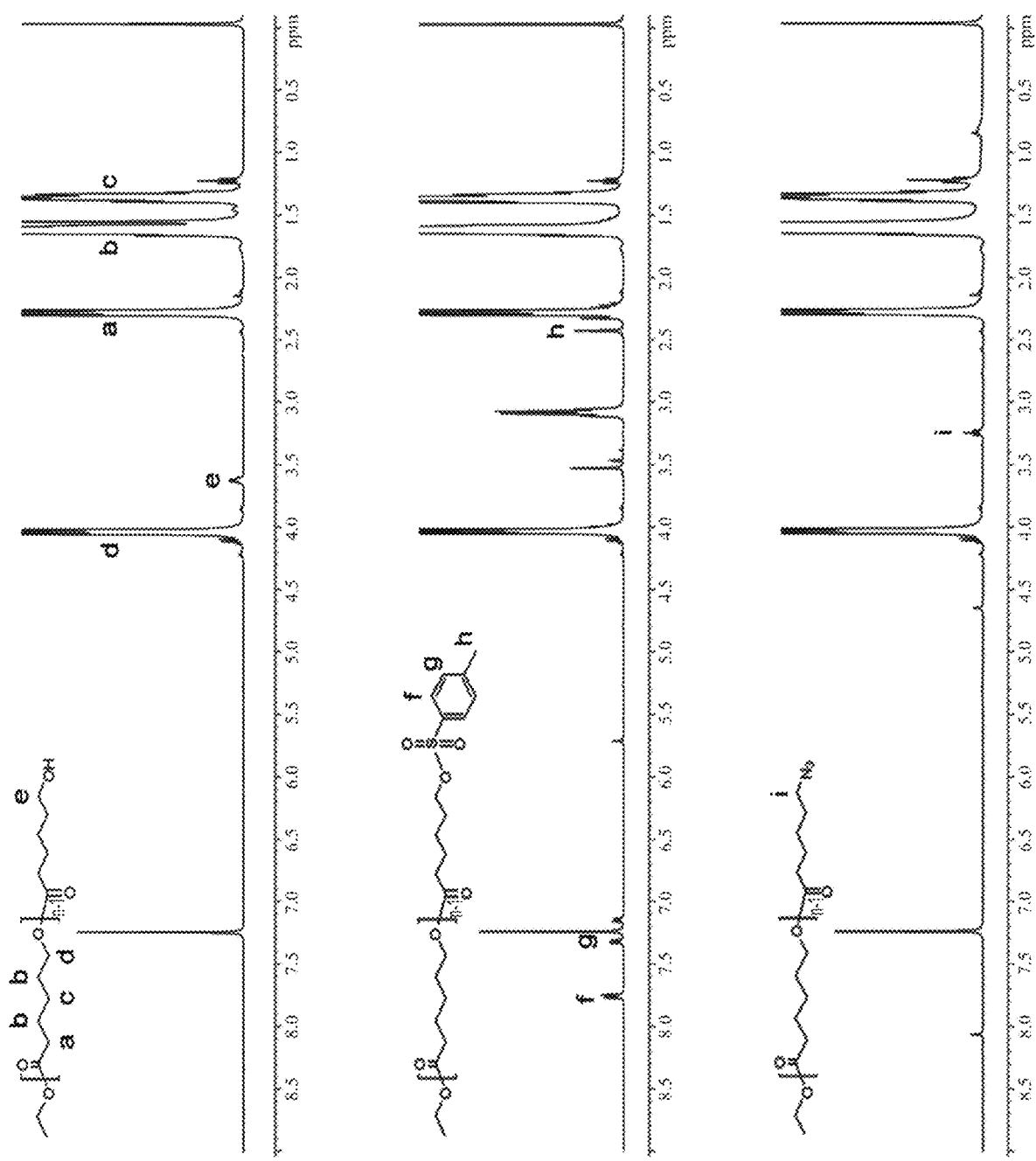
FIGS. 15A and 15B show $^1$H-NMR spectra of PCL3.5K (Panel A) and PCL14K derivatives (Panel B). The peaks corresponding to two protons adjacent to a hydroxyl group of PCL ("e" for PCL3.5K and "a" for PCL14K) completely disappeared after the reactions. The peak shifts of PCL14K between 3.7 and 3.2 were clearly observed according to each reaction step.
Figure 15B:
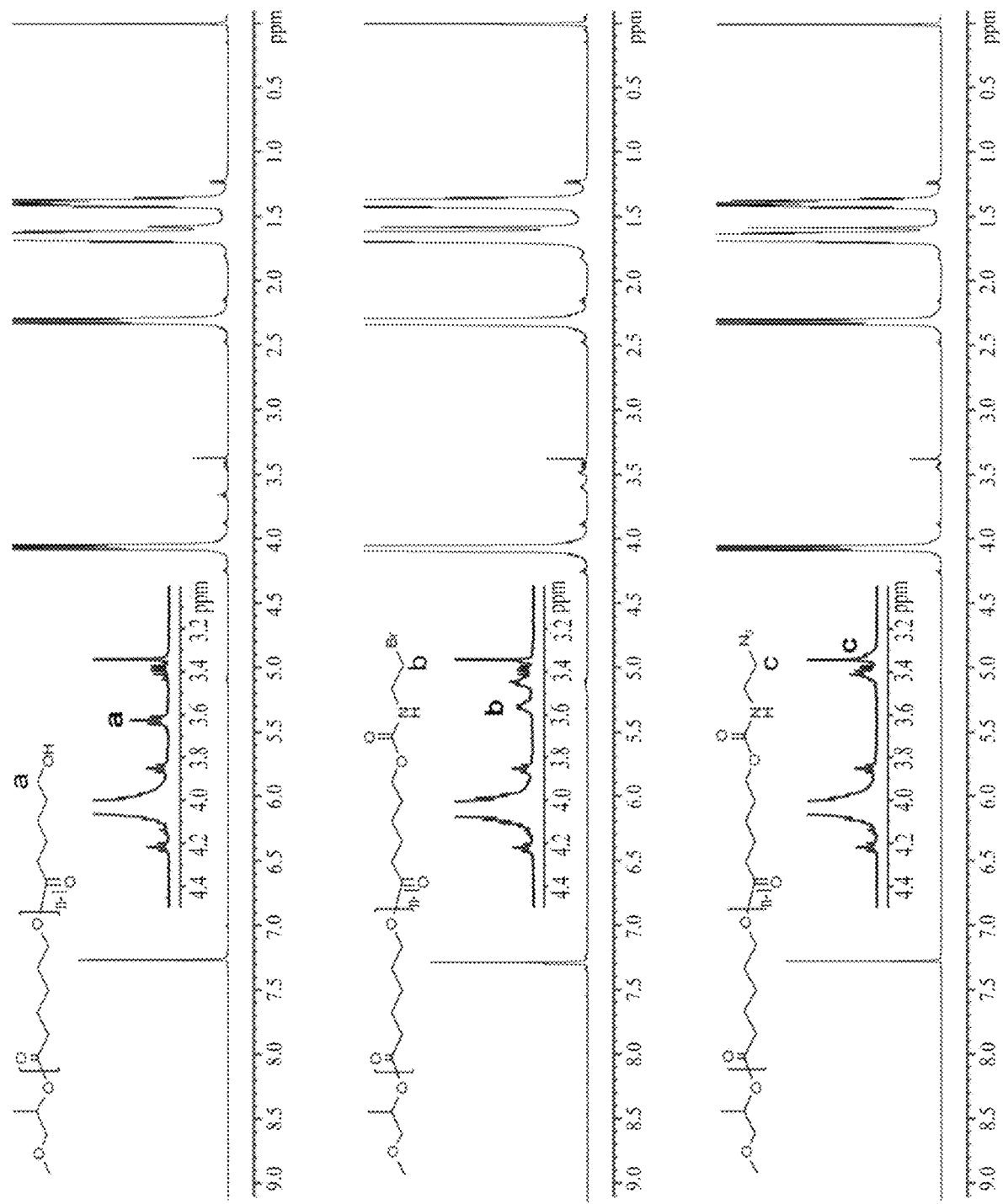

The terminal hydroxyl groups of both PCL3.5K and PCL14K were completely substituted into a tosyl group and bromide, respectively (FIG. 15). The identical method for both molecular weights of PCL was first attempted, however effective substitution was not observed for high molecular weight PCL with p-toluenesulfonyl chloride and the alternative method was chosen due to the high reactivity of the isocyanate group with hydroxyl groups as well as the ease of nucleophilic substitution of bromine for azide.

G3 polyester dendron bearing an acetylene functional group at the focal point was reacted with PCL-N$_3$ via click chemistry. Although click chemistry has been shown to be efficient under mild conditions, a variety of reaction conditions have been developed that vary in terms copper species, bases, solvents and temperatures further increase conjugation yields.[47] The click reaction between PCL-N$_3$ and G3 dendron was firstly catalyzed by 0.2 equivalent amounts of CuBr and PMDETA based on the feed molar amount of PCL-N$_3$ in DMF at room temperature as previously reported.[48] However, the conjugation yield was calculated to be less than 10% by $^1$H-NMR with no appearance of characteristic protons associated with triazole formation. According to few reports on the failure of click reactions,[49] we investigated the efficiency of the click reaction with a variety of conditions; copper species (CuSO$_4$, CuBr, CuI), sodium ascorbate, bases (PMDETA, diazobicyclo[5.4.0undec-7-ene]), solvents (DMF and THF), temperatures (30, 50, and 80° C.). It was found that the click reaction using CuBr and PMDETA in DMF at 80° C. afforded the desired PCL-G3 products with high conjugation yields (PCL3.5K-G3: 70%; PCL14K-G3: 80%).

Micelle Preparation and Characterization

For blank micelles, 20 mg of polymer was dissolved in 2 mL of dimethylformamide. The solution was dialyzed (MWCO 3.5K) against distilled water for 1 day and freeze dried for 2 days. IMC was chosen as a model hydrophobic drug. IMC-loaded micelles were prepared by a dialysis method. 40 mg of polymer was dissolved in 4 mL of dimethylformamide along with 4 mg of IMC. The polymer-IMC solution was then transferred to a dialysis membrane (MWCO 3500), dialyzed for 24 h against 2 L of distilled water, and freeze dried for 2 days to produce IMC-loaded micelles.

Figure 16:
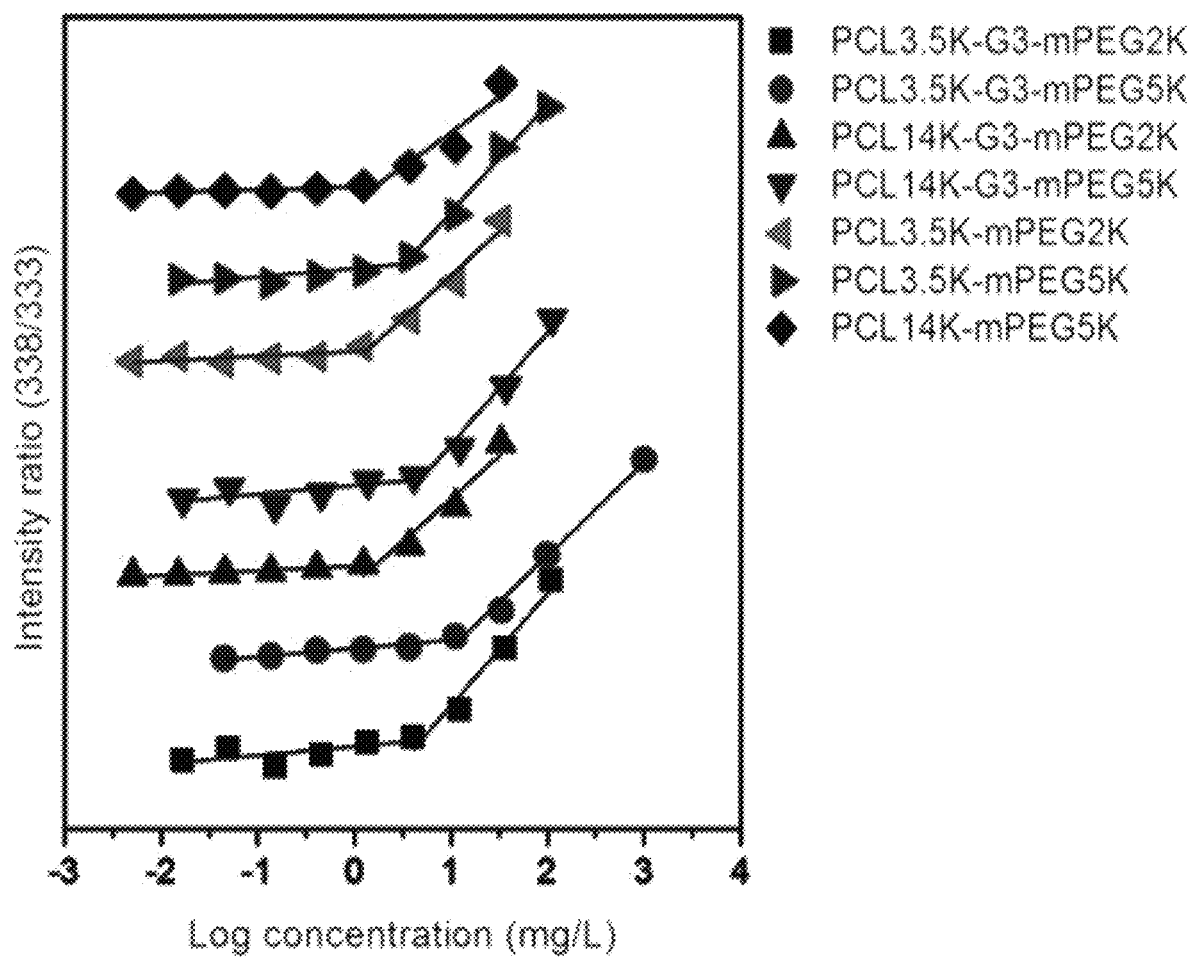
FIG. 16 shows plots of fluorescence intensity ratios against log concentrations of copolymers. The transition points indicate the CMC results of various PCL-G3-mPEG and PCL-mPEG copolymers.
Figure 17D:
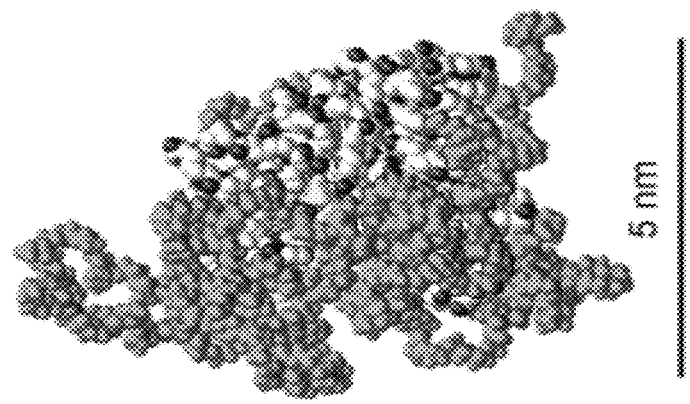
FIGS. 17A-17E show equilibrated conformations of individual (Panel A) PCL3.5K-mPEG2K, (Panel B) PCL3.5K-mPEG16K, (Panel C) PCL3.5K-G3-mPEG2K, and (Panel D) PCL14K-G3-mPEG2K molecules in water (PCL shown in white/black; G3-dendron: hidden in middle in Panel C and D; PEG shown in grey). These structures represent the in-solution morphology of each individual copolymer when they are not packed into micelles. Water is not shown for clarity. Panel E shows equilibrated conformations of the individual PCL3.5K-G3-mPEG2K copolymers in the PCL3.5K-G3-mPEG2K micelle with 14 copolymers taken from FIG. 11 (Panel A).
Figure 17C:
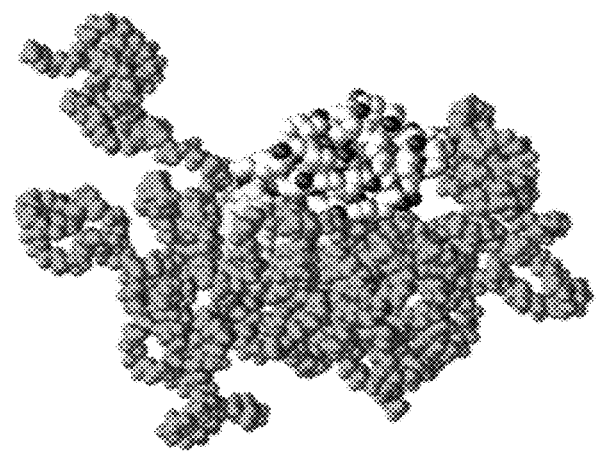
Figure 17B:
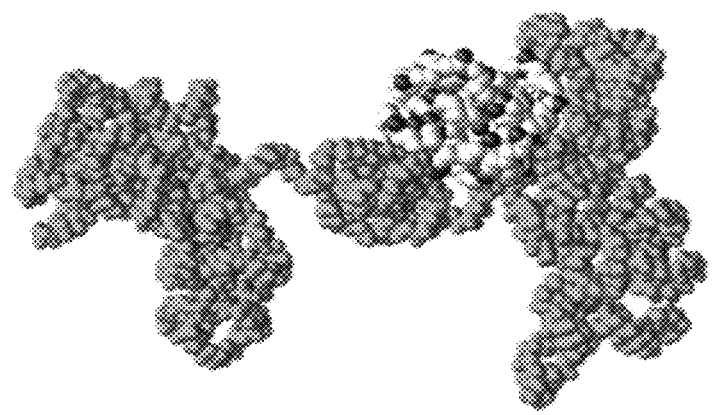
Figure 17A:
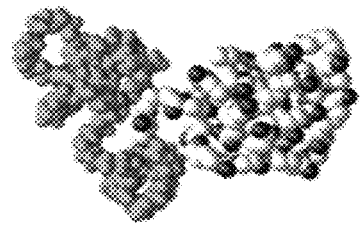
Figure 17E:
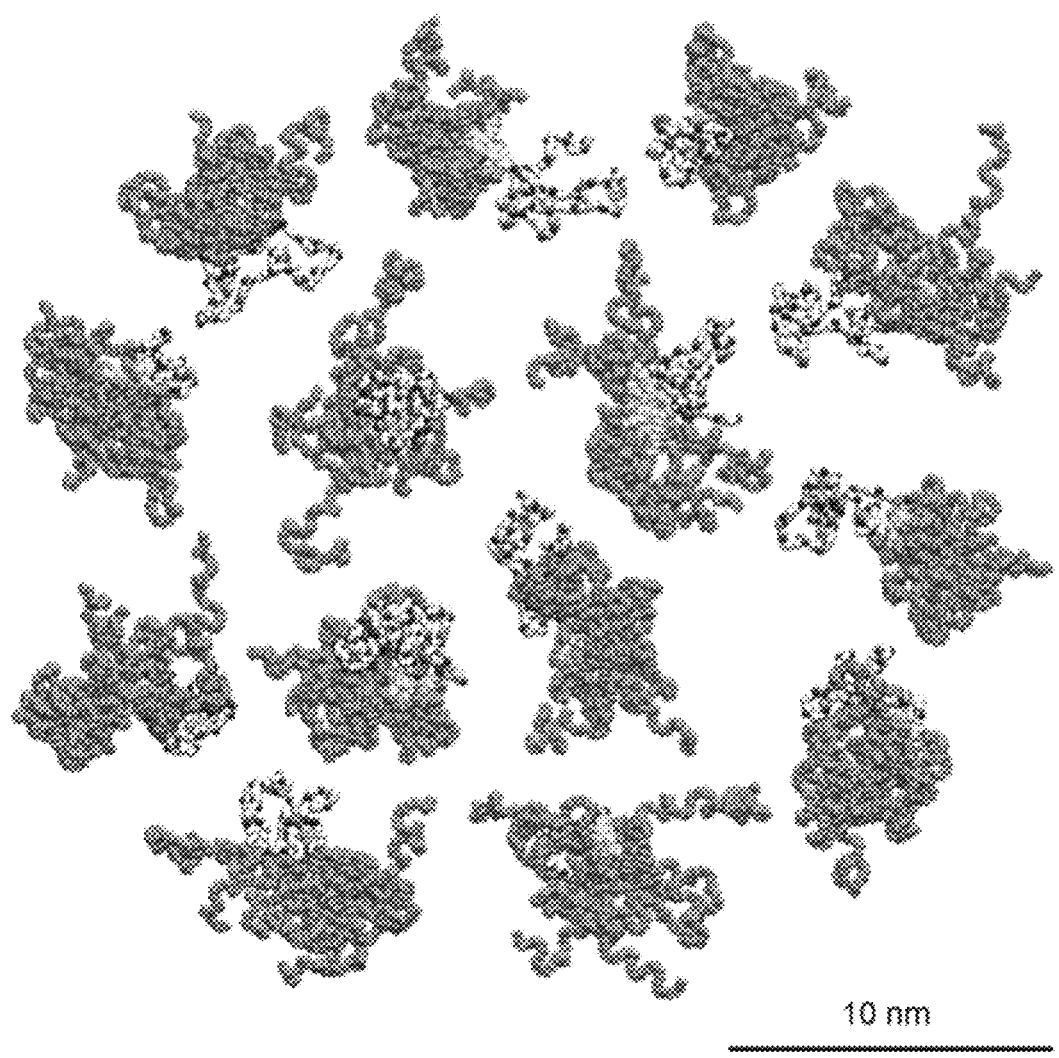

Critical micelle concentration (CMC) was determined by using a fluorescence method as previously reported.[50] Briefly, a known amount of pyrene dissolved in acetone was added to a series of vials and evaporated such that upon addition of 2 mL of polymer solution the concentration of pyrene was 6×10$^{-7}$ M. The copolymers dissolved in water (10$^3$-10$^{-3}$ mg/L) was added to each vial containing pyrene and before fluorescence measurement the solutions were vortexed and incubated at room temperature for 24 h. The emission wavelength $\lambda_{em}$ was set at 390 nm and the $\lambda_{em}$ was scanned from 300 nm to 400 nm using a spectrofluorophotometer (RF 1501, Shimadzu, Japan) and the intensity ratio $I_{338}/I_{333}$ against log concentration was plotted. See FIG. 16.

The particle size (nm) and size distribution were measured for all micelles by dynamic light scattering (DLS) using a Nicomp 380 Zeta Potential/Particle Sizer (Particle Sizing Systems, Santa Barbara, Calif.). Micelles were prepared at concentrations above their measured CMCs in distilled water, filtered through a 0.45 μm syringe filter, and vortexed briefly before each measurement. The micellar morphology was analyzed by transmission electron microscopy (TEM, JEM-1220, JEOL Ltd., Japan). A drop of micellar suspension (0.2 mg/ml) after filtration (pore size, 0.45 μm) was placed on a 300 mesh copper grid coated with carbon. The sample was stained with a drop of 2% phosphotungstic acid and dried at room temperature in a desiccator for 1 day. The diameters of each micelle were measured by randomly selected 10 particles from each TEM image. The average and standard deviation were calculated.

Drug Release Test

To determine the IMC-loading content, a small amount of IMC-loaded micelles was dissolved in 1 mL of dimethylformamide and the concentration of IMC was determined by measuring the UV-absorbance at 317 nm from a series of IMC standards in dimethylformamide. 10 mg of IMC-loaded micelles was suspended in 1 mL of PBS (pH 7.4, 0.01 M) and transferred to a dialysis bag (MWCO 3.5K). Each dialysis bag was added to 30 mL of PBS and placed into a shaking water bath (37° C., 50 rpm). At predetermined time intervals, 10 mL of release medium was removed and replaced with fresh PBS and frozen until all samples were collected. Samples were then freeze-dried for 2 days, redissolved in 1 mL DMSO and centrifuged at 4000 rpm at room temperature. The amount of IMC released was obtained by measuring the UV-absorbance of the supernatant at 317 nm and comparing to a standard curve of IMC in DMSO. The release profile was obtained by plotting the cumulative IMC release against time.

Cytotoxicity Test

KB cell line was obtained from ATCC (Manassas, Va., USA) and grown continuously as a monolayer in GIBCO RPMI 1640 medium (Invitrogen Corporation, Carlsbad, Calif., USA) in a humidified incubator at 37° C. and 5% $CO_2$. RPMI was supplemented with penicillin (100 units/ml), streptomycin (100 mg/ml), and 10% heat-inactivated fetal bovine serum (FBS) (Invitrogen Corporation, Carlsbad, Calif., USA) before use. For the assay, KB cells were seeded in 96-well plates at a density of $5 \times 10^3$ cells/well and grown in RPMI for 24 h. Cells were then treated with different concentrations of each copolymer ranging from 0.01-100 µM. After each incubation time, cells were washed and incubated for an additional 24 h. Cell viability was assessed using a CellTiter 96 AQueous One Solution (MTS) Assay (Promega, Madison, Wis., USA) according to the manufacturer's protocol. The UV absorbance was measured at 490 nm using a Labsystems Multiskan Plus microplate reader (Labsystems, Finland). Mean cell viabilities were determined relative to a negative control (untreated cells) and a positive control (0.1% Triton-X, Sigma-Aldrich).

Modeling of the Monomer Self-Assembly

We modeled by atomistic molecular dynamics (MD) simulations individual linear, PCL3.5K-mPEG2K and PCL3.5K-mPEG16K, and branched, PCL3.5K-G3-mPEG2K and PCL14K-G3-mPEG2K copolymers in water. Separately, we modeled micellar assemblies of hydrated PCL3.5K-mPEG2K, PCL3.5K-G3-mPEG2K, and PCL14K-G3-mPEGK copolymers with different aggregation numbers, $N_{agg}$. We used the NAMD package[51] and the CHARMM force field (CHARMM27, C35r revision for ethers, and general force field).[52] In all the simulations, the Langevin damping constant of $\gamma_{Land}=0.01$ $ps^{-1}$ was used to achieve a faster relaxation. Non-bonded interactions were calculated using the cut-off distance of d=12 Å. Long-range electrostatic interactions were calculated by the PME method[53] and the MD integration timestep was set to 2 fs.

The individual copolymer molecules were solvated and equilibrated for ~5-7 ns in TIP3P water, using the NPT ensemble (VMD)[54], with periodic boundary conditions applied (P=1 bar and T=300 K). The obtained results are shown in FIG. 2b. We also studied the conformations of individual copolymers fully equilibrated in water, using the same conditions. In the equilibration of PCL3.5K-mPEG2K, PCL3.5K-mPEG16K, PCL3.5K-G3-mPEG2K and PCL14K-G3-mPEG2K, a force of F=0.01 kcal/mol/A was applied to several atoms of the PEG chains, directing toward the hydrophobic PCL core. After ~0.2 ns, the PEG chains were collapsed on the hydrophobic cores. Then, we stopped the force and equilibrated the monomers for another 10 ns. The equilibrated conformations of the copolymers are shown in FIG. 17 (Panels A-D). FIG. 17 (Panel E) shows equilibrated conformations of the individual PCL3.5K-G3-mPEG2K copolymers in the PCL3.5K-G3-mPEG2K micelle with 14 copolymers taken from FIG. 11 (Panel A). Each of the 14 copolymers that form the micelle was translated from their packed configuration and otherwise was not changed. The packed morphology of each of the PCL3.5K-G3-mPEG2K copolymers changes from the largely globular shape, as observed in FIG. 17 E, to a significantly conical shape, resembling those in FIG. 11 (Panel A). This conformational change aids in the formation of spherical self-assemblies with fully PEGylated surfaces, as observed in FIG. 11 (Panel A).

Figure 18:
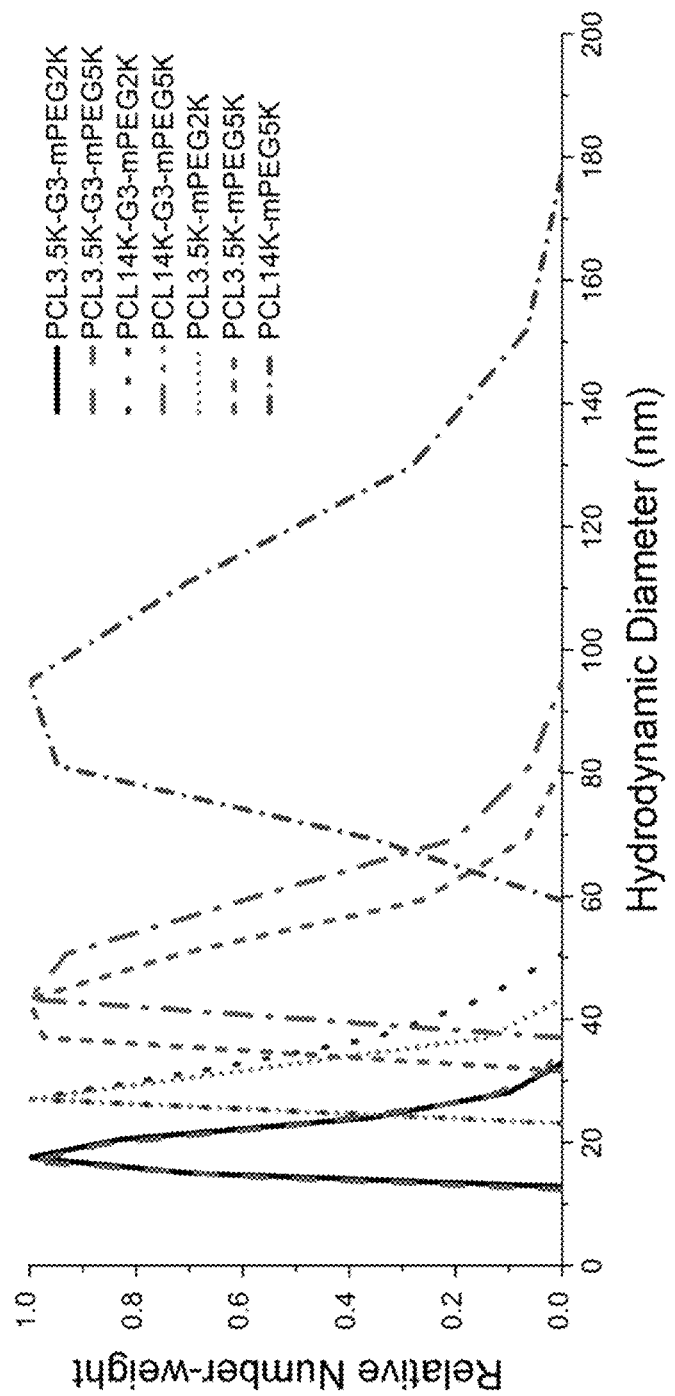
FIG. 18 shows measurements of hydrodynamic diameter using dynamic light scattering (DLS): PCL3.5K-G3-mPEG2K (18.6±3.5 nm); PCL3.5K-G3-mPEG5K (18.3±3.7 nm); PCL14K-G3-mPEG2K (30.3±4.9 nm); PCL14K-G3-mPEG5K (49.8±8.3 nm); PCL3.5K-mPEG2K (29.4±3.2 nm); PCL3.5K-mPEG5K (44.4±9.4 nm); PCL14K-mPEG5K (94.6±16.3 nm).

In the study of micellar assemblies, the monomers were initially spherically distributed by our codes and hydrated in cells containing 30,000-530,000 atoms, with periodic boundary conditions applied. After short minimizations, the systems were heated to T=400 K for fast reorganization, while the volume was kept constant. At the same time, the central force of $\vec{F}(\vec{r})=k\vec{r}$ with k=1.0 kcal/mol/A was applied to several atoms along the PCL chains of all the copolymers, in order to accelerate aggregation of the micellar core. After 1 ns, the systems were cooled to T=300 K, and equilibrated at P=1 bar for ~4-5 ns. The obtained micelles are shown in FIG. 3b. In order to better understand the conformations of individual PCL3.5K-G3-mPEG2K molecules self-assembled in the micelle, we disintegrated the 14 PCL3.5K-G3-mPEG2K micelle using VMD[11] without changing the conformation of the individual copolymer, as shown in FIG. 18.

We also estimate the approximate entropic cost in the self-assembly of linear monomers, where it is assumed that PEG chains can be described as ideal chains.[55] An ideal chain of length L is comprised of n segments of statistical length l, so that L=ln. When placed in a good solvent (such as water), the ideal chain swells to maximize the number of polymer-fluid contacts. Configurations of the ideal chain can be characterized by a probability distribution function that depends on the chain end-to-end (e-t-e) distance. An ideal chain has a well-defined average e-t-e distance $<r>=ln^{1/2}$, which is associated with minimum (configuration) free energy of the polymer. When the ideal (PEG) chain becomes confined during the self-assembly process, its average e-t-e distance will increase and the free energy cost associated with this extension is purely entropic. Entropy of a freely jointed chain with a given e-t-e distance is proportional to the logarithm of the number of chain configurations for that e-t-e distance. This is in turn is proportional to the probability of the PEG having this e-t-e distance. The entropy difference between PEG chains in a given conformation with different e-t-e extensions is given by[55] $\Delta S=S-S_1=k_B b^2(r_1^2-r^2)$, where S and $S_1$ are configurational entropies associated with the e-t-e extensions r and $r_1$, $k_B$ is the Boltzmann constant and $b^2=3/(2nl^2)$. For PCL3.5K-mPEG16K, the PEG block has n=363 repeating unts ($-CH_2CH_2O-$), each of the length l is approximately 3.68 Å. In water, the average e-t-e distance of this polymer is $<r>=ln^{1/2}\approx 70$ Å. If we assume that due to steric confinement the e-t-e distance of the chains in the micelle is extended by 50% from the above value of $<r>$, the entropic cost for this extension is $\approx 1.11$ kcal/mol$\approx 1.9$ $k_B T$. Since every chain forming a micelle needs to pay this configurational entropy cost, the micelle formation is not favorable for polymers with long hydrophilic blocks, but in short chains attached to dendrons this entropic costs is absent. We can use the fact that the Gibbs energy associated with the monomer self-assembly is given by $\Delta G=\Delta H-T\Delta S$, where $\Delta H$ is the related enthalpy change. We can immediately see that, for the same $\Delta H$ (hydrophobic binding in the core), long linear amphiphilic molecules tend to be less stable when self-assembled (ΔS>0) than branched dendron-based amphiphilic molecules (ΔS~0).

Example 3

Alpha-mangostin was encapsulated into PCL3.5K-G3-mPEG2K micelles.

A solution of PCL3.5K-G3-mPEG2K and α-mangostin (15% w/w; 15 mg drug/100 mg polymer) was prepared at 10 mg polymer/mL in DMF. The solution was dialyzed for 1 day against a 3.5 KDa membrane in 500 mL $dH_2O$ for each 10 mg of polymer with repeated water changes to remove unencapsulated α-mangostin. After dialysis, the dialysate was centrifuged for 10 min at 4000 RPM to remove any unencapsulated α-mangostin. The supernatant was then collected and lyophilized for 2 days to yield the α-mangostin encapsulated micelles.

Figure 19B:
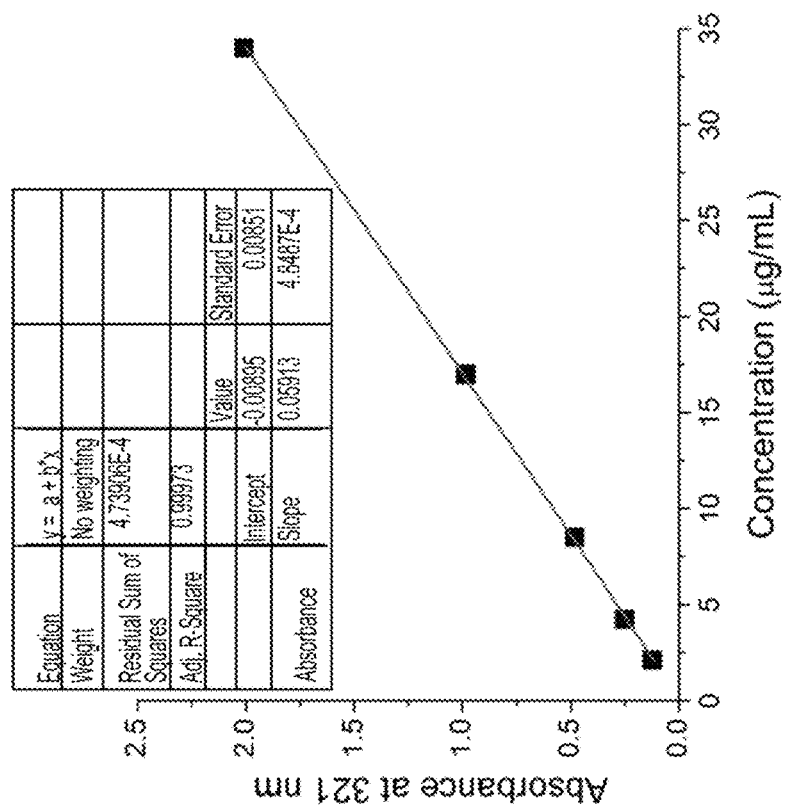
FIGS. 19A-19B show in Panel A, UV/Vis spectra of alpha-mangostin-loaded dendron micelles and free apha-mangostin, and in Panel B, standard curve based on the UV spectra of free alpha-mangostin. The loading amounts of alpha-mangostin in micelles were calculated based on the standard.
Figure 19A:
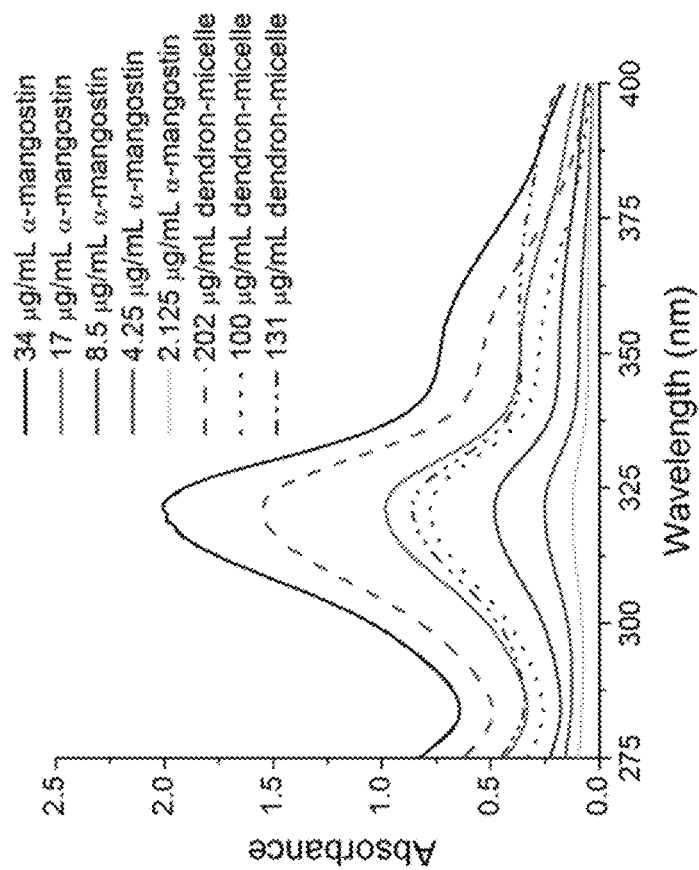

UV/Vis (FIG. 19), loading efficiency and encapsulation efficiency were then calculated. The loading percentage was 12.49±1.2 where Loading %=(Measured α-MS amount/Mass of α-MS loaded micelle)×100(%), while the encapsulation percentage was 83.5±7.7 where Encapsulation (%)= (Measured α-MS amount/Theoretical α-MS loading amount)×100(%).

Figure 20:
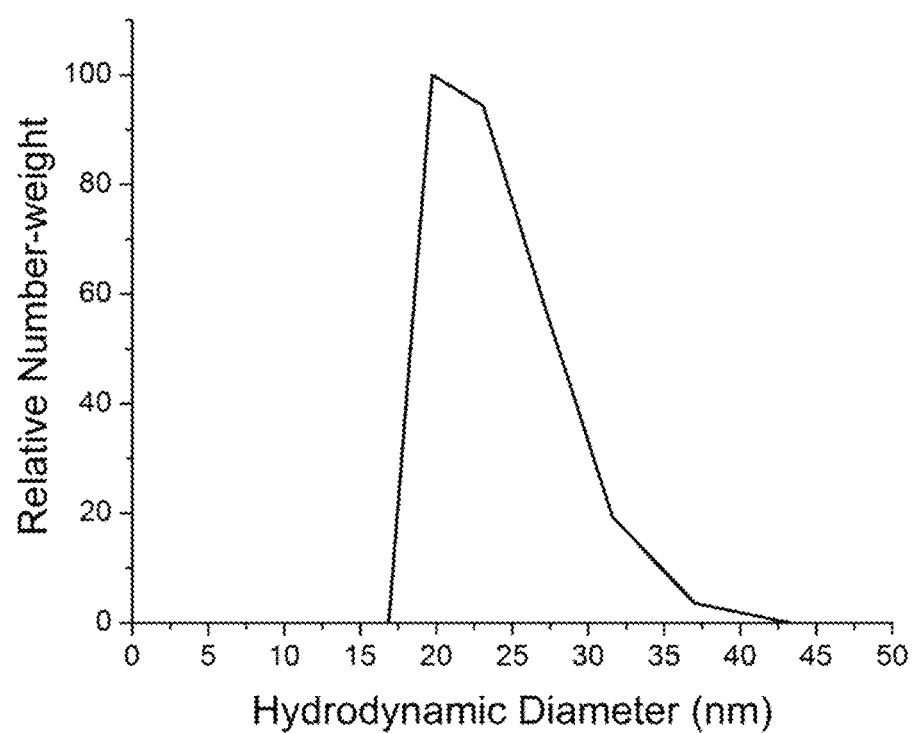
FIG. 20 shows the size distribution of the alpha-mangostin-loaded dendron micelles measured by Dynamic light scattering (DLS).

Next, dynamic light scattering (DLS) analysis of 15% w/w α-mangostin PCL3.5K-G3-mPEG2K micelle (22.7±3.6 nm) was then analyzed. One mg of 15% α-mangostin drug loaded micelles was dissolved in 1 mL of ddH20 and measured by DLS without filtration. The results are shown in FIG. 20.

Figure 21:
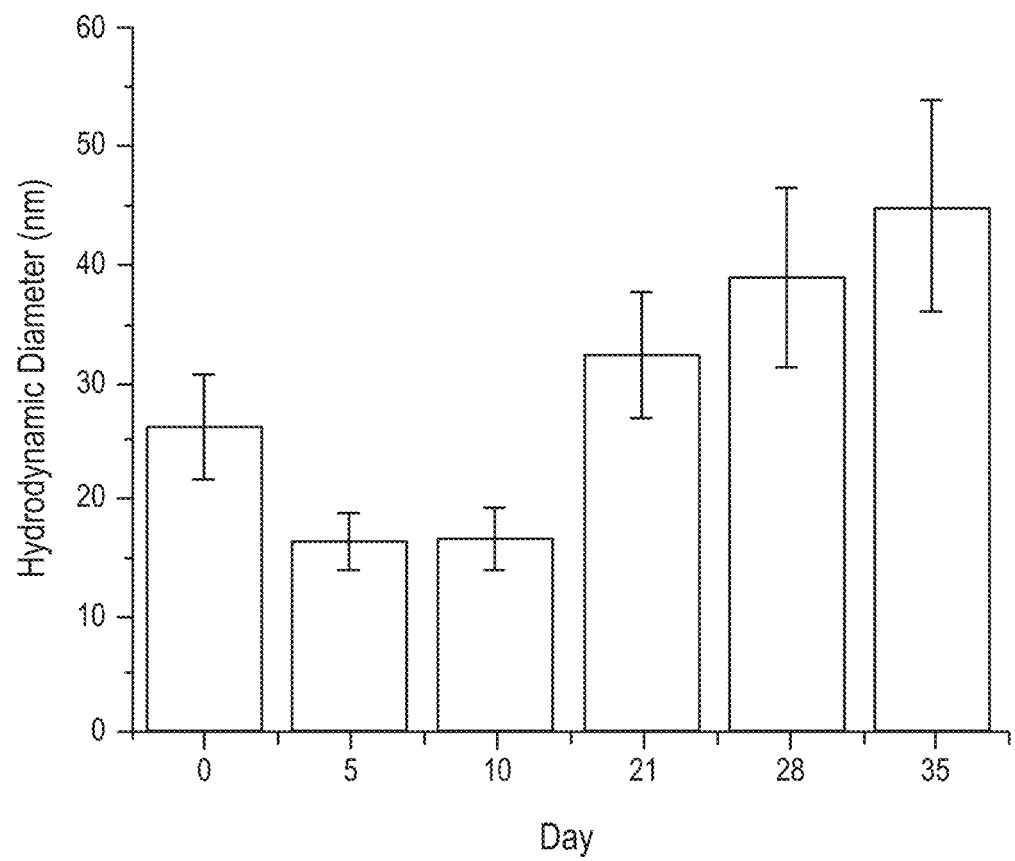
FIG. 21 shows changes in size of the alpha-mangostin-loaded dendron micelles measured by DLS.

Finally, the α-mangostin drug loaded micelles were tested for stability. One mg of 15% α-mangostin drug loaded micelles was dissolved in 1 mL of ddH20 and filtered through a 0.45 um syringe filter. At certain times, the size of the micelles was measured by DLS. The results are shown in FIG. 21.

Example 4

Figure 22:
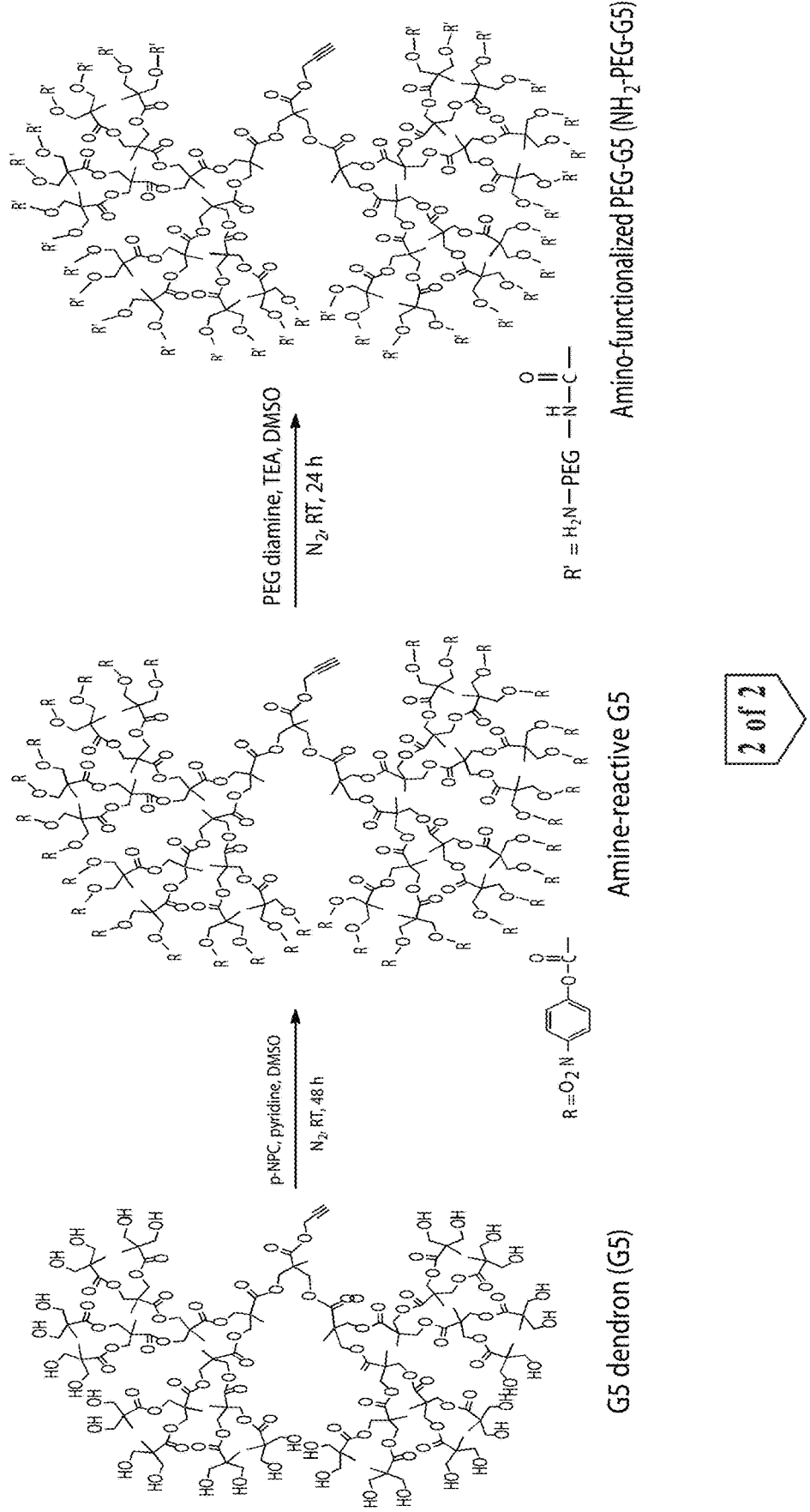
FIG. 22 shows an example of a synthetic route to prepare FA-conjugated amphiphilic dendron.

FA-conjugated PEG-G5-PCL was prepared in four steps as shown in FIG. 22.

Step 1. Amino-functionalized PEG-G5. G5 dendron (20 mg, 5.47 µmol) and pyridine (138 mg, 1.75 mmol) were dissolved in 10 ml of DMSO and p-NPC (353 mg, 1.75 rnmol) was dropwise added to the above solution. The reaction was carried out for 48 h at room temperature under nitrogen atmosphere. The solution was transferred to a pre-swollen membrane (Spectra/Por, MWCO 3.5K), dialyzed against distilled water for 24 h and subsequently lyophilized. To PEG diamine (64-folds. molar excess over activated G5) and TEA (128-fold molar excess over activated G5) dissolved in 20 ml of DMSO, the activated G5 solution was dropwise added and then reacted for 24 h at room temperature under nitrogen atmosphere. After the reaction, the amino-functionalized PEG-G5 was obtained through the same procedure above.

Step 2. Acetylation and FA conjugation of PEG-G5. Both acetylation and FA conjugation on the amino-functionalized PEG-G5 dendron were sequentially performed as previously reported. At first, the PEG-G5 dendron were partially acetylated by reacting with acetic anhydride in anhydrous methanol in the presence of TEA. The reaction was carried out for 24 h at room temperature. The resulting mixture was dialyzed (MWCO 3.5K) first in phosphate buffer at pH 8.0 and then in deionized water. The purified samples were lyophilized and stored at −20° C. For FA conjugation, the obtained product was dissolved in 10 ml of DMSO and the mixture of FA (10 molar excess over dendron) and EDC (10 molar excess over FA) was added dropwise. The conjugation was carried out for 24 h at room temperature under nitrogen atmosphere. After dialysis and lyophilization, FA-PEG-G5 was obtained.

Step 3. Azido-functionalized PCL. Both PCL (0.5 g, 0.013 mmol) and p-toluenesulfonyl chloride (10 mg, 0.091 mmol) were dissolved in 50 ml of methylene chloride. Then, TEA (18 mg, 0.182 mmol) was added dropwise to the mixture and the reaction was performed for 24 h at room temperature under nitrogen atmosphere. The solution was precipitated into cold methanol and dried in vacua. Tosylated PCL was converted into the azido-functionalized PCL. Sodium azide (10-fold molar excess over tosylated PCL) was added to a solution of tosylated PCL in DMF under nitrogen atmosphere and the reaction was carried out for 24 h at room temperature. DMF was removed using a rotary evaporator and the product was dissolved in methylene chloride and precipitated into cold methanol to give the azido-functionalized PCL.

Step 4. FA-conjugated PEC-G5-PCL. FA-conjugated PEG-G5-PCL was synthesized by coupling azido-PCL to acetylene-dendron via click chemistry. FA-conjugated PEG-G5 was dissolved in 10 ml of dry DMF. After adding CuBr and PMDETA as catalysts, a solution of $N_3$-PCL was added and reacted for 24 h at room temperature. DMF was evaporated completely and the solution was then dissolved in methylene chloride. The solution was precipitated into cold methanol, dried in vacua and stored at −20° C. before use.

Feed ratio: PCL-N3/FA-PEG-G5/CuBr/PMDETA=1/1/0.2/0.2

Example 5

Supramolecular Structures of Dendron-Based Nanomicelles

Dendron-based nanomicelles (DNM) as a novel targeted drug delivery platform will be prepared by four synthetic procedures; 1) PEGylation of dendron, 2) Conjugation of targeting ligands, 3) Azido-functionalization of a hydrophobic tail, 4) Preparation of amphiphilic dendron via click chemistry. Each step will be further optimized to control the desired properties of nanomicelles for enhanced therapeutic efficiency. By controlling a relative balance between hydrophobic and hydrophilic components, the obtained amphiphilic dendron (AD) molecules can form various unique structures via self assembly. In one application, the micellar structure of AD will be formed at concentrations above the critical micelle concentration (CMC) under aqueous solutions.[56-58] The copolymer composed of hydrophilic dendron and hydrophobic polyester dissolves in an organic solvent with drugs to be encapsulated. Then, DNMs formed by a dialysis method will he physicochemically characterized and its therapeutic efficacy will be evaluated in vitro and in vivo.

Other supramolecular structures such as gold nanaparticles decorated with functionalized dendrons can be prepared by spontaneous alignment of thiol-contained molecules onto the surface of gold nanoparticles.[59] In order to achieve this surface functionalized nanostructure, an acetylene group of the dendron needs to be modified with heterobifunctional PEG, which possesses both azide and thiol at each end, via click chemistry. Then, the self-assembly layers on the nano-sized gold colloids are formed spontaneously in ethanol solution in the presence of dendron-PEG-SH. Either a vesical or a cylindrical nanostructure can be also created by conjugation of hydrophobic molecules to the dendron. In case of a vesicle type, a longer hydrophobic tail should be chemically attached to a focal point of dendron already functionalized with specific ligands, which allows strong hydrophobic interactions. Based on the estimated size of the dendron head group and the hydrophobic length according to the theory of Israelachvili et al.[60], the supranaolecular architecture of these AD molecules eventually results in the formation of lipid bilayers.[58] A cylindrical shape has a similar aspect but hydrophobic modification should be carried out at the peripheral site of the dendron. Consequently, controlling the ratio of the hydrophobic length to the hydrophilic dendron can lead to cylindrical packing.[61] These two switchable features formed via self-assembly are typically dependent on the hydrophobic block length toward two reactive ends of the dendron (either core or periphery).

Example 6

Dendron Micelles as a Transdermal Dendron Delivery Platform

The dendron micelles are contemplated for use as a transdermal drug delivery platform of hydrophobic drugs, for example, for delivering EDX. As described in the following examples, EDX-loaded dendron micelles enhanced EDX skin permeation, water solubility/stability, and a controlled release profile without a cost of its efficacy compared to free EDX. The skin permeation efficiency of EDX delivered by the dendron micelles was compared to delivery by cationic liposomes and a traditional CPE (ethanol) using both hairless mouse and human skin samples. Finally, the surface charge effect of the dendron micelles on drug loading, in vitro drug release, and skin permeation by modulating the end-group functionalities of the micelles was demonstrated. The data indicate that the dendron micelles have great potential as a novel platform for controllable topical delivery of EDX, which can be also applied for other skin impermeable drug molecules.

Materials and Methods

Materials

EDX (N-Desmethyl-4-hydroxy Tamoxifen, $M_w$ 373.49, E/Z 1:1 mixture) was purchased from Toronto Research Chemicals Inc. (North York, Ontario, Canada). 1,2-dioleoyl-3-trimethylammonium-propane (DOTAP, $M_w$ 698.54), 1,2-dimyristoyl-sn-glycero-3-phosphocholine (DMPC, $M_w$ 677.93), and Cholesterol ($M_w$ 386.65) were obtained from Avanti® Polar Lipids, Inc. (Alabaster, Ala.). Surface modified PEGylated dendron-based copolymers (PDC) and their respective micelles (M-(end group)) were prepared in Hong lab as described previously with the following end-groups (—$NH_2$, —COOH, and —Ac)[86] {Pearson, 2012 #304}. Coumarin-6 (Cou6), J3-estradiol (E2), and all the solvents for chemical reactions, including dimethylformamide (DMF), dimethyl sulfoxide (DMSO), dichloromethane (DCM) and methanol were obtained from Sigma-Aldrich (St. Louis, Mo.) and used as received. Surface modification of PCL-G3 dendrons and preparation of RHO-labeled PCL-G3 dendrons are described in ACS Macro Lett., 2013, 2(1), 77-81.

Preparation of EDX-Loaded Micelles with Different Surface Functional Groups

EDX-loaded micelles were prepared by a dialysis method[86]. Briefly, ten milligrams of the surface modified PDC was dissolved in 1 mL (10 mg/mL) of DMF along with 1.5 mg of EDX. The polymer-EDX mixture was then transferred to a dialysis membrane (MWCO 3500) and dialyzed for 24 h against 500 mL of double distilled water ($ddH_2O$). After dialysis, the micelle solution was collected into 1.5 mL centrifuge tubes and centrifuged at 10,000 rpm for 5 min at 25° C. The supernatant was carefully collected and freeze-dried for 2 days to obtain the EDX-loaded micelles.

Preparation of EDX-Loaded Cationic Liposomes

EDX-loaded liposomes were prepared by a thin film hydration method[93]. DOTAP (4.45 mg), DMPC (4.32 mg), Cholesterol (1.23 mg) (2:2:1 molar ratio) and EDX (1.5 mg) were dissolved in 1 mL of chloroform. The solvent was evaporated using a rotary evaporator until the materials formed a thin, dried film at the bottom of the round-bottom flask. Two milliliters of $ddH_2O$ were added to rehydrate (completely re-dissolve) the lipid film by vortexing at high intensity. The rehydrated materials were then sonicated for 30-60 min in a water bath sonicator. The size of the liposome was further refined by extrusion 40 times through a polycarbonate membrane (pore size 100 nm) at 40 psi. The liposome was then collected into 1.5 mL centrifuge tubes and centrifuged at 13,000 rpm for 30 min at 4° C. The supernatant was carefully collected and stored in a separate tube for characterization. The liposome pellet was re-suspended in 1 mL of 5% sucrose/water solution for lyophilization (1 day).

Preparation of Cou6-Encapsulated, Rhodamine(RHO)-Labeled (Two-Dye) Dendron Micelles with Different Surface Functional Groups To prepare two-dye dendron micelles, two milligrams of acetylated, RHO-labeled PDC (PDC-RHO-Ac) was combined with 10 mg of unlabeled surface modified PDC in 1.2 mL DMF, and 2% (wt %) of Cou6 was added to the mixture. The materials were fully dissolved and mixed by brief vortexing followed by gentle shaking for 2 h. The Cou6-encapsulated, RHO-labeled dendron micelles were prepared by the dialysis method, and the solid material was obtained by lyophilization as described above.

Characterization of Drug-Loaded Micelles and Liposomes Using Dynamic Laser Scattering (DLS), Transmission Electron Microscope (TEM) and HPLC Particle size (diameter, nm) and surface charge (zeta potential, mV) of the EDX-loaded micelles and liposomes were obtained from three repeat measurements by quasi-elastic laser light scattering using a Nicomp 380 Zeta Potential/Particle Sizer (Particle Sizing Systems, Santa Barbara, Calif.). The materials were dispersed in $ddH_2O$ to a concentration of 500 μg/mL and briefly vortexed prior to the measurement.

The micelle morphology was also analyzed using TEM (JEM-1220, JEOL Ltd., Japan). A drop of micelle suspension (0.20 mg/ml) after filtration (pore size 0.45 μm) was placed on a 300 mesh copper grid coated with carbon. The sample was stained with a drop of 2% phosphotungstic acid and dried at room temperature in a desiccator for 1 day. The diameter of each type of micelle was measured using 10 randomly selected particles from each TEM image. The average and standard deviation were calculated.

Drug loading was determined using a reversed-phase (RP) HPLC. One hundred micrograms of the lyophilized micelles were dissolved in 1 mL of DMSO, followed by vortexing and 6 h of incubation at room temperature with gentle shaking before measurement. Serially diluted EDX (9.77, 19.53, 39.06, 78.13, 156.25 and 312.50 ng/mL) solutions in DMSO were prepared and used to plot the standard curve for the quantification of drug loading using RP-HPLC. All samples were filtered through 0.20 gm Teflon syringe filters. A CHIPhEarser (Jelight Co., Inc., CA) was used as a pre-column photochemical reactor to convert endoxifen into its fluorescent derivatives at 254 nm. Ten microliters of each sample were injected into a Symmetry C18 column (3.5/5 gm, 4.6×150 mm, Waters, Milford, Mass.) connected to a Waters HPLC system composed of a 717 Autosampler and a 600E series pump under isocratic mode. The mobile phase was composed of 46% (v/v) acetonitrile and 54% (v/v) $KH_2PO_4$ buffer (20 mM, pH 3.0). The flow rate was maintained at 1 mL/min. The column temperature was set at 25° C. EDX was detected at 254 nm excitation and 390 nm emission wavelengths using a Waters 474 Fluorescence detector. Loading was expressed as micrograms of EDX per milligram of micelle or liposome (gg EDX/mg micelle or liposome). Loading efficiency was calculated from the ratio of the actual measured loading to the theoretical loading (For micelles, the theoretical loading was the amount of EDX added divided by the mass of each PDC used in the formulation[17]. For liposomes, the theoretical loading was the amount of EDX added divided by the mass of lipids plus sucrose used in the formulation)[81].

In Vitro Drug Release Test

The drug release test was performed using a vertical Franz diffusion cell device (D7 mm with 0.38 $cm^2$ exposure area, PermeGear Inc., Hellertown, Pa.). A cellulose membrane (MWCO 3.5K) was sandwiched between the donor and receiver chamber. Micelles and liposomes loaded with the same amount of EDX were suspended in $ddH_2O$ and 100 III, were applied to each donor chamber. The receiver solution (release media), composed of 30% ethanol and 70% normal saline, was stirred constantly at 600 rpm and the temperature was maintained at 37° C. At predetermined time intervals, 250 gL of release medium were removed and replaced with an equal amount of fresh receiver solution and analyzed using RP-HPLC with the same conditions as described above. The release profile was obtained by plotting the cumulative EDX release % against time.

In Vitro Anti Proliferation Assay Against Breast Cancer Cells

The ER-positive human breast carcinoma cells, MCF-7 (American Type Culture Collection, ATCC, Manassas, Va.), were maintained in Dulbecco's modified Eagle's medium (DMEM, Mediatech, Inc., VA) supplemented with 10% (v/v) fetal bovine serum (Invitrogen™) and 1% (v/v) penicillin/streptomycin in a humidified incubator at 37° C. and 5% $CO_2$. When the cell monolayers were approximately 70% confluent, the culture medium was replaced with an estrogen-depleted medium (stripped medium) consisting of phenol-red free DMEM (Mediatech, Inc., VA) supplemented with 10% (v/v) charcoal-stripped fetal bovine serum (Invitrogen™), 1% (v/v) 200 mM L-Glutamine, and 1% (v/v) penicillin/streptomycin under the same incubation conditions mentioned above. To remove any residual estrogen, the monolayer was washed and replenished with fresh stripped medium every day for 3 days; when cells were >90% confluent, the monolayer was detached from the cell culture flask with phenol red-free trypsin and counted using a hematometer. Cells were seeded onto a 96-well plate at a concentration of 4,000 cells per well in 100 pt of the stripped medium. The cells were allowed to attach and stabilize overnight, after which 100 µl, of fresh medium with or without $10^{-9}$ M of estradiol (E2) were added to each well. After the cells were incubated with E2 overnight, 100 µl of stripped medium containing $10^{-9}$ M of E2 with various concentrations of EDX (0, 1, 5, 10, 50, 100, 500 and 1000 nM) with 1% DMSO, EDX-loaded micelles with equivalent drug concentrations, or empty micelles with equivalent micelle concentrations, were added to each well (n=6). An ER-negative cell line, MDA-MB-231, was also interrogated using these micelles. The cells were maintained in L-15 cell culture media supplemented with 10% (v/v) charcoal-stripped fetal bove serum (Invitrogen), and 1% (v/v) penicillin/streptomycin under the same inclubation and treatment conditions.

The treatment was repeated every other day until the fifth day. The cell proliferation was assessed using a CellTiter 96 AQueous One Solution (MTS) Reagent (Promega Corp., Madison, Wis.) according to the manufacturer's protocol. Briefly, the culture media were removed and the cells were washed with pre-warmed PBS and fresh basal medium; then, 100 [IL of fresh complete medium, along with 20 µl, of the MTS reagent, were added to each well. The plate was incubated for 2 h at 37° C. in a humidified, 5% $CO_2$ atmosphere. The UV absorbance was measured at 490 nm using a Labsystems Multiskan Plus microplate reader (Labsystems, Finland). Mean cell proliferation was determined relative to negative controls (cells treated with $10^{-9}$M of E2 without drug).

Skin Preparation and Experimental Conditions for Franz Diffusion Experiments

Full thickness mouse skin was collected from the dorsal side of the 6-8 weeks old SKH1 hairless mice[104] (Charles River Laboratory, Boston, Mass.). Subcutaneous fat and blood vessels were carefully removed using cotton swabs. Undamaged skin was cut into 1.2×1.2 $cm^2$ squares, rinsed with normal saline, and sandwiched between the donor and receiver chambers of the Franz diffusion cells with the SC side facing upward. The receiver chambers were filled with fresh normal saline containing 30% ethanol. After equilibration of the skin at 37° C. for 30 min, 100 µl of each treatment (4 mg/mL of micelle or liposome in water containing same amount of EDX, or corresponding amount of free EDX in 60% ethanol-40% $ddH_2O$) or vehicle (double distilled water ($ddH_2O$) with 60% ethanol) were applied to the donor chambers. The chambers were covered with Parafilm™ to avoid evaporation. The first sampling (t=0) was done by withdrawing 250 µl of receiver solution from each sampling port and replacing with 250 µl of fresh receiver solution. Samplings were performed at designated time points up to 24 h. All solutions were kept at 4° C. in darkness before analysis.

The acquisition of anonymous human skin samples from the operating room was approved by the Institutional Review Board of Northwestern University. The split-thickness skin (STS) samples were prepared as described in a previous study[65]. The STS samples were evenly spread on a supporting pad to scavenge moisture, sealed in a plastic bag, and snap-frozen in liquid N2. They were stored in −80° C. until being used for the Franz cell diffusion experiment.

Preparation of EDX Formulations for Human Skin Experiments

For human skin permeation experiments, three formulations of EDX were prepared as follows: 1) PDC-COOH (EDX) powder dissolved in $ddH_2O$ to make the stock solution (4 mg of EDX-containing micelle/mL), which contains 25.18 µg of free EDX/mg micelle; 2) EDX alone; and 3) EDX plus oleic acid (OA): the same amount of free EDX was prepared in the 60% (v/v) ethanol-phosphate buffer (PB, 2 mM $KH_2PO4$ and 4 mM $Na_2HPO_4$, pH 7.0) as described previously[65]. 0.5% (v/v) oleic acid (OA) was added to 60% (v/v) ethanol-PB for EDX plus OA formulation.

Permeation of EDX Using Franz Diffusion Cells

STS samples from two subjects were used for this study. The thickness of the STS samples was 389±29 microns (mean±SD). All other procedures for the diffusion experiment using human STS samples were the same as described in the mouse skin experiment.

Skin Processing and Experimental Conditions for CLSM Imaging

SKH-1 hairless mouse skin was exposed to the Cou6-loaded micelles with different surfaces for 24 h in the Franz cell setup. The skin area that was exposed to the treatment was carefully collected, rinsed twice with ddH$_2$O for 10 min and embedded into cryomolds (Tissue-Tek®, Sakura Finetek USA, Inc., Torrance, Calif.). Skin was cryosectioned into 80 um-thick slices and placed on anti-frost glass slides. The slides were then fixed by 10% neutral buffered formalin for 10 min at RT and rinsed with ddH$_2$O. The skin slides were mounted with antiphotobleaching mounting media with DAPI (Vector Laboratory Inc., Burlingame, Calif.) and covered with glass cover slips. The slides were visualized using a Zeiss LSM 510 Meta CLSM (Carl Zeiss, Germany). The 488 nm line of a 30 mW tunable argon laser was used for the excitation of Cou6, and a 25 mW diode UV 405 nm laser for DAPI. Emission was filtered at 505-530 nm and 420 nm for Cou6 and DAPI, respectively.

Measurements of Skin Permeation and Retention

Twenty-four hours after the Franz cell experiment, donor solutions were collected and kept at 4° C. in darkness before analysis. Skin was also collected and thoroughly cleaned. The effective exposure area was excised and homogenized in a 1.5 mL centrifuge tube. DMSO was used as an extracting solvent. After 12 h of extraction, the tubes were centrifuged at 10,000 rpm for 10 min, and the supernatant was collected for analysis.

RP-HPLC was used to detect endoxifen from the receiver solutions, skin extracts, and donor solutions. All samples were filtered through 0.20 um syringe filters and pre-treated by a CHIPhEarser as described above. All the HPLC conditions were the same as described earlier.

After the two-dye micelle experiment, the fluorescence intensity in the donor and receiver solutions, as well as skin extracts were detected using a SoftMax Pro spectrofluorometer (Spectra MAX, Molecular Devices Inc., Sunnyvale, Calif.). For the detection of Cou6, the excitation wavelength was 444 nm and the emission wavelength was 510 nm. For the detection of RHO from the dendron micelle, the excitation wavelength was set at 555 nm, and the emission wavelength was 590 nm.

Statistical Analysis

Data processing was performed using Origin 8.6. Statistical analysis was performed using SPSS 11.5 based on a one-way ANOVA and data were considered significant at p<0.05.

Results

Characterization of Micelles and Liposome

The dialysis method was used to prepare surface modified, EDX-loaded dendron micelles, and a thin film hydration-extrusion method was used to prepare liposomes. The particle size, ς-potential, and drug loading are listed in Table 5.

TABLE 5

Characterizations of EDX-loaded micelles and liposome

| Materials | Size (nm)[a] | ζ-Potential (mV) | Drug Loading[b] | Loading %[c] | Encapsulation Efficiency %[d] |
|---|---|---|---|---|---|
| EDX/M-NH$_2$ | 48.7 ± 7.1 | 42.9 ± 1.6 | 3.0 ± 1.3 | 0.3 ± 0.1% | 2.0 ± 0.9% |
| EDX/M-Ac | 37.4 ± 6.2 | −2.7 ± 1.4 | 5.7 ± 0.2 | 0.6 ± 0.0% | 3.8 ± 0.1% |
| EDX/M-COOH | 48.4 ± 6.1 | −23.2 ± 3.5 | 29.7 ± 2.0 | 3.0 ± 0.2% | 19.8 ± 1.4% |
| EDX/Liposome | 100.5 ± 20.9 | 28.6 ± 0.3 | 0.4 ± 0.0 | 0.1 ± 0.1% | 0.0 ± 0.0% |
| Cou-6/M-RHO-NH$_2$ | 75.2 ± 8.3 | | 1.2 ± 0.1 | 0.1 ± 0.0% | 6.1 ± 0.7% |
| Cou-6/M-RHO-Ac | 24.0 ± 4.2 | | 1.6 ± 0.2 | 0.1 ± 0.0% | 8.2 ± 1.1% |
| Cou-6/M-RHO-COOH | 24.5 ± 3.3 | | 1.4 ± 0.1 | 0.1 ± 0.0% | 6.2 ± 0.7% |

Figure 23:
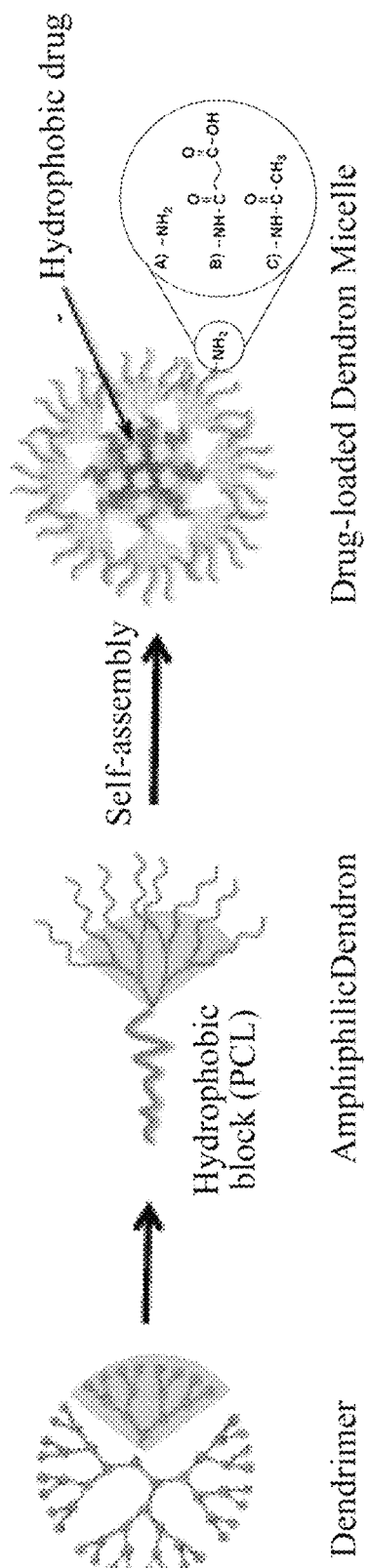
FIG. 23 shows TEM images of EDX-loaded, surface modified dendron micelles. (Scale bar: 100 nm)
Figure 23:
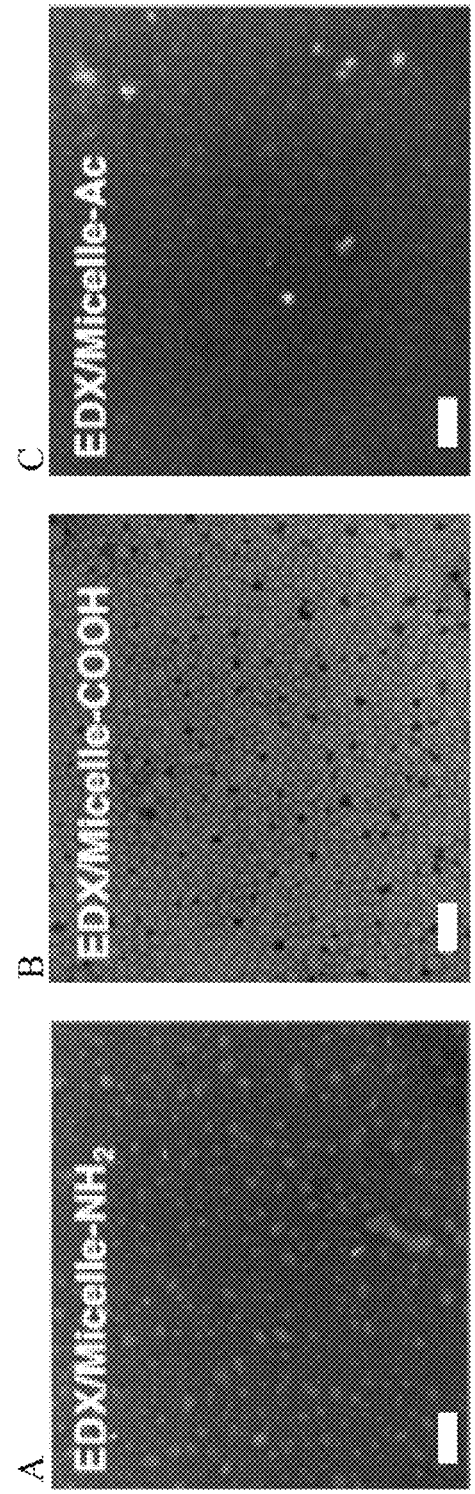

[a]Measured using dynamic light scattering.
[b]Measured using RP-HPLC, expressed as "μg of drug/mg of DMs"
[c]Loading % = (Total amount of EDX encapsulated in μg/Total weight of nanoparticles in μg) × 100%
[d]Encapsulation Efficiency % = (Amount of drug encapsulated in μg/Amount of drug added for encapsulation in μg) × 100%
All data presented are mean ± SD The encapsulation of EDX into dendron micelles yielded number-weighted average diameters between 37.4 and 48.7 nm with a narrow distribution, which were in agreement with TEM images (FIG. 23). In contrast, EDX-loaded liposomes had an average size of 100.5 nm. Surface modification of PDCs followed by self-assembly resulted in three different types of dendron micelles (M-NH$_2$, M-COOH, and M-Ac). Zeta-potential measurements revealed that the amine-terminated M-NH$_2$ and liposomes were positively charged (42.9±1.6 mV and 28.6±0.3 mV, respectively). After surface modification of PDC-NH$_2$, the surface charge of the acetylated micelle (M-Ac) was decreased to nearly neutral (−2.7±1.4 mV), and the surface charge of M-COOH was reversed to a negative value (23.2+3.5 mV). The drug loading of liposomes and dendron micelles was measured using RP-HPLC. Liposomes encapsulated the least amount of EDX, possibly because these nanoparticles were more suitable for encapsulating hydrophilic molecules due to their aqueous core and relatively less hydrophobic regions than micelles (0.05%)[84]. M-NH$_2$ and M-Ac had moderate drug loading (0.30±0.13% and 0.57+0.02%, respectively), and M-COOH encapsulated the highest amount of EDX (2.97+0.20%). The Cou6-loaded dendron micelles had similar drug loading, but the size of Cou6-loaded M-NH$_2$ was larger than M-Ac and M-COOH.

In Vitro Drug Release Study

Figure 24:
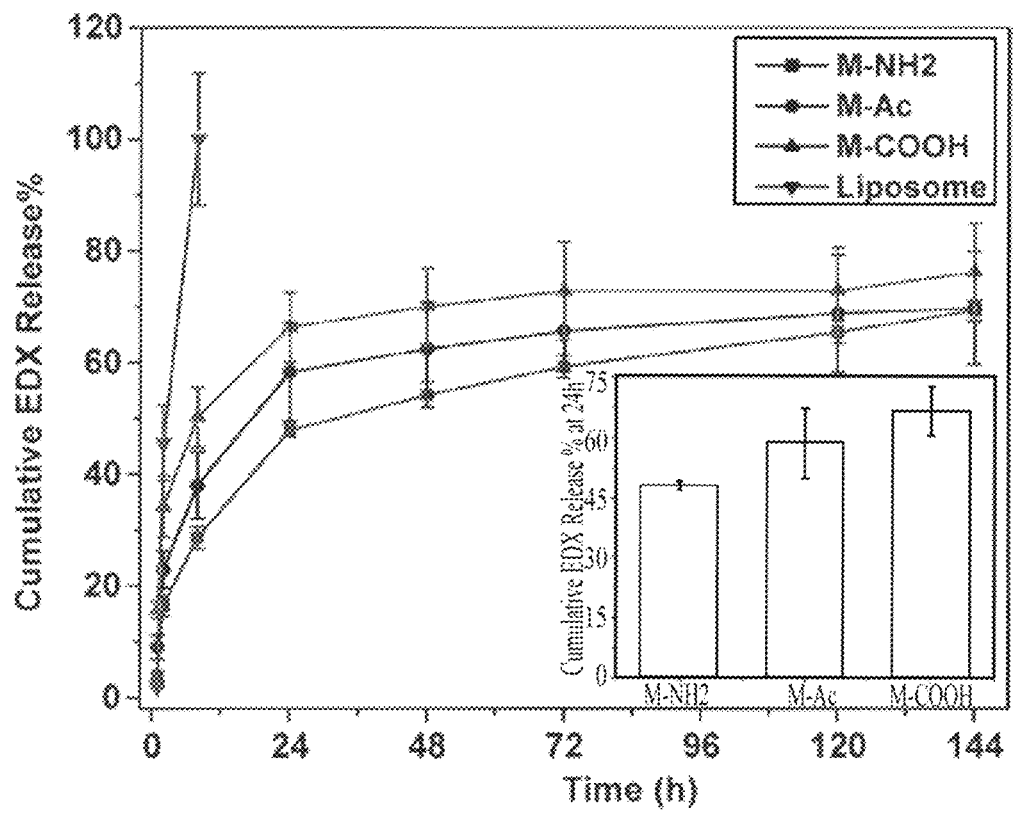
FIG. 24 shows the in vitro EDX release from liposomes and surface modified micelles. EDX-loaded nanoparticles demonstrated distinct drug release profiles over 6 days (144 h). The order of extended release was M-$NH_2$>M-Ac>M-COOH>Liposome. Inset: cumulative EDX release at 24 h. Note that the liposomes had already reached 100% release as early as 8 h. Error bars: Standard error (SE).

Release of EDX from cationic liposomes and dendron micelles was measured using RP-HPLC (FIG. 24). Liposomes completely released the encapsulated EDX after 8 h, while M-NH$_2$ released only 57.05% of EDX after the same time period. The release profile of surface-modified dendron micelles was charge dependent. For all dendron micelles, EDX was released in a controlled manner with a biphasic release profile (M-NH$_2$<M-Ac<M-COOH). M-COOH with the highest drug loading exhibited fastest drug release, whereas M-NH$_2$ had the lowest drug loading and slowest release rate.

In Vitro Anti-Proliferation Assay Against Breast Cancer Cells

Figure 25:
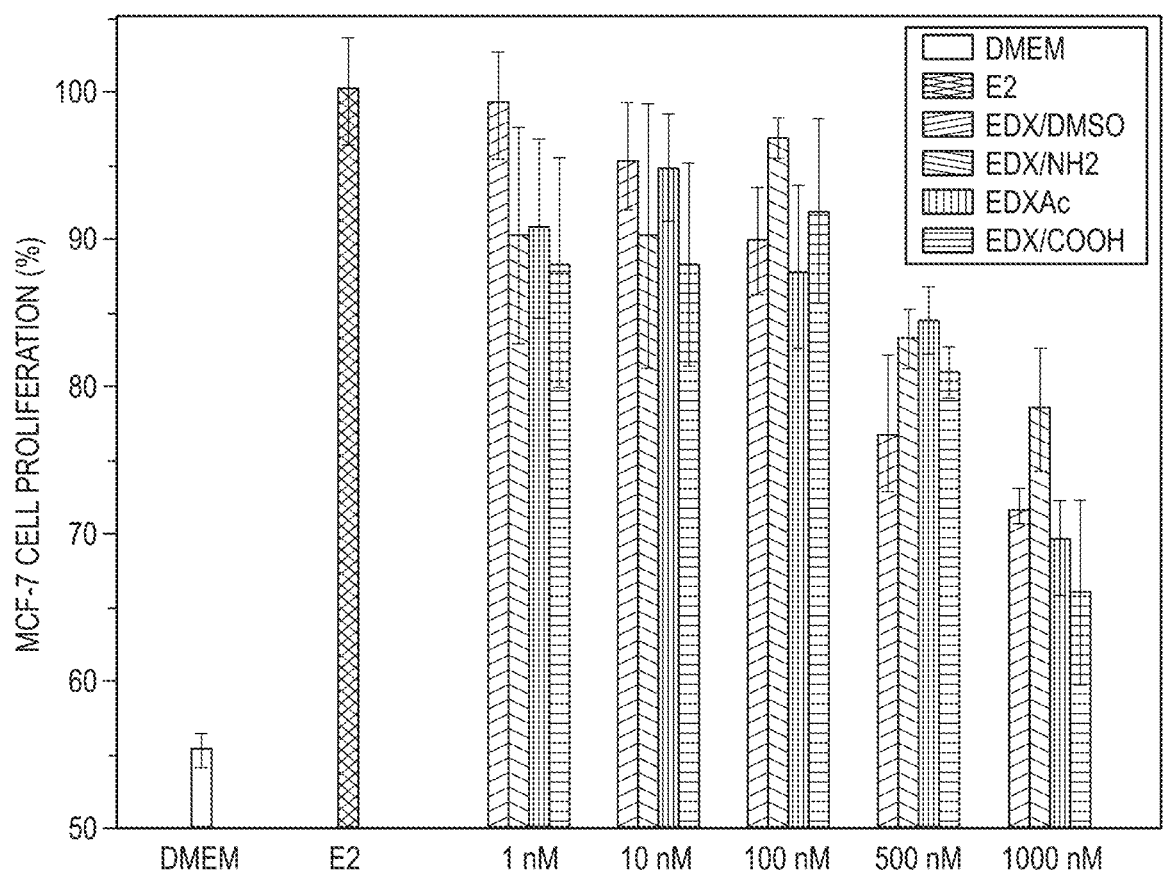
FIG. 25 shows the results of experiments testing the in vitro cytotoxicity of EDX-loaded micelles and free EDX. MCF-7 cells were treated with free EDX or EDX-encapsulated micelles. The anti-proliferative effect of EDX encapsulated into dendron micelles is comparable to that of free EDX, whereas empty micelles did not exhibit significant cytotoxicity. DMEM, control group without any treatment; E2, f3-estradiol ($10^{-9}$ M); EDX/DMSO, free EDX in DMEM with 1% of DMSO; EDX/$NH_2$, EDX/Ac, and EDX/COOH, EDX encapsulated in dendron micelles with different surface functionalities. All the groups were treated with same amount of E2 except for the DMEM control group.
Figure 26:
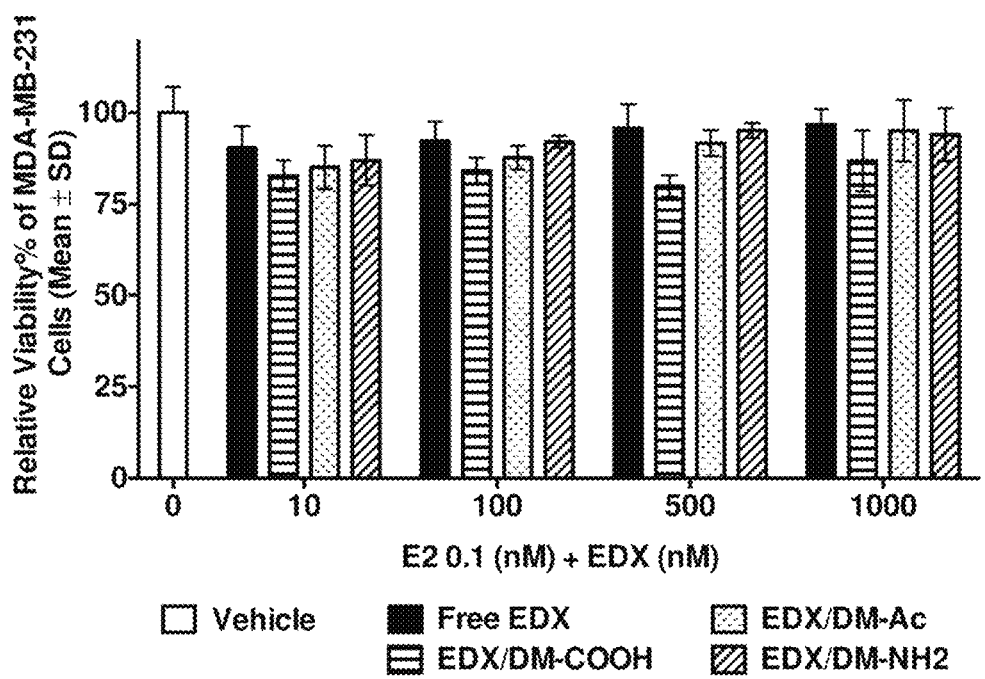
FIG. 26 shows the in vitro anti-proliferative effect of EDX in its free from and in surface-modified DMs evaluated using MTS assay. Estrogen receptor-negative (ER-) MDA-MB-231 breast cancer cells were treated with EDX or EDX-loaded DMs with comparable drug concentrations. Neither free EDX nor EDX-loaded DMs exhibited significant anti-proliferative effect against MDA-MB-231 cells, indicating the EDX effect against cell proliferation is ER-dependent. EDX/DM-COOH, EDX/DM-Ac, and DM-$NH_2$ are EDX-loaded DMs with different surface functional groups. All groups were treated with 0.1 nM of E2, and the cell viability was relative to the cells that were not treated with EDX formulations. Error bars: standard deviation, SD, n=3.

The anti-proliferative effect of EDX was tested using ER-positive MCF-7 and ER-negative MDA-MB-231 breast cancer cells. EDX exhibited a concentration-dependent growth inhibition against MCF-7 cells (FIG. 25). Aqueous solutions of dendron micelle-encapsulated EDX used at the same concentration as free EDX demonstrated comparable efficacy. The empty micelles, on the other hand, did not elicit cytotoxic effect to MCF-7 cells at concentrations up to 1000 nM (FIG. 26). Meanwhile, under similar concentrations, neither free EDX nor EDX-loaded micelles had significant cytotoxicity against MDA-MB-231 cells (FIG. 26).

Mouse Skin Permeation Studies Comparing M-NH$_2$, Liposomes, and Ethanol

Figure 27A:
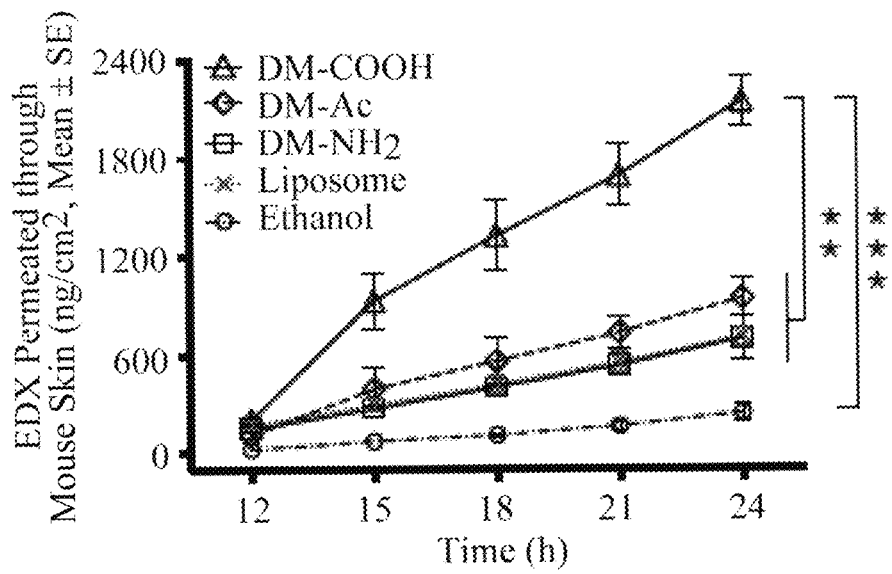
FIGS. 27A-27B show skin permeation of EDX delivered by various vehicles across mouse and human skin. A) Mouse skin permeation of EDX over 24 h. B) Human skin permeation of EDX over 24 h. DM-COOH induces permeation of the highest amount of EDX across both the mouse and human skin layers. OA, oleic acid. Eerror bars: standard error, SE, n=3-6. p<0.005; *p<0.001.
Figure 27B:
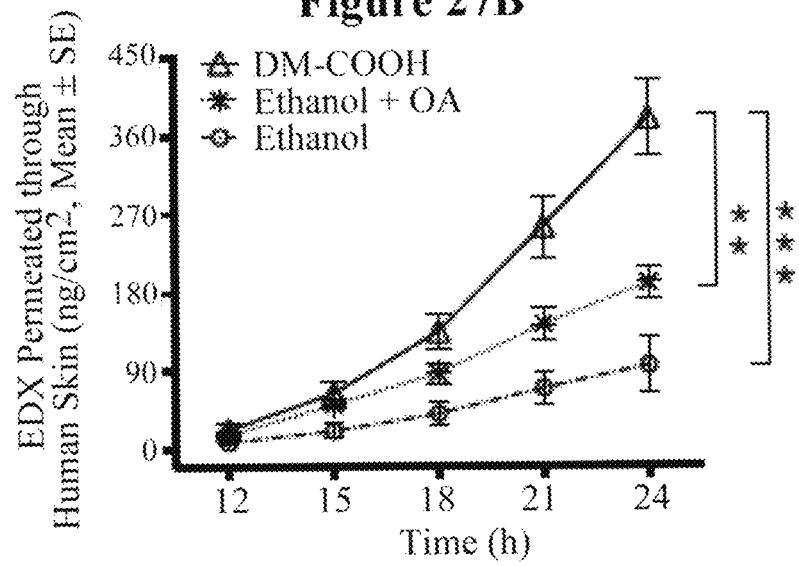

To compare the ability of different nanoparticles to deliver EDX through hairless mouse skin, Franz diffusion cell experiments were carried out using dendron micelles and liposomes. EDX (37.44 μg) content was normalized across groups based on drug loading % before application to freshly excised mouse skin. Due to the increased solubility of EDX in micellar and liposomal formulations, ddH$_2$O was used as a vehicle. M-NH$_2$ and liposomes delivered similar amount of EDX with comparable flux (FIG. 27). After 12 h, a small amount of EDX was detected in the receiver solutions of the dendron micelles (0.33±0.04 μg, 0.07 pg/cm$^2$/h) and liposomes (0.34±0.02 μg, 0.07 pg/cm$^2$/h), which was slightly more than the ethanol formulation (0.28±0.01 μg, 0.06 μg/cm$^2$/h). The average cumulative amount of permeated EDX after 24 h was 0.71±0.27 μg (0.08 μg/cm$^2$/h) and 0.78±0.21 μg (0.08 μg/cm$^2$/h) from the dendron micelles and liposomes, respectively, which was significantly higher than the ethanol formulation (0.38±0.05 lig (0.04 μg/cm$^2$/h)). From 24 h to 36 h, the delivered EDX was 1.33±0.57 pg (0.10 μg/cm$^2$/h) from the micelles and 1.26 1 0.26 p,g (0.09 pg/cm$^2$/h) from the liposomes. However, only 0.49±0.05 μg (0.04 μg/cm$^2$/h) of EDX was delivered by the ethanol. After 36 h, the permeation curves had drastic slope changes, which indicated that the skin was hydrated and the data was no longer valid (FIG. 28). Hence, we took 24 h as the final sampling time point for all of the following Franz diffusion experiments to avoid skin hydration.

Mouse Skin Permeation Studies on Surface Modified Micelles

Figure 28A:
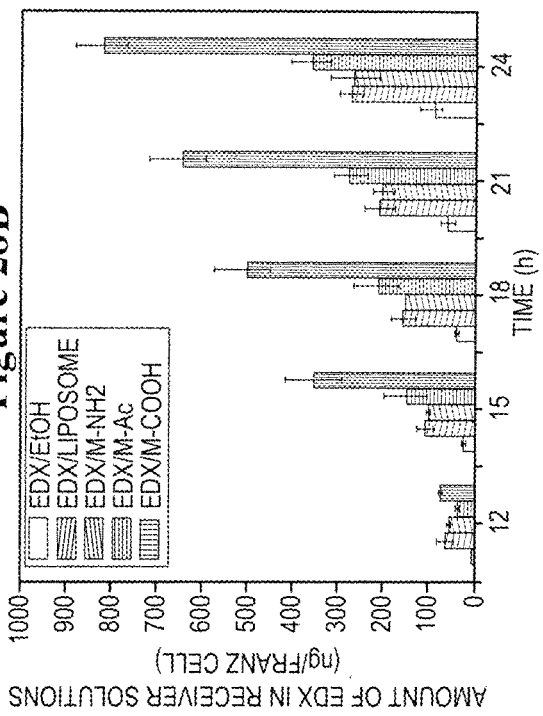
FIGS. 28A-28D show skin permeation of EDX delivered by ethanol, liposomes, and surface modified dendron micelles. Different drug loading leads to diverse drug delivery efficiencies over 24 h (error bars: standard error, SE, n=3-6). A) Percent permeation of EDX delivered by different vehicles. Note that liposomes have the highest permeation % and all the nanoparticles are significantly more efficient than ethanol (EtOH). Micelles have similar EDX delivery efficiencies, regardless of their surface charges. B) The permeated amount of EDX in receiver solutions at different times. C) Skin deposition of EDX at the end (24 h) of the Franz diffusion experiment. D) Total permeation of EDX (skin+receiver) at 24 h. Note that EDX-encapsulated M-COOH could encapsulate and deliver the highest amount of EDX through the skin layers, while liposomes could encapsulate and deliver much lower amount of EDX compared to micelles. Ethanol (70% in ddH$_2$O) delivered the least amount of EDX as compared to other vehicles that are dispersed in pure ddH$_2$O. *p<0.05.

To investigate the effect of surface charge on skin permeation efficiency, surface modifications dendron micelles were prepared with three different charge moieties on the end-groups of the PEG chains. Table 6 summarizes the calculated skin permeation parameters using mouse skin. After 24 h, all dendron micelles demonstrated similar skin permeation % of EDX (FIG. 28A).

Figure 28B:
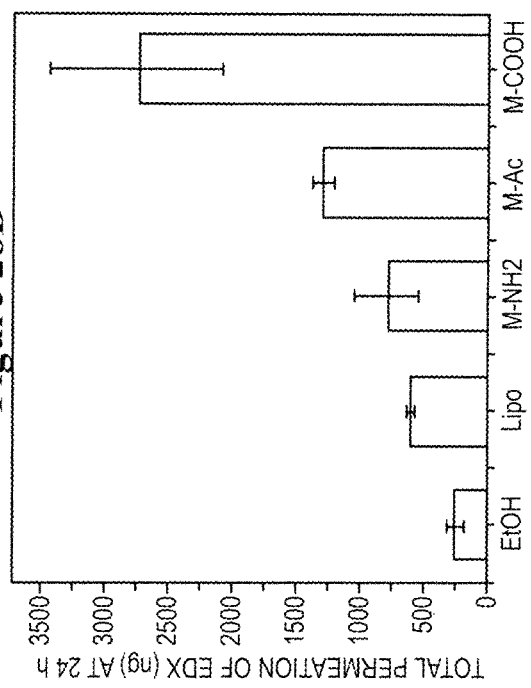
Figure 28C:
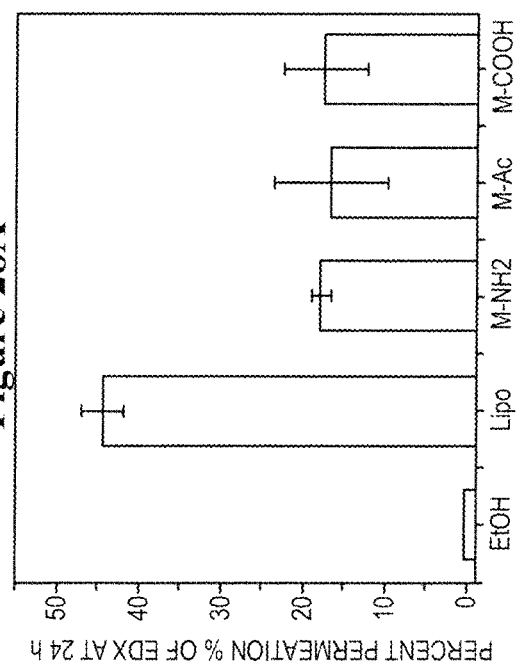
Figure 28D:
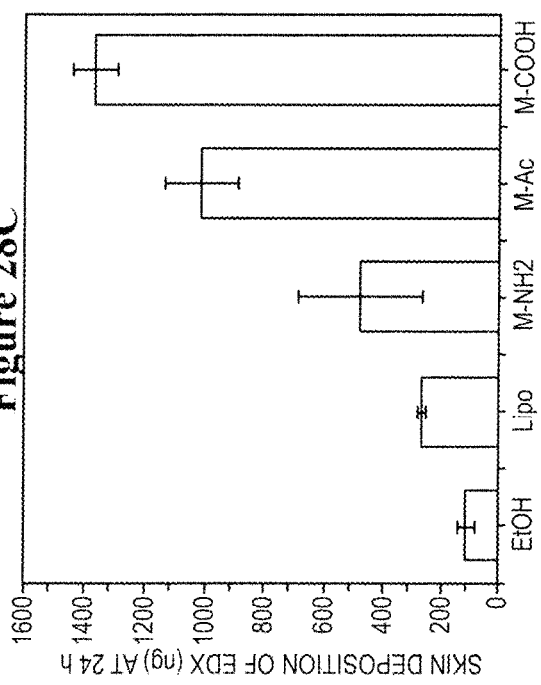

However, due to different drug loading percentages, the total amount of EDX permeated across the skin layers had a different pattern (FIG. 28B-D) compared to permeation %. A time course study revealed that EDX release depended largely on drug loading (FIG. 28B). M-COOH had the highest drug loading (31.70 i_tg EDX/mg M-COOH), and it allowed the greatest skin permeation of EDX within 24 h (2142.17±151.76 ng/cm$^2$ with a steady state flux of 154.65 ng/cm$^2$/h). On the other hand, M-NH$_2$ and M-Ac had much lower drug loadings (4.29 lig EDX/mg M-NH$_2$ and 5.54 [tg EDX/mg M-Ac, respectively), thus delivering smaller quantities of EDX through the skin (691.88±135.27 ng/cm$^2$ and 938.16±113.83 ng/cm$^2$ for M-NH$_2$ and M-Ac, respectively). The liposomes also delivered a small amount of EDX (706.12±50.89 ng/cm$^2$), similar to M-NH$_2$. A much lower level of EDX permeation was observed when using ethanol (236.75±56.81 ng/cm$^2$) (FIG. 28D and Table 6). Overall, the transdermal EDX delivery efficiency followed the order of M-COOH>M-Ac>M-NH$_2$>liposome>Ethanol.

Figure 29A:
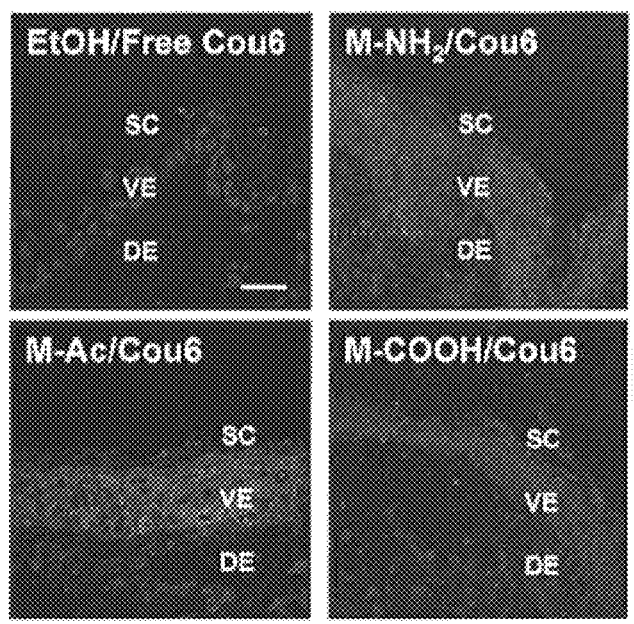
FIGS. 29A-29B show skin deposition of Cou6-encapsulated, RHO-labeled dendron micelles. A) CLSM images of the SKH1 hairless mouse skin cross-sections after treatment for 12 h with I) Free Cou6 in ethanol (EtOH/Free Cou6), or Cou6-encapsulated, RHO-labeled II) M-Ac (M-Ac/Cou6), III) M-COOH (M-COOH/Cou6), IV) M-NH$_2$ (M-NH$_2$/Cou). Images are merged to show localization of Cou6 (green) and nuclei stained by DAPI (blue). Note that the RHO-labeled dendron micelles are not detectable in the skin layers. Scale bar: 20 pm. SC, stratum corneum; VE, viable epidermis; DE, dermal layer. *p<0.05. B) Skin deposition of Cou6 delivered by dendron micelles measured using a spectrophotometer after skin extraction with DMSO. Note that ethanol delivered significantly lower amount of Cou6 through the skin layers. Micelles exhibited similar abilities to deliver the encapsulated Cou6 regardless of their surface functionalities.

Skin Permeation Observation of Two-Dye Dendron Micelles Using Confocal Laser Scanning Microscopy CLSM images shown in FIG. 29A exhibits Cou6 delivered by the Cou6-encapsulated, RHO-labeled two-dye dendron micelles. After 24 h of Franz cell experiment, the skin samples treated with these micelles were harvested, cryo-sectioned and stained with DAPI. As seen from the green signal in the images, micelles deposited high levels of the encapsulated Cou6 to reach both the epidermal and dermal layers. By way of contrast, free Cou6 could not diffuse efficiently into the skin layers even with the presence of ethanol as a permeation enhancer. RHO that were labeled on the dendron micelles, on the other hand, did not show their presence in the skin layers, indicating the micelles do not penetrate into the skin layers.

Skin Retention of Cou6 Delivered by Two-Dye Dendron Micelles

Figure 29B:
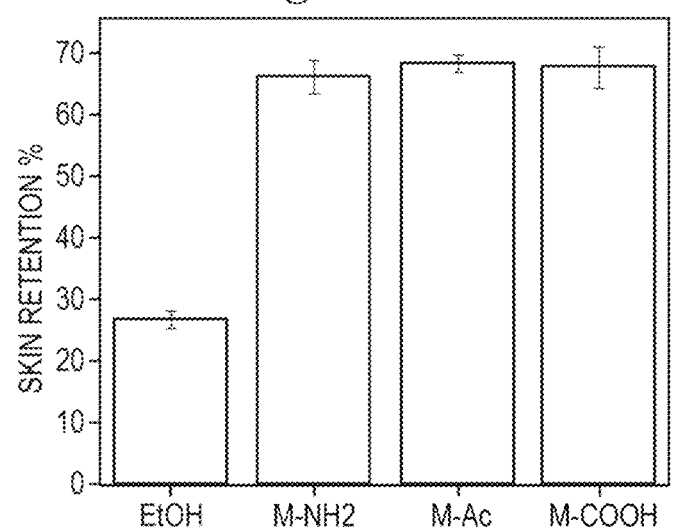

After the Franz cell experiment, skin was collected, and the skin extracts were analyzed using a spectrofluorometer. FIG. 29B shows that all three types of micelles delivered significantly higher amounts of Cou6 through the skin (M-COOH 67.14±5.78%, M-Ac 68.11±2.14%, and M-NH$_2$ 65.98±4.13%) than free Cou6 delivered by ethanol (26.48±2.51%). The drug loading was similar among these 3 micelles, and they all exhibited the similar ability to deposit large amounts of Cou6 into the skin. However, there was no significant difference among surface modified micelles in their abilities for delivering the encapsulated Cou6, and RHO-labeled micelles were not detectable from the skin extracts.

TABLE 6

Skin permeation parameters of EDX delivered through mouse and human skin.

| Skin type | Vehicles | Flux (J) (ng/cm$^2$/h) | Lag time (h) | Permeability Coefficient ($K_p$) (cm/h) | Diffusion Coefficient (D) (cm$^2$/h) | Enhancement Ratio (ER) |
|---|---|---|---|---|---|---|
| Mouse | EtOH | 17.1 | 11.0 | 4.6 × 10$^{-4}$ | 6.1 × 10$^{-6}$ | 1.0 |
|  | Liposome | 44.1 | 8.3 | 46.7 × 10$^{-3}$ | 8.0 × 10$^{-6}$ | 2.6 |
|  | DM-NH$_2$ | 45.0 | 9.0 | 79.5 × 10$^{-4}$ | 7.4 × 10$^{-6}$ | 2.6 |
|  | DM-Ac | 66.5 | 9.8 | 91.7 × 10$^{-4}$ | 6.8 × 10$^{-6}$ | 3.9 |
|  | DM-COOH | 154.7 | 9.9 | 37.9 × 10$^{-4}$ | 6.8 × 10$^{-6}$ | 9.0 |
| Human | EtOH | 7.5 | 12.3 | 6.7 × 10$^{-4}$ | 2.0 × 10$^{-5}$ | 1.0 |
|  | EtOH w/OA | 14.7 | 11.7 | 13.3 × 10$^{-4}$ | 2.2 × 10$^{-5}$ | 2.0 |
|  | DM-COOH | 30.2 | 11.4 | 27.3 × 10$^{-4}$ | 2.2 × 10$^{-5}$ | 4.0 |

Human Skin Permeation Studies

Figure 30A:
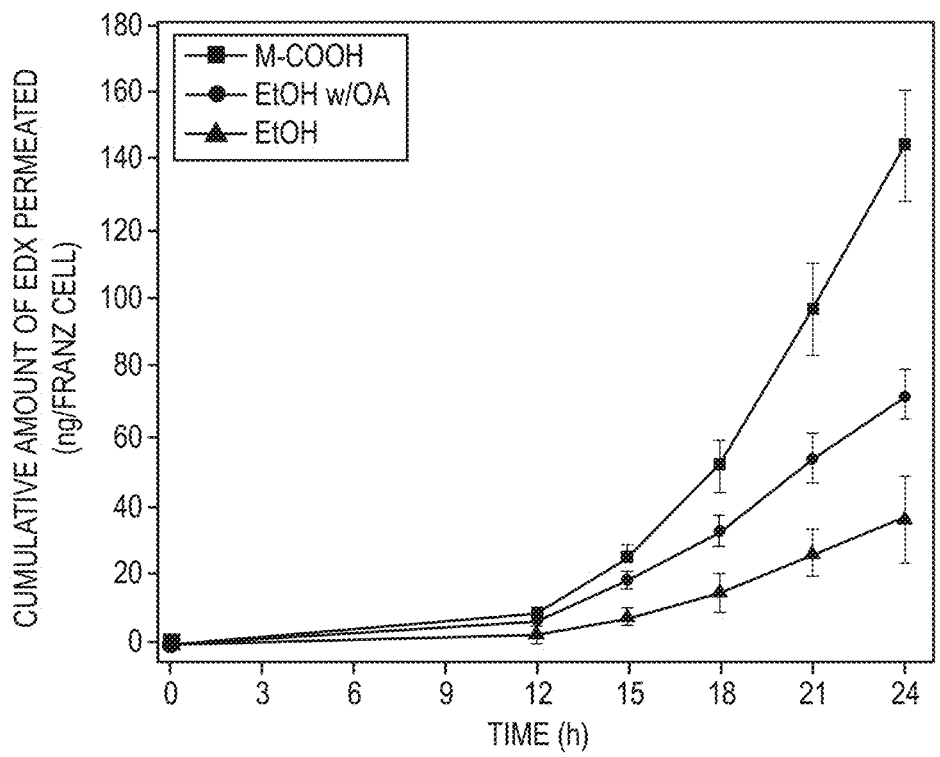
FIGS. 30A-30B shows human skin permeation of EDX delivered by ethanol, ethanol w/ 1% OA, and M-COOH. A) The cumulative amount of EDX permeated into the receiver solutions at different time. B) Percent permeation of EDX delivered by different vehicles. M-COOH exhibited a 4-fold higher Permeation % than ethanol, and a 2-fold higher Permeation % than ethanol-OA combination. (error bars: SE, n=4).
Figure 30B:
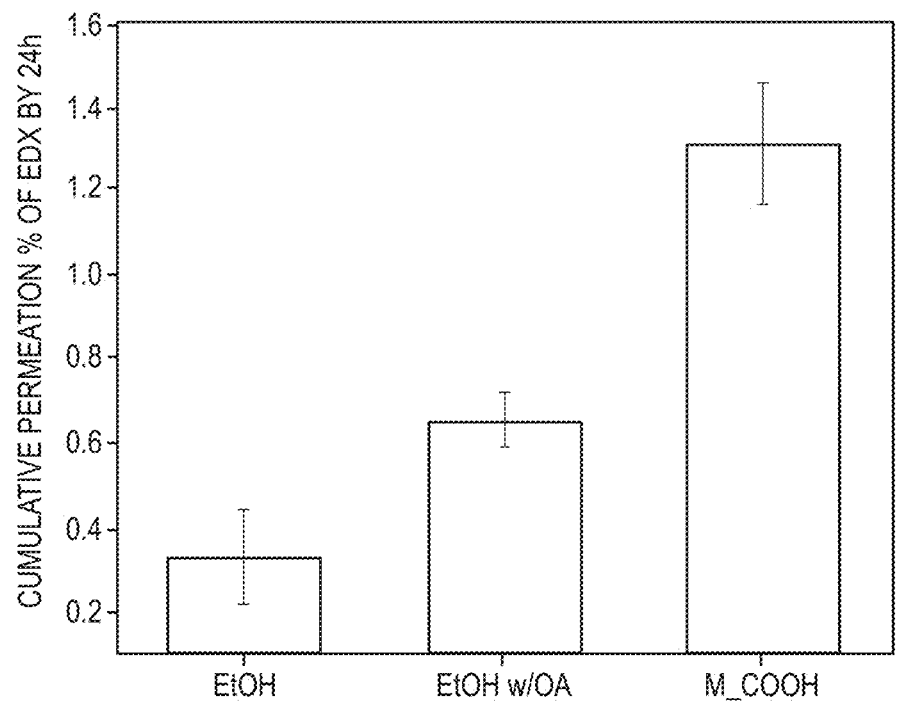

To further investigate the skin permeation of EDX, we compared M-COOH with CPEs in terms of their drug delivery efficiencies across split-thickness human skin. As shown in Table 6 and FIG. 30, compared to 60% ethanol that facilitated an EDX flux at 7.5 ng/cm$^2$/h, M-COOH facilitated a more than four-fold higher flux of EDX (30.2 ng/cm$^2$/h) through the human skin. M-COOH was also compared with the ethanol-OA system that was developed earlier (flux: 14.7 ng/cm$^2$/h) and a 2-fold higher flux was observed from the micelle delivery system. The permeation % of EDX also followed the order of M-COOH>ethanol-OA>ethanol, indicating M-COOH as an efficient transdermal drug delivery vehicle.

DISCUSSION

In this study, we used dendron-based micelles to achieve effective delivery of EDX through transdermal route. We first prepared three types of surface modified dendron micelles to evaluate their ability to act as solubilizers for the encapsulated EDX. The preparation of water-soluble formulations is critical for the preparation of many pharmaceutical and cosmetic formulations. CPE micelles composed of monomeric surfactants (such as SDS) and/or phospholipids have been used to solubilize mildly hydrophobic molecules, such as econazole and sulforhodamine B for transdermal delivery. Issues related to skin irritation have drawn much negative attention from the widespread use of SDS as a CPE. This has fostered the development of new materials for topical micelle formulations. In our study, PDCs were synthesized from the combination of a single hydrophobic core-forming block poly(E-caprolactone) (PCL) with multiple hydrophilic PEG chains mediated by a hydrophilic G3 polyester dendron (Pearson, 2012 #304). Encapsulation of EDX into dendron micelles significantly increased the water solubility of the drug and provided the potential to deliver this drug without the use of organic solvents. The high log P value of EDX demonstrates its high hydrophobicity and poor water solubility. By using an aqueous formulation (ddH$_2$O) of EDX-encapsulated dendron micelles, the need of CPEs in the formulation was eliminated, effectively increasing the stability of EDX during storage and administration by prohibiting aggregation and inconsistency of concentrations. The prepared micelle formulations were fully dispersible in ddH$_2$O, and no precipitation of the drug from the micelles was observed throughout any experiments. From these results, the use of dendron micelles enhanced the solubility and stability of EDX significantly, thus overcoming one of the barriers to transdermal drug delivery.

The drug release profile of EDX-encapsulated dendron micelles was then evaluated using Franz diffusion cells. To facilitate solubilization of EDX, the releasing medium contained 30% ethanol. All micelles were observed to have a controlled, biphasic drug release profile (FIG. 24). The initial fast release of EDX after 8 h could be attributed to the possibility that EDX was adsorbed to the surface of the dendron micelle during micelle preparation process[28]. EDX-encapsulated in the hydrophobic PCL core was released slowly from the micelles over 6 days (144 h). The faster release of EDX from M-COOH could also contribute to the higher skin permeations. Liposomes, on the other hand, released all the encapsulated EDX at after 8 h, indicating that the liposome was unable to stably encapsulate EDX.

After we obtained EDX-encapsulated micelles, we evaluated whether the drug efficacy was maintained. As expected, we found that empty dendron micelles did not cause significant cytotoxicity towards both ER-positive and ER-negative breast cancer cell lines (FIGS. 25 and S3B), while EDX-encapsulated micelles had similar anti-proliferative effects against ER-positive MCF-7 cells. This indicated that the dendron micelles could maintain the efficacy of EDX and would not cause cytotoxicity when used alone. This was in agreement with the results obtained using the KB cell line as reported previously[86].

Next, we tested whether the dendron micelles can be used as an efficient transdermal delivery vehicle for EDX. We first compared our micelle systems with ethanol and cationic liposomes that have been commonly used for transdermal delivery, in terms of skin permeation and retention using both mouse and human skin. The size of the micelles (<50 nm) was in nanoscale and was only half the size of the liposomes (~100 nm). The smaller size of micelles resulted in larger surface area, which would facilitate better interaction with the skin surface[70]. Using a two-dye micelle system, we found that the dendron micelles did not enter into the skin; rather they immediately released and deposited the encapsulated drug into the skin layers with high efficiency. All micelles delivered more EDX through the skin layers than ethanol (FIG. 28), which indicated that the interaction of the skin with micelles was stronger than with ethanol; in other words, the amphiphilic micelle was a better nanocarrier/permeation enhancer for EDX.

In this study, we have prepared a cationic liposome and used it as control vehicle for effective transdermal drug delivery. Results showed that dendron micelles could encapsulate and deliver more EDX into the skin layers. According to the study using monomeric micelles for transdermal drug delivery[79,81,98,99], the mechanism behind this phenomenon was explained as skin barrier perturbation[100], but not skin irritation[101]. As reported by Ghosh et al., the size of the micelle could directly dictate how easily it permeated the skin, thus determining whether it will cause skin irritations[101]. They claimed that the skin penetration of micelles was mostly through aqueous porous pathway, and the average size of skin aqueous pores is 2.90±0.50 nm. The measured radius of SDS micelles was 1.95±0.10 nm, thus they could cause skin irritation; but the larger micelles (sodium cocoyl isethionate (SCI) micelle with 3.35±0.10 nm radius) did not[101]. In our study, all of the prepared micelles were much larger than the SCI micelle; thus, they were not permeable to the skin, as confirmed by CLSM observations of the two-dye micelle system (FIG. 29A). However, according to our permeation results, these micelles effectively facilitated skin translocation of EDX despite the fact that the micelles were almost skin impermeable. From the CLSM images (FIG. 29A), the permeated dye was not refined to hair follicle regions, which indicated that micelles delivered the encapsulated hydrophobic molecules mainly through free-volume diffusion (through lipid bilayers) and lateral diffusion (along lipid bilayers)[102]. However, the process of how the micelles interacted with the skin to facilitate higher skin permeation of the small molecules requires further study. Moreover, the CLSM images also demonstrated that the dendron micelles caused greater skin permeation of Cou6 than ethanol (FIG. 29), which confirmed the superiority of dendron micelles over ethanol for the delivery of hydrophobic molecules through the skin.

The different surface charge moieties on the micelles led to distinctly different drug loading efficiencies, especially when the encapsulated drug was also charged, and this directly affected the skin permeation efficiencies. For surface modified two-dye micelles, the dye loading was similar among the three, and the skin retention analysis revealed that surface-modified micelles deposited similar amount of Cou6 into the mouse skin. By comparing with the EDX-micelles, this indicated that the drug/dye loading could directly affect the skin permeation efficiency.

The skin permeation parameters of EDX were calculated and summarized in Table 6. The rate of EDX permeation was proportional to drug loading; in this case, M-COOH>>M-Ac>M-NH2 (FIG. 28A). The highest permeation coefficient was obtained by using liposomes, which confirmed that liposomes were effective transdermal drug delivery vehicles that could be used for positive control. However, due to their poor drug loading efficiencies for hydrophobic drugs (0.51 µg EDX/mg liposome), the amount of drug that could be delivered through the skin was very limited. In this aspect, liposomes demonstrated good skin delivery ability, but also proved to be better delivery vehicles for hydrophilic/amphiphilic molecules, where it could have higher drug loading within its hydrophilic core From these results, we concluded that M-COOH has the best drug loading and can deliver the highest amount of EDX through the skin within 24 h. Meanwhile, all of the micelles and liposomes prepared in this study exhibited much higher EDX delivery abilities compared to ethanol as a drug delivery vehicle. We have previously found that skin penetration behaviors of dendrimers could be modulated by surface charge modifications. By way of contrast, possibly due to the large size of micelles compared to dendrimers (~50 vs ~2 nm) and higher molecular weight to surface group ratio, surface modification did not directly impact the micelle-skin interactions, but affected drug loading efficiencies indirectly resulting in differences observed in drug delivery.

Using M-COOH, we further compared micelle's drug delivery efficiency through human skin. As compared to CPEs (ethanol and ethanol-OA combination), M-COOH excelled in delivering EDX with higher flux, shorter lag time, and better permeability coefficient. The obtained skin permeation parameters were lower than we obtained from previous study[83], which could be due to the lower amount of EDX applied to the skin. The results confirmed that the translation from rodent skin to human skin was fulfilled. This demonstrated the use of micelles as transdermal drug delivery vehicles for human.

Taken together, we have found that the dendron micelles can successfully encapsulate EDX and enhance its skin penetration. Among the three micelles with surface modifications tested, the M-COOH was the best in terms of EDX encapsulation and skin permeation. Through our investigation, the surface charge effect was not as prominent as PAMAM dendrimers; the higher skin permeation was attributed to the higher drug loading in the micelles. One of the advantages of dendron-based micelles is the ease of modulation in their structural designs. This study presents the potential of dendron micelles as transdermal delivery vectors and indicates that micelle structures can be tailored to the drug molecule to be delivered.

While the present invention has been described in terms of specific embodiments, it is understood that variations and modifications will occur to those skilled in the art. Accordingly, only such limitations as appear in the claims should be placed on the invention.

All documents cited in this application are hereby incorporated by reference in their entirety for their disclosure described.

DOCUMENTS CITED 1. (a) N. Wiradharma, Y. Zhang, S. Venkataraman, J. L. Hedrick and Y. Y. Yang, *Nano Today,* 2009, 4, 302; (b) A. Harada and K. Kataoka, *Prog. Polym. Sci.,* 2006, 31, 949.
2. (a) J. N. Israelachvili, D. J. Mitchell and B. W. Ninham, *J. Chem. Soc.* Farad. T. 2, 1976, 72, 1525; (b) G. M. Whitesides, J. P. Mathias and C. T. Seto, *Science,* 1991, 254, 1312.
3. B. M. Rosen, C. J. Wilson, D. A. Wilson, M. Peterca, M. R. Imam and V. Percec, *Chem. Rev.,* 2009, 109, 6275.
4. (a) S. Hong, P. R. Leroueil, I. J. Majoros, B. G. Orr, J. R. Baker, Jr. and M. M. Banaszak Holl, *Chem. Biol.,* 2007, 14, 107; (b) D. Q. McNerny, J. F. Kukowska-Latallo, D. G. Mullen, J. M. Wallace, A. M. Desai, R. Shukla, B. Huang, M. M. Banaszak Holl and J. R. Baker, Jr., *Bioconjug. Chem.,* 2009, 20, 1853; (c) I. Papp, C. Sieben, K. Ludwig, M. Roskamp, C. Bottcher, S. Schlecht, A. Herrmann and R. Haag, *Small,* 2010, 6, 2900; (d) M. A. Kostiainen, G. R. Szilvay, J. Lehtinen, D. K. Smith, M. B. Linder, A. Urtti and O. Ikkala, *ACS Nano,* 2007, 1, 103.
5. Olerlemans, C., Bult, W., et al. (2010) "Polymeric Micelles in Anticancer Therapy: Targeting, Imaging and Triggered Release." *Pharm Res* 27: 2569-2589.
6. Peer, D., J. M. Karp, et al. (2007). "Nanocarriers as an emerging platform for cancer therapy." *Nature Nanotechnology* 2(12): 751-760.
7. Sutton, D., N. Nasongkla, et al. (2007). "Functionalized micellar systems for cancer targeted drug delivery." *Pharmaceutical Research* 24(6): 1029-1046.
8. Israelachvili, J. N., D. J. Mitchell, et al. (1976). "Theory of Self-Assembly of Hydrocarbon Amphiphiles into Micelles and Bilayers." *Journal of the Chemical Society-Faraday Transactions Ii* 72: 1525-1568.
9. Kostiainen, M. A., J. G. Hardy, et al. (2005). "High-affinity multivalent DNA binding by using low-molecular-weight dendrons." *Angewandte Chemie-International Edition* 44(17): 2556-2559.
10. S. Hong, P. R. Leroueil, I. J. Majoros, B. G. Orr, J. R. Baker, Jr., M. M. Banaszak Holl, *Chem Biol* 2007, 14, 107-115.
11. B. M. Rosen, C. J. Wilson, D. A. Wilson, M. Peterea, M. R. Imam, V. Percec, *Chem Rev* 2009, 109, 6275-6540.
12. S. Hong, P. R. Leroueil, I. J. Majoros, B. G. Orr, J. R. Baker Jr. and M. M. Bananszak Holl, *Chemistry & Biology* 2007, 14, 107-115.
13. J. H. Myung, K. A. Gajjar, J. Saric, D. T. Eddington and S. Hong, *Angew. Chem. Int. Ed.* 2011, 50, 1-5.
14. Hong, S., Lemuel!, P. R., Majoros, 1. J., Orr, 13. G., Baker, J. R., Ir, and Banaszak Holl, M. M. (2007) The binding avidity of a nanoparticle-based multivalent targeted drug delivery platform, *Chem Biol* 14, 107-115.
15. Christensen, T., Gooden, D. M., Kung, J. B., and Toone, B. J. (2003) Additivity and the physical basis of multivalency effects: A thermodynamic investigation of the calcium BIDTA interaction, *Journal of The American Chemical Society* 125, 7357-7366.
16. Gestwieki, J. E., Cairo, C. W., Mann, D. A., Owen, R. M., and Kiessling, L. L. (2002) Selective immobilization of multivalent ligands for surface plasmon resonance and fluorescence microscopy, *Analytical Biochemistry* 305, 149-155.
17. Kitov, P. 1., and Bundle, D. R. (2003) On the nature of the multivalency effect: A thermodynamic model, *Journal Of the American Chemical Society* 125, 16271-16284.
18. Qiu, L. Y., and Bae, Y. H. (2006) Polymer architecture and drug delivery, *Pharm Res* 23, 1-30.

19. Hong, S., Bielinska, A. U., Mecke, A., Keszler, 13., Beals, J. L., Shi, X., Balogh, L., Orr, B. G., Baker, J. R., Jr., and Banaszak Holl, M. M. (2004) Interaction of poly(amidoamine) dendrimers with supported lipid bilayers and cells: hole formation and the relation to transport, *Bioconj. Chem* 15, 774-782.

20. Hong, S., Leroueil, P. R., Janus, E. K., Peters, J. L., Kober, M. M., Islam, M. T., Orr, 13. 0, Baker, J. R., Jr., and Banaszak Holl, M. M. (2006) Interaction of polycationic polymers with supported lipid bilayers and cells: nanoscale hole formation and enhanced membrane permeability, *Bioconjug Chem* 17, 728-734.

21. Leroueil, P. R., Hong, S., Mecke, A., Baker, J. R., Jr., Orr, B. G., and Banaszak Holl, M. M. (2007) Nanoparticle interaction with biological membranes: does nanotechnology present a Janus face?, *Ace Chem Res* 40, 335-342.

22. Parker, N., Turk, M. J., Westrick, B., Lewis, J. D., Low, P. S., and Leamon, C. P. (2005) Polate receptor expression in carcinomas and normal tissues determined by a quantitative radioligand binding assay, *Analytical Biochemistry* 338, 284-293.

23. Low, P. S., Henne, W. A., and Doorneweerd, D. D. (2008) Discovery and development of folic-acid-based receptor targeting for imaging and therapy of cancer and inflammatory diseases, *Acc Chem Res* 41, 120-129.

24. Al-Jamal, K. T., Ramaswamy, C., and Florence, A. T. (2005) Supramolecular structures from dendrons and dendrimers, *Advanced Drug Delivery Reviews* 57, 2238-2270.

25. Kong, H. J., Boontheekul, T, and Mooney, 0.1. (2006) Quantifying the relation between adhesion ligand-receptor bond formation and cell phenotype, *Proc Natl Acad Sci USA* 103, 18534-18539.

26. Nagrath, S., Sequist, L. V., Maheswaran, S., Bell, D. W., Irimia, D., Ulkus, L., Smith, M. R., Kwak, E. L, Digumarthy, S., Muzikansky, A., Ryan, P., Balis, U. 1., Tompkins, R, G., Haber, D. A., and Toner, M. (2007) Isolation of rare circulating tumour cells in cancer patients by microchip technology, *Nature* 450, 1235-1239.

27. Hong, S., Lee, D., Zhang, H., Zhang, J. Q., Resviek, J. N., Khademhosseini, A., King, M. R., Langer, R., and Karp, J. M. (2007) Covalent immobilization of p-selectin enhances cell rolling, *Langmuir* 23, 12261-122.68.

28. Z. Ge, J. Hu, F, Huang, S. Liu, *Angew Chain Int Ed Engl* 2009, 48, 1798-1802.

29. C. N. Urbani, C. A. Bell, D. Lonsdale, M. 12. Whittaker, M. J. Monteiro, *Macromolecules* 2008, 41, 76-86.

30. (a) H. Nandivada, X. W. Jiang, J Lahann, *Adv Mater* 2007, 19, 2197-2208; (b) W. H. Binder, R. Sachsenholer, *Macromol Rapid Comm* 2008, 29, 952-981; (c) C. Hua, C. M. Dung, Y. Wei, *Biomacromolecules* 2009, 10, 1140-1148; (d) K. D. Bodine, D. Y. Gin, M. S. Gin, *J Am Chem Sue* 2004, 126, 1638-1639; (e) R. Riva, S. Schmeits, C. Jerome, R. Jerome, P. Lecomte, *Macromolecules* 2007, 40, 796-803.

31. E. R. Gillics, J. M. Frechet, *J Am Chem Soc* 2002, 124, 14137-14146.

32. P. Becher, M. J. Schick, *Nonionic Surfactants Physical Chemistor*, MARCEL DEKKER, New York, 1987.

33. (a) J. B. Liu, F. Q. Zeng, C. Allen, *Eur Pharm Biopharm* 2007, 65, 309-319; (b) H. L. Sun, B. N. Quo, R. Cheng, F. H. Meng, H. Y. Liu, Z, Y. Zhong, *Biomaterials* 2009, 30, 6358-6366; (c) C. F. Lu, S. R. Guo, L. Liu, S. Q. Zhang, Z. H. Li, J. R. Gu, *J Polym Sci Pol Phys* 2006, 44, 3406-3417.

34. G. Gaucher, M. H. Dufresne, V. P. Sant, N. Kang, D. Maysinger, J. C. Leroux, *J Control Release* 2005, 109, 169-188.

35. (a) S. Y. Kim, I. L. G. Shin, Y. M. Lee, C. S. Cho, Y. K. Sung, *J Control Release* 1998, 51, 13-22; (b) M. L. Forrest, C. Y. Won, A. W. Malick, C, S. Kwon, *J Control Release* 2006, 110, 370-377.

36. G. B. Zhou, J. Smid, *Langmuir* 1993, 9, 2907-2913.

37. C. Tanford, *The Hydrophobic Effect: Formation of Micelles and Biological Membranes*, Wiley Sons, New York, 1973.

38. (a) L. Yang, X. Qi, P. Litt, A. El Ghzaoui, S. M. Li, *Int J Pharm* 2010, 394, 43-49; (b) T. Riley, S. Stolnik, C. R. Heald, C. D, Xiong, M. C. Garnett, L. Ilium, S. S. Davis, S. C. Purkiss, R. J. Barlow, P. R, Gellert, *Langmuir* 2001, 17, 3168-3174; c) P. Posocco, M. Fermeglia, S. Priel, *J Mater Chem* 2010, 20, 7742-7753.

39. M. Ward, *Mechanical Properties of Solid Polymers*, John Wiley and Sons, New York, 1971.

40. (a) G. M. Whitesides, J. P. Mathias, C. T. Seto, *Science* 1991, 254, 1312-1319; (b) J. N. lsraelachvili, B. J. Mitchell, B. W. Ninham, *J Chem Soc Farad T 2* 1976, 72, 1525-1568.

41. (a) T. Chen, Z. Zhang, S. C. Glotzer, *Proc Nail Acad Sci USA* 2007, 104, 717-722; (b) M. Kellermann, W. Bauer, A. Hirsch, B. Schade, K. Ludwig, C. Bottcher, *Angew Chem Int Ed Engl* 2004, 43, 2959-2962; (c) K. Kratzat, H. Finkelmann, *Langmuir* 1996, 12, 1765-1770.

42. R. Nagarajan, *Langmuir* 2002, 18, 31-38.

43. N. W. Suck, M. H. Lamm, *Langmuir* 2008, 24, 3030-3036.

44. Z. Ge, J. Hu, F. Huang and S. Liu, *Angew. Chem. Int. Ed. Engl.*, 2009, 48, 1798.

45. C. N. Urbani, C. A. Bell, D. Lonsdale, M. R. Whittaker and M. J. Monteiro, *Macromolecules*, 2008, 41, 76.

46. (a) H. S. Yoo and T. G. Park, *J. Control. Release.*, 2001, 70, 63; (b) E. R. Gillies and J. M. Frechet, *J. Am. Chem. Soc.*, 2002, 124, 14137.

47. (a) H. Nandivada, X. W. Jiang and J. Lahann, *Adv Mater,* 2007, 19, 2197; (b) W. H. Binder and R. Sachsenhofer, *Macromol. Rapid. Comm.*, 2008, 29, 952.

48. C. Hua, C. M. Dong and Y. Wei, *Biomacromolecules,* 2009, 10, 1140.

49. (a) K. D. Bodine, D. Y. Gin and M. S. Gin, *J. Am. Chem. Soc.*, 2004, 126, 1638; (b) M. J. Joralemon, R. K. O'Reilly, C. J. Hawker and K. L. Wooley, *J. Am. Chem. Soc.*, 2005, 127, 16892; (c) R. Riva, S. Schmeits, C. Jerome, R. Jerome and P. Lecomte, *Macromolecules,* 2007, 40, 796.

50. M. Wilhelm, C. L. Zhao, Y. C. Wang, R. L. Xu, M. A. Winnik, J. L. Mura, G. Riess and M. D. Croucher, *Macromolecules,* 1991, 24, 1033.

51. J. C. Phillips, R. Braun, W. Wang, J. Gumbart, E. Tajkhorshid, E. Villa, C. Chipot, R. D. Skeel, L. Kalé and K. Schulten, *J. Comput. Chem.*, 2005, 26, 1781.

52. (a) A. D. MacKerell, D. Bashford, Bellott, R. L. Dunbrack, J. D. Evanseck, M. J. Field, S. Fischer, J. Gao, H. Guo, S. Ha, D. Joseph-McCarthy, L. Kuchnir, K. Kuczera, F. T. K. Lau, C. Mattos, S. Michnick, T. Ngo, D. T. Nguyen, B. Prodhom, W. E. Reiher, B. Roux, M. Schlenkrich, J. C. Smith, R. Stote, J. Straub, M. Watanabe, J. Wiórkiewicz-Kuczera, D. Yin and M. Karplus, *The Journal of Physical Chemistry B,* 1998, 102, 3586; (b) H. Lee, R. M. Venable, A. D. MacKerell and R. W. Pastor, *Biophysical Journal,* 2008, 95, 1590; (c) K. Vanommeslaeghe, E. Hatcher, C. Acharya, S. Kundu, S. Zhong, J.

Shim, E. Darian, O. Guvench, P. Lopes, I. Vorobyov and A. D. Mackerell, *J. Comput. Chem.*, 2010, 31, 671.
53. P. P. Ewald, *Ann. Phys.*, 1921, 64, 253.
54. W. Humphrey, A. Dalke and K. Schulten, *Journal of Molecular Graphics*, 1996, 14, 33.
55. I. M. Ward, *Mechanical Properties of Solid Polymers*, John Wiley and Sons, New York, 1971.
56. Gillies, E. R., Jonsson, T. B., and Frechet, J. M. (2004) Stimuli-responsive supramolecular assemblies of linear-dendritic copolymers, *J Am Chem Soc* 126, 11936-11943.
57. Lee, H. 1, Lee, J. A., Poon, Z., and Hammond, P. T. (2008) Temperature-triggered reversible micellar self-assembly of linear-dendritic block copolymers, *Chem Commun* (Camb), 3726-3728.
58. Tian, L., Nguyen, P., and Hammond, P. T. (2006) Vesicular self-assembly of comb-dendritic block copolymers, *Chem Commun* (Camb), 3489-3491.
59. Yoshimoto, K., Hoshino, Y., Ishii, T., and Nagasaki, Y. (2008) Binding enhancement of antigen-funetionalized PEGylated gold nanoparticles onto antibody-immobilized surface by increasing the functionalized antigen using alpha-sulfanyl-omega-amino-PEG, *Chem Commun* (Camb), 5369-5371.
60. Israelachvili, J. (1995) *Intermolecular and Surface Forces*, Academic Press Inc., San Diego.
61. Cho, B. K., Jain, A., Gruner, S. M., and Wiesner, U. (2004) Mesophase structure-mechanical and ionic transport correlations in extended amphiphilic dendrons *Science* 305, 1598-1601.
62. X. Wu, J. R. Hawse, M. Subramaniam, M. P. Goetz, J. N. Ingle, T. C. Spelsberg, *Cancer Res.* 2009, 69, 1722-1727.
63. M. P. Goetz, S. K. Knox, V. J. Suman, J. M. Rae, S. L. Safgren, M. M. Ames, D. W. Visscher, C. Reynolds, F. J. Couch, W. L. Lingle, R. M. Weinshilboum, E. G. B. Fritcher, A. M. Nibbe, Z. Desta, A. Nguyen, D. A. Flockhart, E. A. Perez, J. N. Ingle, *Breast Cancer Res. Treat.* 2007, 101, 133-121.
64. J. M. Rae, *Clin. Pharmacol. Ther.* 2013, 94, 183-185.
65. O. Lee, D. Ivancic, R. T. Chatterton Jr, A. W. Rademaker, S. A. Khan, *Breast Cancer Target Therapy* 2011, 3, 61-70.
66. J. Gjerde, S. Gandini, A. Guerrieri-Gonzaga, L. L. Haugan Moi, V. Aristarco, G. Mellgren, A. Decensi, E. A. Lien, *Breast Cancer Res. Treat.* 2012, 134, 693-700.
67. E. R. Port, L. L. Montgomery, A. S. Heerdt, P. I. Borgen, *Ann. Surg. Oncol.* 2001, 8, 580-585.
68. R. Day, P. A. Ganz, J. P. Costantino, W. M. Cronin, D. L. Wickerham, B. Fisher, *J. Clin. Oncol.* 1999, 17, 2659-2669.
69. P. Rouanet, G. Linares-Cruz, F. Dravet, S. Poujol, S. Gourgou, J. Simony-Lafontaine, J. Grenier, A. Kramar, J. Girault, E. Le Nestour, T. Maudelonde, *J. Clin. Oncol.* 2005, 23, 2980-2987.
70. M. R. Prausnitz, S. Mitragotri, R. Langer, *Nat. Rev. Drug Discov.* 2004, 3, 115-124.
71. C. S. Mah, J. Singh Kochhar, P. S. Ong, L. Kang, *Intel. J. Pharm.* 2013, 441, 433-440.
72. Y. Yang, S. Sunoqrot, C. Stowell, J. Ji, C.-W. Lee, J. W. Kim, S. A. Khan, S. Hong, *Biomacromolecules* 2012, 13, 2154-2162.
73. R. K. Subedi, S. Y. Oh, M. K. Chun, H. K. Choi, *Arch. Pharm. Res.* 2010, 33, 339-351.
74. P. Karande, A. Jain, K. Ergun, V. Kispersky, S. Mitragotri, *Proc. Natl. Acad. Sci. USA* 2005, 102, 4688-4693.
75. B. C. Finnin, T. M. Morgan, *J. Pharm. Sci.* 1999, 88, 955-958.
76. R. O. Potts, R. H. Guy, *Pharm. Res.* 1992, 9, 663-669.
77. E. O. Aranda, J. Esteve-Romero, M. Rambla-Alegre, J. Peris-Vicente, D. Bose, *Talanta* 2011, 84, 314-318.
78. A. C. Williams, B. W. Barry, *Adv. Drug Deliv. Rev.* 2004, 56, 603-618.
79. Y. C. Tong, T. Y. Yu, S. F. Chang, J. H. Liaw, *Mol. Pharm.* 2012, 9, 111-120.
80. D. E. Poree, M. D. Giles, L. B. Lawson, J. He, S. M. Grayson, *Bio-macromolecules* 2011, 12, 898-906.
81. Y. G. Bachhav, K. Mondon, Y. N. Kalia, R. Gurny, M. Moller, *J. Control. Release* 2011, 153, 126-132.
82. A. Spernath, A. Aserin, A. C. Sintov, N. Garti, *J. Colloid Interface Sci.* 2008, 318, 421-429.
83. Y. Yang, J. Bugno, S. Hong, *Polym. Chem.* 2013, 4, 2651-2657.
84. R. M. Pearson, S. Sunogrot, H.-J. Hsu, J. W. Bae, S. Hong, *Ther. Deliv.* 2012, 3, 941-959.
85. J. W. Bae, R. M. Pearson, N. Patra, S. Sunogrot, L. Vukovic, P. Kral, S. Hong, *Chem. Commun.* 2011, 47, 10302-10304.
86. R. M. Pearson, N. Patra, H.-J. Hsu, S. Uddin, P. Kral, S. Hong, *ACS Macro Lett.* 2013, 2, 77-81.
87. K. Kajimoto, M. Yamamoto, M. Watanabe, K. Kigasawa, K. Kanamura, H. Harashima, K. Kogure, *Intl. J. Pharm.* 2011, 403, 57-65.
88. J. A. Bouwstra, P. L. Honeywell-Nguyen, G. S. Gooris, M. Ponec, *Prog. Lipid Res.* 2003, 42, 1-36.
89. W. A. T. Al-Jamal, K. Kostarelos, *Accounts Chem. Res.* 2011, 44, 1094-1104.
90. M. L. Turco Liveri, M. Licciardi, L. Sciascia, G. Giammona, G. Cavallaro, *J. Phys. Chem. B* 2012, 116, 5037-5046.
91. Y. Yang, C. Hua, C.-M. Dong, *Biomacromolecules* 2009, 10, 2310-2318.
92. D. D. Verma, S. Verma, G. Blume, A. Fahr, *Intl. J. Pharm.* 2003, 258, 141-151.
93. L. Barbosa-Barros, C. Barba, G. Rodriguez, M. Cocera, L. Coderch, C. Lopez-Iglesias, A. de la Maza, O. Lopez, *Mol. Pharm.* 2009, 6, 1237-1245.
94. Z. V. Leonenko, E. Finot, H. Ma, T. E. S. Dahms, D. T. Cramb, *Bio-phys. J.* 2004, 86, 3783-3793.
95. C. Gregor, *Adv. Drug Deliv. Rev.* 2004, 56, 675-711.
96. W. A. G. Bruls, H. Slaper, J. C. Van Der Leun, L. Berrens, *Photochem. Photobiol.* 1984, 40, 485-494.
97. V. P. Shah, C. C. Peck, R. L. Williams, *Pharmaceut. Skin Penetration Enhancement* 1993, 19, 417-427.
98. E. Hendradi, Y. Obata, K. Isowa, T. Nagai, K. Takayama, *Biol. Pharm. Bull.* 2003, 26, 1739-1743.
99. M. T. Sheu, S. Y. Chen, L. C. Chen, H. O. Ho, *J. Control. Release* 2003, 88, 355-368.
100. S. Ghosh, S. Hornby, G. Grove, C. Zerwick, Y. Appa, D. Blankschtein, *J. Cosmest. Sci.* 2007, 58, 599-620.
101. S. Ghosh, D. Blankschtein, *J. Cosmest. Sci.* 2008, 58, 229-244.
102. S. Mitragotri, *J. Control. Release* 2003, 86, 69-92.
103. E. Pozo-Guisado, A. Alvarez-Barrientos, S. Mulero-Navarro, B. Santiago-Josefat, P. M. Fernandez-Salguero, *Biochem. Pharmacol.* 2002, 64, 1375-1386.
104. F. Benavides, T. M. Oberyszyn, A. M. VanBuskirk, V. E. Reeve, D. F. Kusewitt, *J. Dermatol. Sci.* 2009, 53, 10-18.
105. V. V. K. Venuganti, O. P. Perumal, *Intl. J. Pharm.* 2008, 361, 230-238.
106. H. R. Moghimi, A. Alinaghi, M. Erfan, *Intl. J. Pharm.* 2010, 401, 47-50.

We claim:

1. A method of dermal delivery with enhanced skin permeation of a drug to a patient comprising administering onto skin of the patient a topical composition comprising a micelle and a pharmaceutically acceptable excipient, wherein the drug has a molecular weight over 500 g/mol, a 1-octanol/PBS partition coefficient (log P) less than 1 or greater than 3, or both, wherein the micelle comprises amphiphilic dendron-coils and encapsulates the drug, and wherein each amphiphilic dendron-coil comprises a hydrophobic core-forming block, a polyester dendron and a poly(ethylene) glycol (PEG) moiety.

2. The method of claim 1:

wherein the hydrophobic core-forming block comprises polycaprolactone (PCL), poly(lactic acid) (PLA), poly (glycolic acid) (PGA) or poly(lactic-co-glycolic acid) (PLGA);

wherein the polyester dendron is a generation 3 to generation 5 polyester dendron with either an acetylene or carboxylate core;

wherein the PEG moiety is a methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide-activated PEG (PEG-NHS) moiety, NH$_2$-PEG-NH$_2$ moiety, or NH$_2$-PEG-COOH moiety; and wherein the enhanced skin permeation is characterized by drug from the topical composition exhibiting higher permeation (P<0.05) within 24 hours through either human skin or hairless mouse skin than drug from a control topical composition comprising either, for human skin, free drug in 60% (v/v) ethanol in phosphate buffered solution (PBS, that is, water buffered with 2 mM KH$_2$PO$_4$ and 4 mM Na$_2$HPO$_4$), or, for hairless mouse skin, free drug in 60% (v/v) ethanol in double distilled water.

3. The method of claim 2 wherein the PEG moiety is amine-terminated PEG (PEG-NH$_2$) moiety, acetylated PEG (PEG-Ac) moiety, or carboxylated PEG (PEG COOH) moiety.

4. The method of claim 2 wherein the hydrophobic core-forming block comprises PCL.

5. The method of claim 2 wherein the hydrophobic core-forming block comprises PLA.

6. The method of claim 2 wherein the hydrophobic core-forming block comprises PGA.

7. The method of claim 2 wherein the hydrophobic core-forming block comprises PLGA.

8. The method of claim 4 wherein the PCL is poly(ε-caprolactone).

9. The method of claim 1, 2, 3, 4, 5, 6, 7 or 8 wherein the hydrophobic core-forming block has a molecular weight from about 0.5 kDa to about 20 kDa.

10. The method of claim 8 wherein the poly(ε-caprolactone) has a molecular weight of about 3.5 kDa.

11. The method of claim 8 wherein the poly(ε-caprolactone) has a molecular weight of about 14 kDa.

12. The method of claim 1 wherein the polyester dendron has an acetylene core.

13. The method of claim 1 wherein the polyester dendron has a carboxylate core.

14. The method of claim 3 wherein the polyester dendron has an acetylene core.

15. The method of claim 3 wherein the polyester dendron has a carboxylate core.

16. The method of claim 4 or 8 wherein the polyester dendron has an acetylene core.

17. The method of claim 10 wherein the polyester dendron has an acetylene core.

18. The method of claim 11 wherein the polyester dendron has an acetylene core.

19. The method of claim 1, 12 or 13 wherein the polyester dendron is a generation 3 (G3) dendron.

20. The method of claim 1, 12 or 13 wherein the polyester dendron is a generation 4 (G4) dendron.

21. The method of claim 1, 12 or 13 wherein the polyester dendron is a generation 5 (G5) dendron.

22. The method of claim 12 wherein the polyester dendron is a generation 3 polyester-8-hydroxyl-1-acetylene bis-MPA dendron.

23. The method of claim 1 wherein the PEG moiety is a methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide-activated PEG (PEG-NHS) moiety, NH$_2$-PEG-NH$_2$ moiety, or NH$_2$-PEG-COOH moiety.

24. The method of any one of claim 12, 13, or 22 wherein the PEG moiety is a methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide-activated PEG (PEG-NHS) moiety, NH$_2$-PEG-NH$_2$ moiety, or NH$_2$-PEG-COOH moiety.

25. The method of claim 1 wherein the PEG moiety has a molecular weight from about 0.2 kDa to about 5 kDa.

26. The method of claim 24 wherein the PEG moiety has a molecular weight from about 0.2 kDa to about 5 kDa.

27. The method of claim 1 wherein the micelle further comprises one or more ligands conjugated to one or more PEG moieties.

28. The method of claim 1 wherein the micelle further comprises a chemical penetration enhancer.

29. The method of claim 1 wherein the drug is hydrophobic.

30. The method of claim 1 wherein the drug is a cancer drug.

31. The method of claim 30 wherein the cancer drug is paclitaxel, methotrexate, doxorubicin, cisplatin, carboplatin, tamoxifen, 4-hydroxytamoxifen, endoxifen, fulvestrant; canstatin, proliferin-related protein, restin, maspin, osteopontin, Secreted Protein Acidic and Rich in Cysteine (SPARC) protein, Vascular Endothelial cell Growth Inhibitor (VEGI), prolactin, prothrombin, Interferon (IFN)-alpha, IFN-beta, IFN-gamma, C—X—C motif chemokine 10 (CXCL10), Interleukin (IL)-4, IL-12, metalloprotease and Thrombospondin domains protein (METH)-1 and METH-2, Tissue Inhibitors of metalloproteinase (TIMP), cell division autoantigen 1 (CDA1), platelet factor-4, vasostatin, calreticulin, endostatin, angiostatin, thrombospondin (TSP)-1 and TSP-2, Angiopoietin 2, Vascular Endothelial Growth Factor Receptor (VEGFR)-1, or Novel SH2-containing Protein 1 (NSP-1).

32. The method of claim 1 wherein the dermal delivery of the drug is prolonged.

33. The method of claim 1 wherein the dermal delivery of the drug is biphasic.

34. A method of dermal delivery with enhanced skin permeation of a drug to a patient comprising administering onto skin of the patient a topical composition comprising a micelle and a pharmaceutically acceptable excipient, wherein:

the drug has a molecular weight over 500 g/mol, the drug has a 1-octanol/PBS partition coefficient (log P) less than 1 or greater than 3, or both;

the micelle comprises amphiphilic dendron-coils and encapsulates the drug;

each amphiphilic dendron-coil comprises a hydrophobic core-forming block, a polyester dendron, and a poly(ethylene) glycol (PEG) moiety;

the hydrophobic core-forming block comprises polycaprolactone (PCL), poly(lactic acid) (PLA), poly(glycolic acid) (PGA), or poly(lactic-co-glycolic acid) (PLGA);

the polyester dendron is a generation 3 to generation 5 polyester dendron with either an acetylene or carboxylate core;

the PEG moiety is methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide-activated PEG (PEG-NHS) moiety, NH$_2$-PEG-NH$_2$ moiety, or NH$_2$-PEG-COOH moiety; and the enhanced skin permeation is characterized by drug from the topical composition exhibiting higher permeation (P<0.05) within 24 hours through human skin than drug from a control topical composition comprising free drug in 60% (v/v) ethanol in phosphate buffered solution (PBS, that is, water buffered with 2 mM KH$_2$PO$_4$ and 4 mM Na$_2$HPO$_4$).

35. A method of dermal delivery with enhanced skin permeation of a drug to a patient comprising administering onto skin of the patient a topical composition comprising a micelle and a pharmaceutically acceptable excipient, wherein:

the drug has a molecular weight over 500 g/mol, the drug has a 1-octanol/PBS partition coefficient (log P) less than 1 or greater than 3, or both;

the micelle comprises amphiphilic dendron-coils and encapsulates the drug;

each amphiphilic dendron-coil comprises a hydrophobic core-forming block, a polyester dendron and a poly(ethylene) glycol (PEG) moiety;

the hydrophobic core-forming block comprises polycaprolactone (PCL), poly(lactic acid) (PLA), poly(glycolic acid) (PGA), or poly(lactic-co-glycolic acid) (PLGA);

the polyester dendron is a generation 3 to generation 5 polyester dendron with either an acetylene or carboxylate core;

the PEG moiety is methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide-activated PEG (PEG-NHS) moiety, NH$_2$-PEG-NH$_2$ moiety, or NH$_2$-PEG-COOH moiety; and the enhanced skin permeation is characterized by drug from the topical composition exhibiting higher permeation (P<0.05) within 24 hours through hairless mouse skin than drug from a control topical composition comprising free drug in 60% (v/v) ethanol in double distilled water.

\* \* \* \* \*